United States Patent [19]

Atkinson et al.

[11] Patent Number: 4,663,347
[45] Date of Patent: May 5, 1987

[54] BENZOFURAN 2-CARBOXYLIC ACID ESTERS USEFUL AS INHIBITORS OF LEUKOTRIENE BIOSYNTHESIS

[75] Inventors: Joseph G. Atkinson, Montreal; Yvan Guindon, Ile Bizard; Cheuk K. Lau, Pierrefonds, all of Canada

[73] Assignee: Merck Frosst Canada, Inc., Quebec, Canada

[21] Appl. No.: 725,265

[22] Filed: Apr. 19, 1985

Related U.S. Application Data

[63] Continuation-in-part of Ser. No. 661,645, Oct. 17, 1984, abandoned, which is a continuation-in-part of Ser. No. 547,508, Oct. 31, 1983, abandoned.

[51] Int. Cl.⁴ ............... A61K 31/34; C07D 307/85
[52] U.S. Cl. .................... 514/467; 514/321; 514/337; 514/443; 514/463; 514/469; 546/196; 546/269; 548/251; 549/433; 549/435; 549/448; 549/466; 549/467; 549/468; 549/470; 549/471
[58] Field of Search ............... 549/468, 448; 514/469, 514/467

[56] References Cited

U.S. PATENT DOCUMENTS

| | | | |
|---|---|---|---|
| 3,557,152 | 1/1971 | Zergenyi et al. | 549/468 |
| 3,574,208 | 4/1971 | Zergenyi et al. | 424/285 |
| 3,627,785 | 12/1971 | Zergenyi et al. | 549/468 |
| 3,665,074 | 5/1972 | Brandstrom et al. | 549/467 |
| 3,674,810 | 7/1972 | Zergenyi et al. | 549/468 |
| 3,723,619 | 3/1973 | Zergenyi et al. | 424/285 |
| 3,830,929 | 8/1974 | Nordmann et al. | 549/467 |
| 3,915,687 | 10/1975 | Braunling et al. | 71/88 |
| 4,055,117 | 10/1977 | Munday | 101/11 |
| 4,085,117 | 4/1978 | Crajoe, Jr. et al. | 549/468 |
| 4,100,294 | 7/1978 | Cragoe, Jr. et al. | 424/275 |
| 4,213,998 | 7/1980 | Witiak | 424/285 |
| 4,229,467 | 10/1980 | Parker | 424/285 |
| 4,424,231 | 1/1984 | Bantick et al. | 549/468 |

FOREIGN PATENT DOCUMENTS

| | | |
|---|---|---|
| EP19955 | 12/1980 | European Pat. Off. |
| 45473 | 2/1982 | European Pat. Off. |
| 73663 | 3/1983 | European Pat. Off. |
| 69521 | 12/1983 | European Pat. Off. |
| 123543 | 10/1984 | European Pat. Off. |
| 1212984 | 3/1966 | Fed. Rep. of Germany |
| 2909754 | 9/1980 | Fed. Rep. of Germany |
| 2231372 | 2/1974 | France |
| 50-049270 | 5/1975 | Japan |
| 56039015 | 9/1979 | Japan |
| 57-040479 | 3/1982 | Japan |
| 500966 | 2/1971 | Switzerland |
| 540900 | 8/1973 | Switzerland |
| 1233268 | 5/1971 | United Kingdom |
| 1464242 | 2/1977 | United Kingdom |
| 2007973 | 5/1979 | United Kingdom |
| 399106 | 9/1973 | U.S.S.R. |

OTHER PUBLICATIONS

Rene Royer et al., Eur. J. Med. Chem. Chimica Therapeutica, Mar.-Apr. 1974-9, No. 2, pp. 136-145.
W. B. Whalley, J. Chem. Soc., pp. 3229-3235 (1951).
Fujiwara et al., J. Org. Chem., 46, 851 (1981).
Chem. Abstracts, 65, 18546h.
Chem. Abstracts, 58, 13881c.
Chem. Ber., 99 (6), 2063-2065 (1966).
Rodighiero and Fornasiero, Gazz. Chim. Ital., 91, 90-102 (1961).
Die Pharmazie 35, No. 9, pp. 517-539, (Sep. 1980).

Primary Examiner—Henry R. Jiles
Assistant Examiner—Bernard I. Dentz
Attorney, Agent, or Firm—Gabriel Lopez; Hesna J. Pfeiffer

[57] ABSTRACT

Compounds of the Formula I:

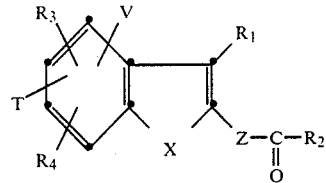

and pharmaceutically acceptable salts thereof are inhibitors of leukotriene biosynthesis. These compounds inhibit the mammalian 5-lipoxygenase enzyme, thus preventing the metabolism of arachidonic acid to the leukotrienes. These compounds are thus useful in the treatment of asthma, allergic disorders, inflammation, skin diseases and certain cardiovascular disorders.

6 Claims, No Drawings

BENZOFURAN 2-CARBOXYLIC ACID ESTERS USEFUL AS INHIBITORS OF LEUKOTRIENE BIOSYNTHESIS

This application is a CIP of U.S. Ser. No. 661,645, filed Oct 17, 1984 now abandoned, which is a continuation-in-part of U.S. Ser. No. 547,508, filed Oct. 31, 1983, now abandoned.

This invention is directed to a series of benzofuran and benzothiophene compounds, especially useful as inhibitors of the mammalian 5-lipoxygenase enzyme system. The 5-lipoxygenase enzyme controls the biosynthesis of the class of compounds known as leukotrienes. Inhibition of the 5-lipoxygenase enzyme therefore prevents or diminishes the adverse effects of the leukotrienes in a mammalian subject.

The leukotrienes are a novel group of biologically active mediators derived from arachidonic acid through the action of the 5-lipoxygenase enzyme system. The leukotrienes play an important role in inducing allergic reactions, such as asthma, allergic bronchitis or allergic rhinitis in man. One of the leukotrienes ($B_4$) contributes to both inflammation and allergic reactions in man.

There are two groups of leukotrienes derived from a common unstable precursor, Leukotriene $A_4$. The first of these are the peptido-lipid leukotrienes, the most important being Leukotrienes $C_4$ and $D_4$. These compounds collectively account for the biologically active materials known as the slow reacting substances of anaphylaxis. They are potent smooth muscle contracting agents, particularly on respiratory smooth muscle but also on other tissues (e.g., gall bladder). In addition, they promote mucous production, modulate vascular permeability changes and are potent inflammatory agents in human skin.

The most important compound in the second group of leukotrienes is Leukotriene $B_4$, a dihydroxy fatty acid derived from Leukotriene $A_4$. This compound is a potent chemotactic agent for neutrophils and eosinophils. When injected in vivo, in addition to promoting the accumulation of leukocytes, Leukotriene $B_4$ is also a potent hyperalgesic agent and can modulate vascular permeability changes through a neutrophil dependent mechanism. Both groups of leukotrienes are formed following oxygenation of arachidonic acid through the action of the 5-lipoxygenase enzyme. See D. Bailey and F. Casey, *Ann. Rpts. Med. Chem.* 17 203 (1982).

Leukotrienes can also mediate other diseases. These include psoriasis, atopic dermatitis, gouty arthritis and gall bladder spasms. In addition, they may have a role in cardiovascular disease because Leukotrienes $C_4$ and $D_4$ act as coronary and cerebral arterial vasoconstrictors and these compounds may also have negative inotropic effects on the myocardium. In addition, the Leukotrienes are important mediators of inflammatory diseases through their ability to modulate leukocyte and lymphocyte function. See: B. Sameulsson, *Science* 220 568 (1983).

Benzo[b]furan derivatives having the formula:

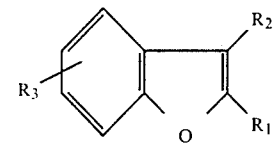

especially wherein $R_1$ is alkyl, OH, $N(R)_2$ or alkyl-$N(R)_2$; $R_2$ is lower alkyl; and $R_3$ is alkyl, are known compounds. See for example: European Patent Application No. 45,473; Japanese Kokai Koho No. 50,049,270 (Derwent No. 57847 W/35); German Pat. No. 1,212,984; Belgium Pat. No. 795,671; Russian Pat. No. 399,106 (Derwent No. 59399 V/33); French Pat. No. 2,231,372; U.S. Pat. No. 4,213,998; Japanese Kokai Koho No. 56,039.015 (Derwent No. 39263 D/22); Japanese Kokai Koho No. 57,040,479 (Derwent No. 29877 E/15); Netherlands Pat. No. 68,10305; Netherlands Pat. No. 68,10314; Netherlands Pat. No. 68,10315; German Offen. No. 1,932,933; German Offen. No. 1,937,056; Belgium Pat. No. 828,022; Belgium Pat. No. 656,100; Belgium Pat. No. 671,060; Switzerland Pat. No. 540,900; U.S. Pat. No. 4,055,117; German Offen. No. 2,754,068; Belgium Pat. No. 868,528; U.S. Pat. No. 4,229,467; Switzerland Pat. No. 500,966; Great Britain Pat. No. 1,233,268; U.S. Pat. No. 3,915,687; German Offen. No. 2,909,754; European Patent Application Nos. 73,663; 69,521; Chemical Abstracts, 67, 82016e, U.S. Pat. No. 3,574,208 and U.K. Patent Application No. 2,091,719A.

None of the above compounds are taught to possess 5-lipoxygenase inhibition activity or utility as mammalian leukotriene biosynthesis inhibitors.

This invention is directed to pharmaceutical compositions containing a compound of the Formula I:

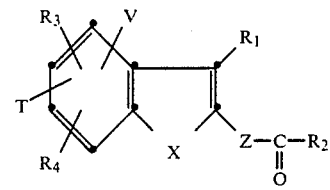

and pharmaceutically acceptable salts thereof wherein the various substituents are as defined herein below.

This invention also provides a method of treatment for disease states caused by the synthesis of the Leukotrienes $C_4$, $D_4$, $E_4$ and $F_4$, as well as Leukotriene $B_4$, in mammals especially in a human subject. This method comprises administering to said subject an effective amount of a compound of Formula I combined with an appropriate pharmaceutical carrier.

The compounds of Formula I may be used to treat or prevent mammalian (especially human) disease states such as erosive gastritis; erosive esophagitis; inflammatory bowel disease; ethanol-induced hemorrhagic erosions; hepatic ischemia; noxious agent induced damage or necrosis of hepatic, pancreatic, renal, or myocardial tissue; liver parenchymal damage caused by hepatoxic agents such as $CCl_4$ and D-galactosamine; ischemic renal failure; disease-induced hepatic damage; bile salt induced pancreatic or gastric damage, trauma- or stress-induced cell damage; and glycerol-induced renal failure.

Finally, this invention also provides novel compounds within the Formula I that act as inhibitors of the mammalian 5-lipoxygenase enzyme system, thus preventing the biosynthesis of the Leukotrienes $C_4$, $D_4$ and $E_4$ and also Leukotriene $B_4$.

DETAILED DESCRIPTION OF THE INVENTION

One embodiment of the present invention is a pharmaceutical composition containing a compound of the Formula I and an acceptable pharmaceutical carrier:

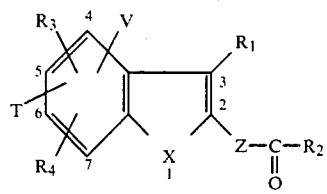

wherein:

Z is a bond, $CR_{14}=CR_{15}$ or $CHR_{14}-CHR_{15}$;

X is O, S, SO, or $SO_2$;

$R_2$ is H, OH, $C_1$ to $C_{20}$ alkoxy, including straight chain or branched chain, cycloalkyl, bicycloalkyl, tricycloalkyl or tetracycloalkyl;

$Ar_1-C_1$ to $C_3$ alkoxy;

$NR_8Ar_1$, wherein $R_8$ and $Ar_1$ can optionally be joined to form a heterocyclic ring having 5 to 8 ring atoms;

—$NR_8Het$;

—$N(R_8)CH_2Ar_1$;

—$N(R_{13})$—$N(R_{13})_2$ wherein each $R_{13}$ is independently hydrogen, $R_8$, $R_9$, $Ar_1$ or Het;

—$NH-CH=C(Ar_1)_2$;

—$O(CH_2)_nNR_8R_9$ wherein n is 2 to 4;

—$Z-Ar_1$;

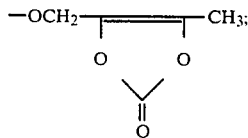

—lower acyloxy-lower alkoxy

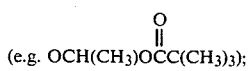

(e.g. $OCH(CH_3)OCC(CH_3)_3$);

—$CH_2OH$;

—$(CH_2)_nAr_1$ wherein n is 0 to 3;

—$(CH_2)_nCOOR_6$ wherein n is 0 to 6;

$C_1$ to $C_{20}$ alkyl; $Ar_1$; Het; $(CH_2)_nNR_8R_9$ wherein n is 1 to 3; or Het;

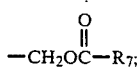

and $R_1$, $R_3$, $R_4$, T and V are each independently selected from:

(1) hydrogen;
(2) alkyl having 1 to 6 carbon atoms;
(3) alkenyl having 2 to 6 carbon atoms;
(4) —$(CH_2)_nM$ wherein n is 0 to 6 except when X is S and M is $OR_5$, in which case n is 1 to 6 and M is (a) —$OR_5$;

(b) halogen;
(c) —$CF_3$;
(d) —$SR_5$;
(e) $Ar_1$;
(f) —$COOR_6$;
(g)

wherein $R_{12}$ is H, $C_1$ to $C_6$ alkyl, or $Ar_1$;

(h) tetrazole;

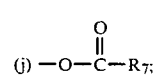

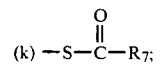

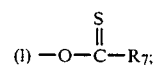

(m) —$NR_8R_9$;

(n) —$NHSO_2R_{10}$ wherein $R_{10}$ is OH, $C_1$ to $C_6$ alkyl, $CF_3$, $C_1$ to $C_6$-alkoxy, or $Ar_1$;

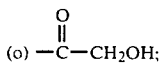

(p) —$SOR_5$;
(q) —$CONR_8R_9$;
(r) —$SO_2NR_8R_9$;
(s) —$SO_2R_5$;
(t) —$NO_2$; or
(u) —CN;

or any two of $R_3$, $R_4$, T and V may be joined to form a saturated ring having 5 or 6 ring atoms, said ring atoms comprising 0, 1 or 2 atoms selected from oxygen and sulfur, the remaining ring atoms being carbon;

each $R_5$ is independently H, $C_1$ to $C_6$ alkyl, benzyl, $Ar_1$, perfluoro-$C_1$ to $C_4$ alkyl, $CH_2-R_{11}$ wherein $R_{11}$ is $C_1$ to $C_5$ alkyldimethylamino, hydroxy-$C_2$ to $C_5$ alkyl, $CH_2COOR_6$, or $CH_2CO-R_7$;

each $R_6$ is independently H or $C_1$ to $C_6$ alkyl;

each $R_7$ is independently $C_1$ to $C_6$ alkyl, benzyl, $Ar_1$, $NR_8R_9$, $NHAr_1$, or O—$C_1$ to $C_4$ alkyl;

each $R_8$ and each $R_9$ is independently H or $C_1$ to $C_4$ alkyl, or $R_8$ and $R_9$ may be joined through the N to which they are attached to form a heterocycloalkyl ring having 5 to 8 ring atoms;

each Het is independently an aromatic heterocyclic ring having 5 or 6 ring atoms, one or more of which are selected from N, O and S;

each $Ar_1$ is independently 1- or 2-naphthyl, phenyl or mono- or disubstituted phenyl, wherein the substituents on the phenyl are independently selected from $C_1$ to $C_3$ alkyl, I, Br, Cl, F, $COOR_6$, $(CH_2)_n-NR_8R_9$ wherein n is 0 to 2, methylenedioxy, $C_1$ to $C_3$ alkoxy, OH, CN, $NO_2$, $CF_3$, $C_1$ to $C_4$ acyl, $NR_8R_9$, S—$C_1$ to $C_6$ alkyl, SO—$C_1$ to $C_6$ alkyl, and $SO_2$—$C_1$ to $C_6$ alkyl; and $R_{14}$ and $R_{15}$ are each independently H or $C_1$ to $C_6$ alkyl; or a pharmaceutically acceptable salt thereof.

The numbers surrounding Formula I designate the substituent positions, and $R_3$, $R_4$, T and V may be positioned anywhere in the structure except at positions 1, 2 or 3.

Where possible, the appropriate pharmaceutically acceptable salts of Formula I are included within the definitions shown above.

The pharmaceutical compositions of the present invention comprise a compound of formula I as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases including inorganic bases and organic bases. Salts derived from inorganic bases include sodium, potassium, lithium, ammonium, calcium, magnesium, ferrous, zinc, copper, manganous, aluminum, ferric, manganic salts and the like. Particularly preferred are the ammonium, potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine trimethylamine, diethylamine, triethylamine, tripropylamine, ethanolamine, 2-dimethylaminoethanol, 2-diethylaminoethanol, tromethamine, lysine, arginine, histidine, caffeine, procaine, hydrabamine, choline, betaine, ethylenediamine, glucosamine, methylglucamine, theobromine, purines, piperazine, piperidine, N-ethylpiperidine, N,N$^1$-dibenzylethylenediamine, morpholine, N-ethyl morpholine, polyamine resins and the like.

When the compound of Formula I is basic, salts may be prepared from pharmaceutically acceptable non-toxic acids, including inorganic and organic acids. Such acids include hydrochloric, hydrobromic, sulfuric, nitric, isethionic, methanesulfonic, ethanesulfonic, benzenesulfonic, p-toluenesulfonic, acetic, benzoic, camphorsulfonic, citric, fumaric, gluconic, glutamic, lactic, malic, maleic, mandelic, mucic, pamoic, pantothenic, phosphoric, succinic, tartaric acid and the like. Particularly preferred are hydrochloric, hydrobromic, citric, maleic, phosphoric, sulfuric and tartaric acids. For a helpful discussion of pharmaceutical salts see S. M. Berge et al., Journal of Pharmaceutical Sciences, 66, 1-19 (1977), the disclosure of which is hereby incorporated herein by reference.

The term alkyl, unless otherwise indicted, includes straight chain, branched chain and cycloalkyl, bicycloalkyl, tricycloalkyl or tetracycloalkyl groups of the number of carbon atoms shown. The term halogen, unless otherwise indicated, includes Cl, Br, I and F.

A preferred embodiment of the present invention is a composition comprising of Formula I wherein Z is a bond, V is hydrogen and the remaining substituents are as defined for Formula I.

Another preferred composition is comprised of compounds having the Formula Ia:

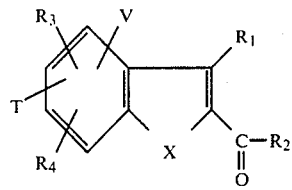

wherein X is O or S, and $R_1$, $R_2$, $R_3$, $R_4$, T and V are as defined for Formula I. In a preferred embodiment, V is hydrogen.

A still more preferred composition is comprised of compounds having the Formula Ib:

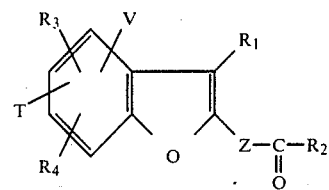

wherein $R_2$ is $C_1$ to $C_{12}$ alkoxy, including straight chain or branched chain, cycloalkyl, bicycloalkyl, tricycloalkyl or tetracycloalkyl;
—OCH$_2$Ar$_1$,
—N(R$_8$)CH$_2$Ar$_1$;
—N(R$_{13}$)—N(R$_{13}$)$_2$;
—NH—CH=C(Ar$_1$)$_2$;
—NR$_8$Ar$_1$
—CH$_2$OH;
—CH$_2$OCOR$_7$;
—(CH$_2$)$_n$Ar$_1$ wherein n is 0 to 3;
—(CH$_2$)$_n$COOR$_6$ wherein n is 0 to 4;
—C$_1$ to C$_{12}$ alkyl;

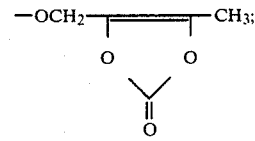

lower acyloxy-lower alkoxy;
$R_1$ is hydrogen, $C_1$ to $C_6$ alkyl, Ar$_1$—$C_1$ to $C_3$ alkyl, Ar$_1$; or —CH$_2$OH;
$R^3$, $R^4$, T and V are independently selected from:
(1) hydrogen;
(2) alkyl having 1 to 4 carbon atoms;
(3) alkenyl having 2 to 4 carbon atoms;
(4) —(CH$_2$)$_n$M wherein n is 0 or 1, and
  M is (a) —OR$_5$;
  (b) halogen;
  (c) —CF$_3$;
  (d) —SR$_5$;
  (e) —SOR$_5$;
  (f) —SO$_2$R$_5$;
  (g) —Ar$_1$;
  (h) —COOR$_6$;

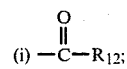

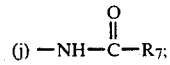

-continued

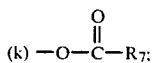
(k)

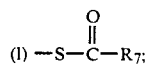
(l)

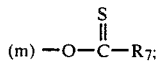
(m)

(n) —NR$_8$R$_9$;

(o) —NHSO$_2$R$_{10}$ wherein R$_{10}$ is C$_1$ to C$_6$ alkyl, phenyl, p-tolyl or CF$_3$;

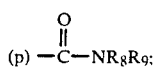
(p)

(q) —SO$_2$NR$_8$R$_9$;
(r) —NO$_2$; or
(s) —CN;

or any two of R$_3$, R$_4$, T and V may be joined to form a saturated ring having 5 or 6 ring atoms, said ring atoms comprising 0, 1 or 2 oxygen atoms, the remaining ring atoms being carbon;

and wherein all of the substituents not defined above are as defined for Formula I.

A still more preferred composition is compound of compounds having the Formula Ib wherein V is hydrogen and Z is a bond.

A particularly preferred composition is comprised of compounds of Formula Ic:

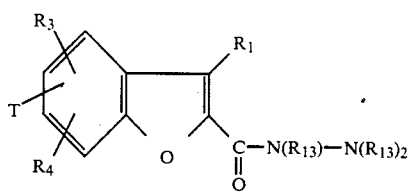
Ic wherein: R$_1$, R$_3$, R$_4$ and T are as defined for Formula Ib, at least one of the R$_{13}$ groups is not hydrogen, and one of R$_3$, R$_4$ and T is OR$_5$ or —OCOR$_7$. These compounds are all novel.

A particularly preferred composition is comprised of compounds of Formula Id:

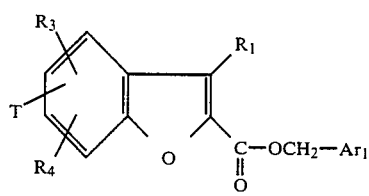
Id wherein: R$_1$, R$_3$, R$_4$, T and Ar$_1$ are as defined for Formula Ib, but at least one of R$_3$, R$_4$ or T is either OR$_5$ or —OCOR$_7$. These compounds are all novel.

Another particularly preferred composition is comprised of compounds of Formula Ib wherein V is hydrogen and Z is a bond but wherein at least one of R$_3$, R$_4$ and T is —CH$_2$SR$_5$. These compounds are all novel.

Another particularly preferred composition is comprised of compounds of Formula Ib wherein V is hydrogen and Z is a bond, but wherein at least one of R$_3$, R$_4$ and T is —OCO—C$_1$ to C$_6$ alkyl or —OCO$_2$—C$_1$ to C$_6$ alkyl.

A particularly preferred embodiment are the compounds of Formula Ie:

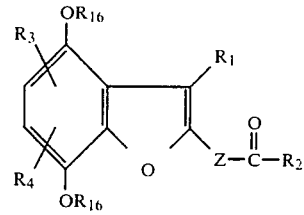
Ie wherein
R$_1$, R$_2$, R$_3$ and R$_4$ are as defined for Ib;
R$_{16}$ is R$_5$ or —COR$_7$, wherein R$_5$ and R$_7$ are as defined for Ib;
Z is a bond or —CR$_{14}$=CR$_{15}$ wherein R$_{14}$ and R$_{15}$ are as defined for I.

A preferred embodiment of the compounds included in formula Ie are those wherein:
R$_2$ is C$_1$–C$_{12}$ alkoxy, including straight chain, or branched chain or cycloalkyl;
—OCH$_2$Ar$_1$;
—N(R$_{13}$)—N(R$_{13}$)$_2$ provided that at least one R$_{13}$ is not hydrogen;
—NR$_8$Ar$_1$;

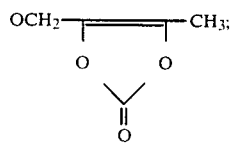

or
-lower acyloxy-lower alkoxy;
R$_1$ is C$_1$ to C$_6$ alkyl;
R$^3$ and R$^4$ are independently selected from:
(1) hydrogen;
(2) alkyl having 1 to 4 carbon atoms;
(3) alkenyl having 2 to 4 carbon atoms;
(4) —(CH$_2$)$_n$M wherein n is 0 or 1, and
  M is (a) —OR$_5$;
  (b) halogen;
  (c) —CF$_3$;
  (d) —SR$_5$;

(e)

(f)

(g) —NHSO$_2$R$_{10}$ wherein R$_{10}$ is C$_1$ to C$_6$ alkyl, phenyl, p-tolyl or CF$_3$;
or R$_3$ and R$_4$ may be joined to form a saturated ring having 5 or 6 ring atoms, said ring atoms comprising 0, 1 or 2 oxygen atoms, the remaining ring atoms being carbon.

A preferred embodiment of the compositions included in Formula Ie are those wherein R$_2$ is —OCH$_2$Ar$_1$ wherein Ar$_1$ is as defined for Ie, the remaining substituents are as defined for Ie but at least one of $R_3$ or $R_4$ is not hydrogen. These compounds are all novel.

Another preferred embodiment of the compositions of Formula Ie are those wherein $R_2$ is —N($R_{13}$)—N($R_{13}$)$_2$, wherein $R_{13}$ is as defined for Ie but at least one of the $R_{13}$ groups is not hydrogen, and the remaining substituents are as defined for Ie but at least one of $R_3$ or $R_4$ is not hydrogen (preferably, one $R_{13}$ is Het or Ar$_1$). These compounds are all novel.

A further preferred embodiment of the compositions of Formula Ie are those wherein $R_{16}$ is

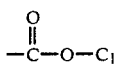

to $C_4$ alkyl and the remaining substituents are as defined for Ie. These compounds are all novel.

Another preferred embodiment of the compositions of Formula Ie are those wherein at least one of $R_3$ or $R_4$ is —CH$_2$SR$_5$ wherein $R_5$ and the remaining substituents are as defined for Ie. These compounds are all novel.

Yet another preferred embodiment of the compositions of Formula Ie are those wherein both $R_3$ and $R_4$ are —OR$_5$ wherein $R_5$ is as defined for Ie or $R_3$ and $R_4$ are joined to form a ring having 5 or 6 members, said ring containing two oxygen atoms (e.g. —OCH$_2$O—), and the remaining substituents are as defined for Ie. These compounds are all novel.

Certain compounds of the present invention are asymmetric. The scope of the present invention is meant to include the optical isomers and possible diastereoisomers included by the representation of the two-dimensional formulae.

Examples of Formula I compounds useful in the present invention are tabulated below in Table I. In Table I, the compounds marked with a superscript 4 do not fall within the limitations set forth in the definition of $R_1$, $R_2$, $R_3$, etc. but they are included because they are similarly useful in the compositions and methods of the present invention. In the tables the numbers preceding the $R_3$, $R_4$ and T definitions indicate the substitutent position in the structure. As used in the Tables herein, Ad=adamantyl; Ph=phenyl; p—ClPh=para-chlorophenyl; Me=methyl; Et=ethyl; Ac=acetyl; Pr=n-propyl; ipr=iso-propyl; $C_6H_{11}$=cyclohexyl; etc. In compounds in which $R_3$ and $R_4$ are joined to form a ring, the structural unit is shown between the columns headed $R_3$ and $R_4$.

TABLE I[a]

COMPOUNDS OF FORMULA I

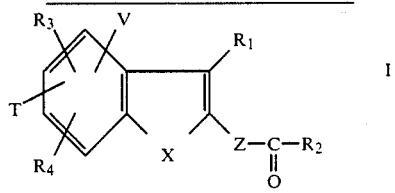

| Compound[b] | X | $R_1$ | $R_2$ | $R_3$ | $R_4$ | T[c] |
|---|---|---|---|---|---|---|
| 1 | O | Me | OEt | 4-OH | 6-Cl | H |
| 2 | O | Me | OCMe$_3$ | 4-OH | 6-Cl | H |
| 3 | O | Me | NH—NH—Ph | 4-OH | 6-Cl | H |
| 4 | O | H | NH—NH—Ph | 4-OH | H | H |
| 5 | O | Me | NH—NH—Ph | 5-OH | H | H |
| 6 | O | Me | NH—NH—Ph | H | 6-OH | H |
| 7 | O | H | OCMe$_3$ | 5-OH | H | H |
| 8 | O | Me | OCMe$_3$ | 6-OH | H | H |
| 9 | O | Me | OCMe$_3$ | 7-OH | H | H |
| 10 | O | Et | OCMe$_3$ | 4-OH | H | H |
| 11 | S | Me | OCMe$_3$ | 4-OH | H | H |
| 12 | S | Me | OEt | 4-OH | 6-OH | H |
| 13 | S | Me | NH—NH—Ph | 4-OH | H | H |
| 14 | O | CH$_2$OH | OEt | 4-OH | H | H |
| 15 | O | CH$_2$Me | OEt | 4-OH | H | H |
| 16 | O | CH$_2$NH$_2$ | OEt | 4-OH | H | H |
| 17 | O | Me | OEt | 4-NHSO$_2$CF$_3$ | H | H |
| 18 | O | Me | OEt | 4-NH$_2$ | H | H |
| 19 | O | CH$_2$CO$_2$H | OEt | 4-OH | H | H |
| 20 | O | Me | OEt | 4-CH$_2$CO$_2$H | H | H |
| 21 | O | Me | OEt | 4-CH$_2$CO$_2$H | 5-OH | H |
| 22 | O | Me | OEt | 5-OH | 4-CH$_2$CO$_2$H | H |
| 23 | O | Me | OEt | 6-OH | 4-SO$_2$—Ph | H |
| 24 | O | Me | N(Me)$_2$ | 4-OH | H | H |
| 25 | O | Ph | OCMe$_3$ | 4-OH | H | H |
| 26 | O | Ph | NH—NH—Ph | 4-OH | H | H |
| 27 | O | Me | OEt | 4-CN | H | H |
| 28 | O | Me | OEt | 4-COMe | H | H |
| 29 | O | Me | OEt | 4-OH | 6-CN | H |
| 30 | O | Me | OEt | 4-OH | 6-Pr | H |
| 31 | SO | iPr | OCMe$_3$ | 4-OH | H | H |
| 32 | SO$_2$ | Ph | OCMe$_3$ | 4-CN | 6-OH | H |
| 33 | O | Me | O—1-Ad | 4-OH | H | H |
| 34 | O | Et | CH$_2$OAc | 4-OH | H | H |
| 35 | O | Me | CH$_2$OH | 4-NO$_2$ | 6-OH | H |
| 36 | O | C$_6$H$_{11}$ | OCMe$_3$ | 4-NHSO$_2$Me | 7-Me | H |
| 49 | O | Me | OCMe$_3$ | 4-OH | 6-CO$_2$Et | H |
| 37 | O | Me | OCMe$_3$ | 4-OH | 5-CH$_2$SMe | 7-Br |

TABLE I-continued

COMPOUNDS OF FORMULA I

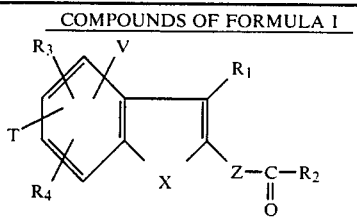

| Compound[b] | X | $R_1$ | $R_2$ | $R_3$ | $R_4$ | T[c] |
|---|---|---|---|---|---|---|
| 38 | S | Me | OCMe₃ | 4-OH | H | H |
| 39 | O | Me | NHNH—Ph | 4-OH | 5-CH₂SMe | 7-Br |
| 40 | O | Me | NHNH—p-ClPh | 4-OH | 5-CH₂SMe | H |
| 41 | O | Me | OEt | 4-O—CSNMe₂ | 5-CF₃ | 7-Cl |
| 42 | O | Me | OEt | 4-S—CONMe₂ | 5-CF₃ | 7-Cl |
| 43 | O | Me | OCH₂—tBu | 4-OH | H | H |
| 44 | O | Me | O—1-Ad | 4-OH | H | H |
| 45 | O | p-ClPh | OEt | 4-OH | H | H |
| 46 | O | p-OCH₃Ph | OEt | 4-OH | H | H |
| 47 | O | p-ClPh | OEt | 6-OH | H | H |
| 48 | O | p-OCH₃Ph | OEt | 6-OH | H | H |
| 49 | O | CH₃ | OEt | 6-OH | 5-Br | H |
| 50 | O | C₆H₅ | NH—Ph | 4-OH | H | H |
| 51 | O | C₆H₅ | NHNH—Ph | 4-OH | H | H |
| 52 | O | C₃H₇ | NH—Ph | 4-OH | H | H |
| 53 | O | C₃H₇ | NHNH—Ph | 4-OH | H | H |
| 54 | O | CH₃ | OEt | 4-NHSO₂CH₃ | H | H |
| 55 | O | CH₃ | OEt | 4-OH | 5-F | H |
| 56 | O | CH₃ | OEt | 5-OH | 4-F | H |
| 57 | O | CH₃ | OEt | 5-NHSO₂CF₃ | H | H |
| 58 | O | CH₃ | OC(CH₃)₃ | 4-OH | 5-COCH₃ | H |
| 59 | O | CH₃ | OC(CH₃)₃ | 4-OH | 7-Br | H |
| 60 | O | CH₃ | OC(CH₃)₃ | 4-OH | 5-NHSO₂CH₃ | H |
| 61 | O | CH₃ | OC(CH₃)₃ | 4-OH | 5-NHSO₂CF₃ | H |
| 62 | S | C₃H₇ | OEt | 4-OH | H | H |
| 63 | S | C₆H₅ | OEt | 4-OH | H | H |
| 64 | S | p-ClPh | OC(CH₃)₃ | 4-OH | H | H |
| 65 | S | p-CH₃—Ph | OC(CH₃)₃ | 4-OH | H | H |
| 66 | O | CH₃ | OEt | 6-OH | 7-COCH₃ | H |
| 67 | O | CH₃ | OEt | 5-OH | 6-COCH₃ | H |
| 68 | O | CH₃ | CH₂CH₂CH₃ | 4-OH | H | H |
| 69 | O | CH₃ | CH₂CH₂CH₃ | 5-OH | H | H |
| 70 | O | CH₃ | CH₂CH₂CH₃ | 6-OH | H | H |
| 71 | O | CH₃ | CH₂CH₂CH₃ | 7-OH | H | H |
| 72 | O | C₃H₇ | CH₂CH₂CH₃ | 4-OH | H | H |
| 73 | O | C₆H₅ | CH₂CH₂CH₃ | 4-OH | H | H |
| 74 | O | CH₃ | CH₂Ph | 4-OH | H | H |
| 75 | O | CH₃ | CH₂CH₂Ph | 4-OH | H | H |
| 76 | O | CH₃ | CH₂—t-Bu | 4-OH | H | H |
| 77 | O | CH₃ | CH₂—C₆H₁₁ | 4-OH | H | H |
| 78 | O | CH₃ | H | 4-OH | H | H |
| 79 | O | CH₃ | OEt | 4-SH | H | H |
| 80 | O | CH₃ | OEt | 4-OH | 5-SCF₃ | H |
| 81 | O | CH₃ | CH₂C(CH₃)₃ | 6-OH | H | H |
| 82 | O | i-Pr | CH₂Ph | 4-OH | 6-Cl | H |
| 83 | O | CH₂Ph | (CH₂)₂Ph | 4-CH₂OH | 5-CF₃ | H |
| 84 | O | Me | CH₂—1-Ad | 4-OH | H | H |
| 85 | O | CH₂Ph | OEt | 4-OH | H | H |
| 86 | O | C₂H₄—pCNPh | OEt | 4-OH | H | H |
| 87 | O | Me | OC(Me)₃ | 4-OH | 5-CH₂SMe | H |
| 88 | O | Me | OC(Me)₃ | 4-OH | 5-CH₂S(O)Me | H |
| 89 | O | Me | OC(Me)₃ | 4-OH | 5-CH₂SO₂Me | H |
| 90 | O | Me | OEt | 4-OH | 5-CF₃ | H |
| 91 | O | CF₃ | OEt | 4-OH | H | H |
| 92 | O | Me | NHNH—p-Cl—Ph | 6-OH | 5-SCF₃ | H |
| 93 | O | i-Pr | OC(Me)₃ | 6-OH | 7-SO₂CF₃ | H |
| 94 | O | Me | OEt | 5-Cl | 6-OH | 7-COPh |
| 95 | O | Me | OH | 5-Br | 6-OH | 7-CH₂Ph |
| 96 | O | Me | OH | 4-OCOPh | 6-OCOPh | 7-Me |
| 97 | O | Me | NHNH₂ | 4-OMe | 6-OMe | 7-Me |
| 98 | O | Me | OEt | 6-OH | 7-CH₂N(Et)₂ | H |
| 99 | O | Ph | NH₂ | 6-OH | H | H |
| 100 | O | Me | OEt | 4-NHAc | 7-OMe | H |
| 101 | O | Me | OMe | 5-Ac | 6-OH | 7-OMe |
| 102 | O | Me | OEt | 5-OH | 6-Ac | H |
| 103 | O | Me | OEt | 4-OAc | 5-Me | H |
| 104 | O | Me | OEt | 4-OAc | 7-Me | H |
| 105 | O | Me | OEt | 5-COCH₂Me | 6-OH | 7-Me |
| 106 | O | Me | OEt | 4-OH | 5-NO₂ | 6-Ph |

TABLE I[a-continued]

COMPOUNDS OF FORMULA I

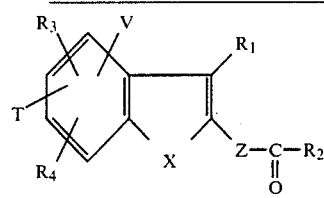

| Compound[b] | X | $R_1$ | $R_2$ | $R_3$ | $R_4$ | T[c] |
|---|---|---|---|---|---|---|
| 107 | O | o-OMePh | OEt | 6-OMe | H | H |
| 108 | O | $CH_2O$—OMePh | OMe | 6-OMe | H | H |
| 109 | O | $CH_2NO_2$ | OEt | 4-OMe | H | H |
| 110 | O | Ph | OEt | 6-OMe | H | H |
| 111 | O | Me | $(CH_2)_2N(Me)_2$ | 5-Br | 6-OMe | H |
| 112 | O | Me | $O(CH_2)_2N(Et)_2$ | 5-Br | 6-OMe | 7-Br |
| 113 | O | Et | OEt | 6-OH | 7-S(O)Me | H |
| 114 | S | Me | OEt | 4-OH | 5-$SCF_3$ | 7-Cl |
| 115 | SO | Me | OEt | 4-OH | 5-S(O)$CF_3$ | 7-Cl |
| 116 | O | Me | NHNH—p-$NO_2$Ph | 6-OH | H | H |
| 117[1,2] | O | $CH_3$ | —NHNHPh | 4-OH | H | H |
| 118[1] | O | $CH_3$ | —NHNHPh—p-OMe | 5-OH | H | H |
| 119[1] | O | $CH_3$ | —NHNHPh—p-OMe | 4-OH | H | H |
| 120[1] | O | $CH_3$ | —NHNHPh—p-OMe | 4-OAc | H | H |
| 121[1] | O | $CH_3$ | —NHNHPh—p-$NO_2$ | 4-OH | H | H |
| 122[1] | O | $CH_3$ | —NHNHPh—p-$NO_2$ | 4-OAc | H | H |
| 123[1] | O | $CH_3$ | H\N—N(piperidine) | 4-OAc | H | H |
| 124[1] | O | $CH_3$ | NHNHPh—p-Cl | 4-OAc | H | H |
| 125[1] | O | $CH_3$ | NHNHPh—p-Cl | 6-OH | H | H |
| 126[1,2] | O | $CH_3$ | NHNHPh—p-Cl | 4-OH | H | H |
| 127[1,2] | O | $CH_3$ | NHNHPh—p-Cl | 4-O—C(O)OMe | H | H |
| 128[1] | O | $CH_3$ | NHNHPh—m-OMe | 4-OH | H | H |
| 129[1] | O | Ph | NHNHPh—p-OMe | 6-OAc | H | H |
| 130[1] | O | $CH_3$ | NHNHPh—p-Cl | 5,6-$OCH_2O$— | | H |
| 131[1] | O | $CH_3$ | NHNHPh—p-Cl | 5-OAc | 6-OAc | H |
| 132[1,2] | O | $CH_3$ | NHNHPh—p-Cl | 5-OH | 6-OH | H |
| 133[1] | O | $CH_3$ | NHNHPh—p-OMe | 4-O—$CH_2CH(OH)CH_3$ | H | H |
| 134[1] | O | $CH_3$ | NHNHPh—p-OMe | 4-O—C(O)OMe | 5-$CH_2SCH_3$ | H |
| 135[1] | O | $CH_3$ | NHNHPh | 4-O—C(O)C($CH_3$)$_3$ | H | H |
| 136[1] | O | Ph | NHNHPh—p-OMe | 6-OH | H | H |
| 137[1] | O | $CH_3$ | NHNHPh—3,4-$Cl_2$ | 4-OH | H | H |
| 138[1,2] | O | $CH_3$ | —NMeNMePh | 4-OH | H | H |
| 139[1] | O | $CH_3$ | —NMeNMePh | 4-OAc | H | H |
| 140[1] | O | $CH_3$ | NHNHPh—3,4-$Cl_2$ | 4-OAc | H | H |

TABLE I[a]-continued
COMPOUNDS OF FORMULA I

| Compound[b] | X | R₁ | R₂ | R₃ | R₄ | T[c] |
|---|---|---|---|---|---|---|
| 141[1] | O | CH₃ | (3,4-dichlorophenyl-NHNH-C(=O)- structure, see figure) | 4-OAc | H | H |
| 142[1] | O | CH₃ | NHNHPh—p-Cl | 5-OAc | H | H |
| 143[1] | O | CH₃ | NHNHPh—p-Cl | 5-OH | H | H |
| 144[1] | O | CH₃ | NHNHPh—m-OMe | 4-OAc | H | H |
| 145[1] | O | CH₃ | NHNHPh | 4-O-C(=O)-OMe | H | H |
| 146[1,2] | O | CH₃ | NHNHPh—p-OMe | 4-OH | 5-Pr | H |
| 147[1] | O | CH₃ | NHNHPh—p-OMe | 4-CH₂CH=CH₂ | 5-OAc | H |
| 148[1] | O | Pr | NHNHPh—p-OMe | 4-O-C(=O)-OMe | H | H |
| 149[1] | O | Pr | NHNHPh—p-OMe | 6-OAc | H | H |
| 150[1] | O | Pr | NHNHPh—p-OMe | 6-OH | H | H |
| 151[1] | O | CH₃ | —NEtNHPh | 4-OAc | H | H |
| 152[1] | O | CH₃ | —NEtNHPh | 4-OH | H | H |
| 153[1] | O | CH₃ | —NHNHPh—p-OMe | 5-O-C(=O)-OMe | H | H |
| 154[1,2] | O | CH₃ | —NHNHPh—p-Cl | 5-O-C(=O)-OMe | H | H |
| 155[1] | O | CH₃ | —NHNHPh—p-OMe | 4-O-C(=O)-OMe | 5-CH₂CH=CH₂ | H |
| 156[1] | O | CH₃ | NMeNMePh | 4-O-C(=O)-OMe | H | H |
| 157[1] | O | CH₃ | NHNHPh—p-Cl | 4-O-C(=O)-OEt | H | H |
| 158[1] | O | CH₃ | NHNHPh—p-OMe | 4-O-C(=O)-OMe | 5-Pr | H |

TABLE I-continued

COMPOUNDS OF FORMULA I

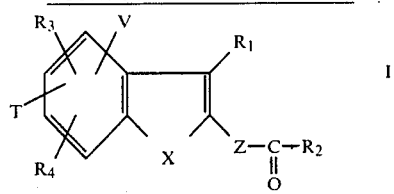

| Compound[b] | X | R1 | R2 | R3 | R4 | T[c] |
|---|---|---|---|---|---|---|
| 159[1] | O | CH3 | NHNHPh—3,4-Cl2 | 4-O-C(=O)-OCH3 | H | H |
| 160[1] | O | CH3 | NHNHPh—p-Cl | 4-O-C(=O)-OCH2CH(CH3)2 | H | H |
| 161[1] | O | CH3 | NHNHPh—p-OMe | 4-O-C(=O)-OMe | H | H |
| 162 | O | CH3 | piperidinyl | 4-OH | H | H |
| 163 | O | CH3 | NHPh | 4-OH | H | H |
| 164 | O | CH3 | NHPh—p-NO2 | 6-OH | H | H |
| 165 | O | CH3 | NHPh—p-OMe | 6-OH | H | H |
| 166 | O | CH3 | NHPh—p-OMe | 4-OH | H | H |
| 167 | O | CH3 | NHPh—p-NO2 | 4-OAc | H | H |
| 168 | O | CH3 | NHPh—p-OMe | 4-OAc | H | H |
| 169 | O | CH3 | NHPh—p-NO2 | 4-OH | H | H |
| 170 | O | CH3 | NH-(4-pyridyl) | 4-OH | H | H |
| 171 | O | CH3 | NHPh | 4-OAc | H | H |
| 172[1] | O | CH3 | OC(CH3)3 | 4-OH | H | H |
| 173 | O | CH3 | NHCH2Ph | 4-OAc | H | H |
| 174 | O | CH3 | NHPh—p-Cl | 4-OAc | H | H |
| 175 | O | CH3 | NH-(3,4-methylenedioxyphenyl) | 4-OAc | H | H |
| 176 | O | CH3 | NH-(3,4-methylenedioxyphenyl) | 4-OH | H | H |
| 177 | O | Pr | NHPh—p-Cl | 6-OH | H | H |
| 178 | O | Ph | NHPh—p-Cl | 6-OAc | H | H |
| 179 | O | CH3 | NHPh | 4-OH | 5-CH2SCH3 | H |
| 180 | O | CH3 | NHPh | 4-O-C(=O)-OCH3 | 5-CH2SCH3 | H |

TABLE I-continued

COMPOUNDS OF FORMULA I

| Compound[b] | X | $R_1$ | $R_2$ | $R_3$ | $R_4$ | T[c] |
|---|---|---|---|---|---|---|
| 181 | O | $CH_3$ |  | 5-OH | H | H |
| 182 | O | Ph | NHPh—p-Cl | 6-OH | H | H |
| 183 | O | $CH_3$ | —NMePh | 4-OAc | H | H |
| 184 | O | $CH_3$ | 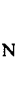 | 4-OH | H | H |
| 185 | O | $CH_3$ | —NMePh | 4-OH | H | H |
| 186 | O | $CH_3$ | NHPh—p-OMe | 4-OH | 5-Pr | H |
| 187 | O | $CH_3$ |  | 4-OAc | H | H |
| 188 | O | Pr | NHPh—p-Cl | 6-OAc | H | H |
| 189 | O | $CH_3$ | NHPh—p-Cl | 4-OH | H | H |
| 190 | O | $CH_3$ | NHPh—p-Cl |  | 5-$CH_2CH=CH_2$ | H |
| 191 | O | $CH_3$ | NHPh—p-OMe |  | 5-Pr | H |
| 192 | O | $CH_3$ | NHPh—p-Cl | 5-OH | H | H |
| 193 | O | Pr | NHPh—p-Cl |  | H | H |
| 194 | O | $CH_3$ | Ph |  | H | H |
| 195 | O | $CH_3$ | $CH_3$ |  | H | H |
| 196 | O | $CH_3$ | $CH_3$ | 4-OH | H | H |
| 197 | O | $CH_3$ | Ph—p-Cl | 4-OH | H | H |
| 198 | O | $CH_3$ | Ph | 6-OH | H | H |
| 199 | O | $CH_3$ | Ph | 4-$OCH_3$ | 6-$OCH_3$ | H |
| 200 | O | $CH_3$ | Ph | 4-OH | 5-Pr | H |
| 201 | O | $CH_3$ | Ph | 4-OH | H | H |
| 202 | O | $CH_3$ | OEt | 4-OH | H | H |
| 203 | O | $CH_3$ | OEt | 4-O-C(=O)-OMe | 5-Pr | H |
| 204 | O | $CH_3$ | OEt | 4-OH | 5-Pr | H |

TABLE I[a]-continued
COMPOUNDS OF FORMULA I

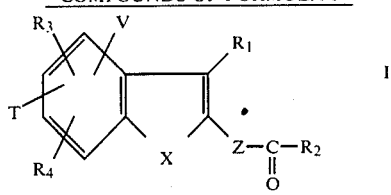

| Compound[b] | X | R$_1$ | R$_2$ | R$_3$ | R$_4$ | T[c] |
|---|---|---|---|---|---|---|
| 205 | O | CH$_3$ | OEt | 4-OCH$_2$CH=CH$_2$ | H | H |
| 206 | O | CH$_3$ | OEt | 4-OH | 5-CH$_2$CH=CH$_2$ | H |
| 207 | O | CH$_3$ | NHNHPh—p-OMe | 4-O-C(=O)-OMe | H | H |
| 208 | O | CH$_3$ | OEt | 4-OH | H | H |
| 209 | O | CH$_3$ | OH | H | 4-OH | H |
| 210 | O | CH$_3$ | NHNHPh—p-OMe | 4-OH | H | H |
| 211 | O | CH$_3$ | OEt | 4-OH | H | H |
| 212 | O | CH$_3$ | OH | H | 4-OH | H |
| 213[1] | O | Me | OEt | 4-OH | 5-CH$_2$SCH$_2$Ph | H |
| 214[1] | O | Me | OEt | 4-OH | 5-CH$_2$SCH$_2$CO$_2$H | H |
| 215[4] | O | Me | OEt | 4-O,5-O-B(Ph) (cyclic boronate) | | H |
| 216 | O | Me | OEt | 4-OH | 5-CH$_2$OH | H |
| 217 | O | Me | OEt | 5-OAc | H | H |
| 218 | O | Me | OEt | 4-OH | 5-CH$_2$OEt | H |
| 219[1] | O | Me | OEt | 4-OH | 5-CH$_2$SEt | H |
| 220[1] | O | Me | OEt | 4-OH | 5-CH$_2$SBu | H |
| 221[1,2] | O | Me | OEt | 4-OH | 5-CH$_2$SMe | H |
| 223[1] | O | Me | OCH$_2$Ph—p-OMe | 4-O-C(=O)-OCH$_3$ | H | H |
| 224[1] | O | Me | OCH$_2$Ph—p-Cl | 4-O-C(=O)-OCH$_3$ | H | H |
| 225 | O | Me | OEt | 4-OCH$_2$CH=CH$_2$ | H | H |
| 226 | O | Me | OEt | 4-O-CH$_2$-C(=O)-CH$_3$ | H | H |
| 227 | O | Me | O-cyclohexyl | 4-OAc | H | H |
| 228[1,2] | O | Me | OEt | 4-O-C(=O)-OMe | 5-CH$_2$SCH$_3$ | H |
| 229 | O | Pr | OEt | 4-OCH$_2$CH=CH$_2$ | H | H |
| 230 | O | Me | OMe | 4-O-C(=O)-OMe | 5-CH$_2$CH=CH$_2$ | H |
| 231[1,2] | O | Me | OEt | 4-O-C(=O)-OMe | 5-Pr | H |

TABLE I-continued
COMPOUNDS OF FORMULA I

| Compound[b] | X | R$_1$ | R$_2$ | R$_3$ | R$_4$ | T[c] |
|---|---|---|---|---|---|---|
| 232[1] | O | Me | OCH$_2$Ph—3,4-Cl$_2$ | 4-O-C(=O)-OMe | H | H |
| 233[1] | O | Me | OCH$_2$Ph—3,4-Cl$_2$ | 4-OAc | | H |
| 234[1] | O | Me | OCH$_2$Ph | 4-O-C(=O)-OMe | 5-CH$_2$CH=CH$_2$ | H |
| 235[1] | O | Me | OCH$_2$Ph | 4-O-C(=O)-OPh | H | H |
| 236 | O | Me | OEt | 5-OCH$_2$CH=CH$_2$ | H | H |
| 237 | O | Me | OEt | 4-OMe | 7-Pr | H |
| 238[1,2] | O | Me | OEt | 5-O-C(=O)-OMe | 6-O-C(=O)-OMe | H |
| 239[1] | O | Me | —OCH$_2$Ph—p-Cl | 4-OAc | H | H |
| 240[1] | O | Me | OCH$_2$Ph | 4-OAc | H | H |
| 241 | O | Me | OEt | 5-OH | 4-CH$_2$CH=CH$_2$ | H |
| 242 | O | Me | OEt | 4-OH | 5-CH$_2$CH=CH$_2$ | H |
| 243 | O | Me | OEt | 6-S-C(=O)-N(CH$_3$)$_2$ | H | H |
| 244 | O | Me | OEt | 4-S-C(=O)-N(CH$_3$)$_2$ | H | H |
| 245 | O | Ph | OEt | 6-OH | H | H |
| 246 | O | Me | OEt | 5-NHAc | H | H |
| 247[4] | O | Me | OEt | 4-O-CH(CO$_2$Et)-C(=O)CH$_3$ | H | H |
| 248 | O | Me | OEt | 5-OH | 6-OMe | H |
| 249 | O | Me | OEt | 5,6-OCH$_2$O— | | H |
| 250 | O | Pr | OEt | 4-OH | H | H |
| 251 | O | Me | OEt | 4-OH | 6-OMe | H |
| 252 | O | Me | OEt | 4-OH | 5-Pr | H |
| 253 | O | Ph | OEt | 4-OH | H | H |
| 254 | O | Ph | OEt | 4-OH | 5-C(=O)Ph | H |
| 255[1,2] | O | Me | O—CH$_2$Ph | 4-OH | H | H |
| 256[1] | O | Me | OCH$_2$Ph—3,4-Cl$_2$ | 4-OH | H | H |
| 257 | O | Me | OCH$_2$Ph—p-Cl | 4-OH | H | H |
| 258[1] | O | Me | OCH$_2$Ph—p-OMe | 4-OH | H | H |

TABLE I-continued

COMPOUNDS OF FORMULA I

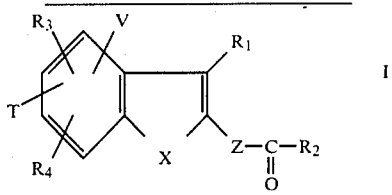

| Compound[b] | X | R₁ | R₂ | R₃ | R₄ | T[c] |
|---|---|---|---|---|---|---|
| 259 | O | Me | (cyclohexyloxy) | 4-OH | H | H |
| 260 | O | CH₃ | OH | 4-O-CH₂-CH(OH)-CH₃ | H | H |
| 261 | O | CH₃ | OH | 4-OH | 5-Pr | H |
| 262 | O | CH₃ | OH | 5,6-OCH₂O— | | H |
| 263 | O | Me | (methylenedioxy-methyl group) | 4-OH | H | H |
| 264 | O | Me | OEt | 4-OH | 5-OH | H |
| 265 | O | Me | OEt | 4-OH | 7-OH | H |
| 266 | O | Me | OEt | 4-O-CH₂-CH(OH)-CH₃ | H | H |
| 267 | O | CH₃ | Ph—p-OMe | 4-OH | 5-Pr | H |
| 268 | O | CH₃ | 4-pyridyl | 4-OH | 5-Pr | H |
| 269 | O | CH₃ | —NMeNMePh—p-F | 5-OH | 6-OH | H |
| 270 | O | CH₃ | —NHNMePh—p-F | 5-OH | 6-OH | H |
| 271 | O | CH₃ | —NHNMePh—p-Cl | 5-OH | 6-OH | H |
| 272 | O | CH₃ | —NHNMePh—p-Cl | 5-OH | 6-OH | H |
| 273 | O | CH₃ | —NHNMePh—p-F | 4-OH | H | H |
| 274 | O | CH₃ | —NMeNMePh—p-F | 4-OH | H | H |
| 275 | O | CH₃ | —OCH₂Ph—p-F | 5-OH | 6-OH | H |
| 276 | O | CH₃ | —OCH₂Ph—p-Cl | 5-OH | 6-OH | H |
| 277 | O | CH₃ | —OCH₂Ph—p-OCH₃ | 5-OH | 6-OH | H |
| 278 | O | CH₃ | 5-amino-tetrazolyl | 4-OH | H | H |
| 279 | O | CH₃ | —NHNMePh—p-CF₃ | 4-OH | H | H |
| 280 | O | CH₃ | —OCH₂Ph | 4-OH | 5-CH₂SCH₃ | H |
| 281 | O | Ph | OEt | 4-OH | 5-CH₂Ph | H |
| 282 | O | CH₃ | OEt | 4-OH | 5-CH₂CO₂Et | H |
| 283 | O | CH₃ | —CH=CHPh | 4-OH | 5-Pr | H |
| 284 | O | CH₃ | —NHNMePh—p-F | 4-OH | 5-CH₂SCH₃ | H |
| 285 | O | CH₃ | —NHNMePh—p-F | 4-OH | 5-Pr | H |
| 286 | O | CH₃ | —NHNMePH—p-F | 5-OH | H | H |
| 287[1] | O | CH₃ | —NHNMePh | 4-OH | H | H |

TABLE I-continued

COMPOUNDS OF FORMULA I

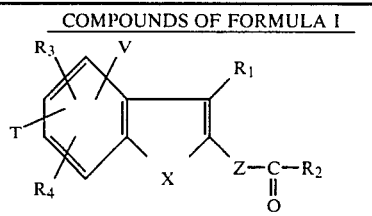

| Compound[b] | X | R$_1$ | R$_2$ | R$_3$ | R$_4$ | T[c] |
|---|---|---|---|---|---|---|
| 288[1,2] | O | CH$_3$ | —OEt | 4-O-C(=O)-OMe | H | H |
| 289[1,2] | O | CH$_3$ | —OEt | 5-OH | 6-OH | H |
| 290[1] | O | CH$_3$ | —OCH$_2$—Ph—p-OMe | 4-OAc | H | H |
| 291 | O | CH$_3$ | —NMeNMePh—p-CF$_3$ | 4-OH | H | H |
| 292 | O | CH$_3$ | —OCH$_2$Ph | 4-OH | 7-OH | H |
| 293 | O | CH$_3$ | —OCH$_2$Ph | 4-OAc | 7-OAc | H |
| 294 | O | CH$_3$ | —OCH$_2$Ph | 4-OH | 7-OH | 5-CH$_2$CH$_2$CH$_3$ |
| 295 | O | CH$_3$ | —OCH$_2$Ph | 4-OAc | 7-OAc | 5-CH$_2$CH$_2$CH$_3$ |
| 296 | O | CH$_3$ | —NHNH—Ph | 4-OH | 7-OH | H |
| 297 | O | CH$_3$ | —NHNH—Ph | 4-OAc | 7-OAc | H |
| 298 | O | CH$_3$ | —NHNH—Ph | 4-OH | 7-OH | 5-CH$_2$CH$_2$CH$_3$ |
| 299 | O | CH$_3$ | —NHNH—Ph | 4-OAc | 7-OAc | H |
| 300 | O | CH$_3$ | OEt | H | H | c |
| 301 | O | CH$_3$ | OEt | 5-OH | H | c |
| 302 | O | CH$_3$ | OEt | H | 6-OH | c |
| 303 | O | CH$_3$ | OEt | 5-OCH$_3$ | H | c |
| 304 | O | CH$_3$ | OEt | H | 6-OCH$_3$ | c |
| 305[1,2] | O | CH$_3$ | OEt | 5-Cl | 6-OH | c |
| 306 | O | CH$_3$ | OEt | 5-Cl | 6-OCH$_3$ | c |
| 307[1,2] | O | CH$_3$ | OEt | 5-COCH$_3$ | H | c |
| 308 | O | CH$_3$ | OEt | 5-Cl | 6-Cl | c |
| 309 | O | CH$_3$ | OEt | 5-CH$_2$CH=CH$_2$ | H | c |
| 310[1,2] | O | CH$_3$ | OEt | 5-CH$_2$CH$_2$CH$_3$ | H | c |
| 311[1,2] | O | CH$_3$ | OEt | 5-CH$_2$SCH$_3$ | H | c |
| 312 | O | CH$_3$ | OEt | 5-CH$_2$SBu[n] | H | c |
| 313[1,2] | O | CH$_3$ | OEt | 5-OH | 6-OH | c |
| 314[1,2] | O | CH$_3$ | OEt | 5-OCH$_3$ | 6-OCH$_3$ | c |
| 315[1,2] | O | CH$_3$ | OEt | 5-CH$_3$ | 6-CH$_3$ | c |
| 316 | O | CH$_3$ | OEt | 5-C$_2$H$_5$ | 6-C$_2$H$_5$ | c |
| 317[1,2] | O | CH$_3$ | OEt | 5,6-O—CH$_2$—O | | c |
| 318 | O | CH$_3$ | OEt | 5-Cl | H | c |
| 319 | O | CH$_3$ | OEt | 5-OH | 6-OCH$_3$ | c |
| 320 | O | CH$_3$ | OEt | 5-OCH$_3$ | 6-OH | c |
| 321 | O | CH$_3$ | OEt | 5-CH$_2$OC$_2$H$_5$ | H | c |
| 322 | O | CH$_3$ | OEt | 5-NHCOCH$_3$ | H | c |
| 323 | O | CH$_3$ | OEt | H | H | c |
| 324[1,2] | O | CH$_3$ | OEt | 5,6-O—CH$_2$—O | | c |
| 325[1,2] | O | CH$_3$ | OEt | 5-OCH$_3$ | 6-OCH$_3$ | c |
| 326[1,2] | O | CH$_3$ | OEt | 5-CH$_3$ | 6-CH$_3$ | c |
| 327 | O | CH$_3$ | OEt | 5-Cl | H | c |
| 328 | O | CH$_3$ | OEt | 5-CH$_2$CH=CH$_2$ | H | c |
| 329 | O | CH$_3$ | OEt | 5-CH$_2$CH$_2$CH$_3$ | H | c |
| 330 | O | CH$_3$ | OEt | 5-OH | 6-OH | c |
| 331[1,2] | O | CH$_3$ | OEt | 5-CH$_2$OC$_2$H$_5$ | H | c |
| 332 | O | CH$_3$ | OEt | 5-CH$_2$SCH$_3$ | H | c |
| 333[1,2] | O | CH$_3$ | OCH$_2$Ph | H | H | c |
| 334 | O | CH$_3$ | OCH$_2$Ph—p-OMe | H | H | c |
| 335 | O | CH$_3$ | OCH$_2$Ph—p-Cl | H | H | c |
| 336 | O | CH$_3$ | NHNHPh | H | H | c |
| 337[1,2] | O | CH$_3$ | NHNHPh—p-Cl | H | H | c |
| 338 | O | CH$_3$ | NHNHPh—p-OMe | H | H | c |
| 339[1,2] | O | CH$_3$ | NHNHPh—p-OMe | 5-CH$_2$SCH$_3$ | H | c |
| 340[1,2] | O | CH$_3$ | NHNHPh—p-OMe | 5-CH$_2$CH$_2$CH$_3$ | H | c |
| 341 | O | CH$_3$ | NHNHphe | 5-OCH$_3$ | H | c |
| 342 | O | CH$_3$ | NHNHPh | 5-OH | H | c |
| 343 | O | CH$_3$ | NHNHPh | 5-CH$_2$SCH$_3$ | H | c |
| 344 | O | CH$_3$ | NHNHPh—p-OMe | H | 6-OCH$_3$ | c |
| 345 | O | CH$_3$ | NHNHPh—p-OMe | 5,6-O—CH$_2$—O | | c |
| 346 | O | CH$_3$ | NHNHPh—p-OMe | 5-OCH$_3$ | 6-OCH$_3$ | c |
| 347 | O | CH$_3$ | NHNHPh—p-OMe | 5-CH$_3$ | 6-CH$_3$ | c |
| 348 | O | CH$_3$ | NHPh | H | H | c |
| 349 | O | CH$_3$ | NHPh—p-Cl | H | H | c |
| 350 | O | CH$_3$ | NHPh—3,4-OCH$_2$O | H | H | c |
| 351 | O | CH$_3$ | NHPh—p-OMe | H | H | c |
| 352 | O | CH$_3$ | NHPh | 5-CH$_2$SCH$_3$ | H | c |

TABLE I[a-continued]

COMPOUNDS OF FORMULA I

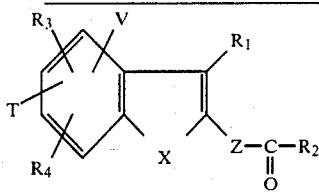

I

| Compound[b] | X | $R_1$ | $R_2$ | $R_3$ | $R_4$ | $T^c$ |
|---|---|---|---|---|---|---|
| 353 | O | $CH_3$ | NMePh | H | H | c |
| 354 | O | $CH_3$ | NHPh—p-OMe | 5-$CH_2CH_2CH_3$ | H | c |
| 355 | O | $CH_3$ | NH—4-$C_5H_4N$ | H | H | c |
| 356 | O | $CH_3$ | NH—Ph—p-OMe | H | 6-OH | c |
| 357 | O | $CH_3$ | NH—Ph—p-OMe | H | 6-$OCH_3$ | c |
| 358 | O | $CH_3$ | NH—Ph—p-Cl | 5,6-O—$CH_2$—O | | c |
| 359 | O | $CH_3$ | NH—Ph—p-Cl | 5-$OCH_3$ | 6-$OCH_3$ | c |
| 360 | O | $CH_3$ | NH—Ph—p-Cl | 5-$CH_3$ | 6-$CH_3$ | c |
| 361 | O | $CH_3$ | OH | H | H | c |
| 362 | O | $CH_3$ | OH | 5-$CH_2CH_2CH_3$ | H | c |
| 364[1,2] | O | $CH_3$ | $OCH_2Ph$ | 5-$CH_2CH_2CH_3$ | H | c |
| 365 | O | $CH_3$ | NHNHPh | 5-$CH_2CH_2CH_3$ | H | c |
| 366 | O | $CH_3$ | OEt | 4-OH | 5-$CH_2CH_2CH_3$ | 7-F |
| 367 | O | $CH_3$ | OEt | 4-OH | 5-$CH_2CH_2CH_3$ | 7-Cl |
| 368 | O | $CH_3$ | $OCH_2Ph$ | 4-OH | 5-$CH_2CH_2CH_3$ | 7-F |
| 369 | O | $CH_3$ | $OCH_2Ph$ | 4-OH | 5-$CH_2CH_2CH_3$ | 7-Cl |

[a]A Superscript 1 indicates preferred compounds and a superscript 2 indicates the more preferred compounds.
[b]In compound 202, Z is —CMe=CH—; in compounds 203 to 210 and 323 to 332, Z is —CH=CH—; in compounds 211 and 212, Z is —$CH_2CH_2$—; in all others Z is a bond.
[c]In compounds 1 to 299, V is H; in compounds 300 to 365 T and V are located at positions 4 and 7 respectively and are both simultaneously OH, $OCOCH_3$ or $OCO_2CH_3$.

The Formula I compounds are potent inhibitors of the 5-lipoxygenase pathway of arachidonic acid metabolism and have little or no inhibiting effect on the cyclooxygenase pathway of arachidonic acid metabolism.

The compounds of Formula I are active as inhibitors of the biosynthesis of both leukotriene $B_4$, as well as leukotrienes $C_4$, $D_4$, $E_4$ and $F_4$, the active elements of slow reacting substance of anaphylaxis (SRS-A). This inhibition of the biosynthesis of leukotrienes indicates that the compositions are useful to treat, prevent or ameliorate, in mammals and especially in humans, pulmonary conditions including diseases such as asthma; and allergies and allergic reactions such as allergic rhinitis, contact dermatitis, and allergic conjunctivitis. These compounds are also useful in mammals, especially in humans, as anti-inflammatory and analgesic agents; and in the treatment of skin diseases, such as psoriasis; and in the treatment of cardiovascular conditions, such as angina; and as cytoprotective agents.

The cytoprotective activity of a compound may be observed in both animals and man by noting the increased resistance of the gastrointestinal mucosa to the noxious effects of strong irritants, for example, the ulcerogenic effects of aspirin or indomethacin. In addition to lessening the effect of non-steroidal anti-inflammatory drugs on the gastrointestinal tract, animal studies show that cytoprotective compounds will prevent gastric lesions induced by oral administration of strong acids, strong bases, ethanol, hypertonic saline solutions and the like.

Two assays can be used to measure cytoprotective ability. These assays are; (A) an ethanol-induced gastric ulcer assay and (B) an indomethacin-induced ulcer assay.

A. Ethanol-Induced Gastric Ulcer

Twenty-four fasted Sprague-Dawley (S.D.) rats are perorally (p.o.) dosed with 1.0 ml absolute ethanol. Fifteen minutes prior to ethanol administration, groups of rats each receive either an aqueous vehicle (aqueous methylcellulose 5% wt.) or the test compound at various doses perorally. One hour later, the animals are sacrificed and stomach mucosae are examined for resulting lesions.

B. Indomethacin-Induced Ulcer Assay

Indomethacin, 10 mg/kg p.o., is used to induce ulcers in 24 hour fasted S.D. rats. Fifteen minutes prior to indomethacin administration, groups of rats each receive either an aqueous vehicle (5% by weight methylcellulose) or the test compound at various doses perorally. Four hours later the animals are sacrificed and stomach mucosae are examined for resulting ulcers.

The magnitude of a prophylactic or therapeutic dose of a compound of formula I will, of course, vary with the nature of the severity of the condition to be treated and with the particular compound of formula I and its route of administration. In general, the daily dose range for anti-asthmatic, anti-allergic or anti-inflammatory use and, generally uses other than cytoprotection, lies within the range of from about 10 μg to about 20 mg per kg body weight of a mammal, preferably from about 50 μg to about 20 mg per kg of body weight of a mammal, and most preferably from about 100 μg to about 10 mg per kg of body weight of a mammal.

The exact amount of a compound of the Formula I to be used as a cytoprotective agent will depend on, inter alia, whether it is being administered to heal damaged cells or to avoid future damage, on the nature of the damaged cells (e.g., gastro-intestinal ulcerations vs. nephrotic necrosis), and on the nature of the causative agent. An example of the use of a compound of the Formula I in avoiding future damage would be co-administration of a compound of the Formula I with a non-steroidal anti-inflammatory drug (for example, indomethacin) that might otherwise cause such damage.

For such use, the compound of Formula I is administered from 30 minutes prior up to 30 minutes after administration of the NSAID. Preferably, it is administered prior to or simultaneously with the NSAID (e.g. as a combination dosage form).

The effective daily dosage level for compounds of Formula I inducing cytoprotection in mammals, especially humans, will generally range from about 0.002 mg/kg to about 100 mg/kg, preferably from about 0.02 mg/kg to about 30 mg/kg. The dosage may be administered in single or divided individual doses.

Any suitable route of administration may be employed for providing a mammal, especially a human with an effective dosage of a leukotriene antagonist. For example, oral, rectal, tansdermal, parenteral, intramuscular, intravenous and the like may be employed. Dosage forms include tablets, troches, dispersions, suspensions, solutions, capsules and the like.

The pharmaceutical compositions of the present invention comprise a compound of formula I as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases including inorganic bases and organic bases. Salts derived frm inorganic bases include sodium, potassium, lithium, ammonium, calcium, magnesium, ferrous, zinc, copper, manganous, aluminum, ferric, manganic salts and the like. Particularly preferred are the ammonium, potassium, sodium, calcium and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, 2-diethylaminoethanol, tromethamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like.

The compositions include compositions suitable for oral, rectal, ophthalmic, pulmonary, nasal, dermal, topical or parenteral (including subcutaneous, intramuscular and intravenous) administration, although the most suitable route in any given case will depend on the nature and severity of the conditions being treated and on the nature of the active ingredient. They may be conveniently presented in unit dosage form and prepared by any of the methods well-known in the art of pharmacy.

For use where a composition for intravenous administration is employed, a suitable dosage range for anti-asthmatic, anti-inflammatory or anti-allergic use is from about 0.01 to about 20 mg (preferably from about 0.1 to about 10 mg) of a compound of formula I per kg of body weight per day and for cytoprotective use from about 0.002 mg to about 100 mg (preferably from about 0.02 mg to about 30 mg and more preferably from about 0.1 mg to about 10 mg) of a compound of Formula I per kg of body weight per day. In the case where an oral composition is employed, a suitable dosage range for anti-asthmatic, antiinflammatory, or anti-allergic use is, e.g. from about 1 to about 100 mg of a compound of formula I per kg of body weight per day, preferably from about 5 to about 40 mg per kg and for cytoprotective use from about 0.01 mg to about 30 mg (preferably from about 0.1 mg to about 10 mg of a compound of Formula I per kg of body weight per day.

The topical application dosage forms include ointments, salves, controlled release patches, emulsions, solutions, thixotropic formulations, powders sprays and the like. For topical application, the percent by weight of the active ingredient (Formula I compound) may vary from about 0.001 to about 10%.

For treating inflammation the mode of administration may be oral, parenteral, by suppository and the like. The various dosage forms are the same as those described above.

For treating skin diseases such as psoriasis, atopic dermatitis and the like, oral topical or parenteral administration is useful. For topical application to the diseased area, salves, patches, controlled release patches, emulsions, etc., are convenient dosage forms.

For use as an analgesic, i.e. for treating pain, any suitable mode of administration may be used, e.g., oral, parenteral, by insufflation, by suppository and the like.

For treating cardiovascular conditions, such as angina pectoris, etc., any suitable mode of administration, e.g. oral, parenteral, topical, insufflation, etc. and dosage form e.g. pills, liquid formulations, controlled release capsules, controlled release skin patches, etc. may be used.

For administration by inhalation, the compounds of the present invention are conveniently delivered in the form of an aerosol spray presentation from pressurized packs or a nebuliser. The preferred composition for inhalation is a powder which may be formulated as a cartridge from which the powder composition may be inhaled with the aid of a suitable device. In the case of a pressurized aerosol, the dosage unit may be determined by providing a valve to deliver a metered amount. These inhalation formulations will range in dosage from about 0.1 $\mu$g to about 200 $\mu$g of a compound of Formula I, administered as necessary to provide relief.

In practical use, leukotriene antagonists of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or intravenous. In preparing the compositions for oral dosage form, any of the usual pharmaceutical media may be employed, such as, for example, water glycols, oils, alcohols, flavoring agents, preservatives, coloring agents and the like in the case of oral liquid preparations, such as, for example, suspensions, elixirs and solutions; or carriers such as starches, sugars, diluents, granulating agents, lubricants, binders, disintegrating agents and the like in the case of oral solid preparations such as, for example, powders, capsules and tablets. Because of their ease of administration, tablets and capsules represent the most advantageous oral dosage unit form, in which case solid pharmaceutical carriers are obviously employed. If desired, tablets may be sugar coated or enteric coated by standard techniques.

In addition to the common dosage forms set out above, the leukotriene antagonists of Formula I may also be administered by controlled release means and/or delivery devices such as those described in U.S. Pat. Nos. 3,845,770; 3,916,899; 3,536,809; 3,598,123;

3,630,200 and 4,008,719, the disclosure of whcih is hereby incorporated herein by reference.

Pharmaceutical compositions of the present invention suitable for oral administration and by inhalation in the case of asthma therapy may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, lubricating, surface active or dispersing agent. Molded tablets may be made by molding in a suitable machine, a mixture of the powdered compound moistened with an inert liquid diluent. Desirably, each tablet contains from about 25 mg to about 500 mg of the active ingredient and each cachet or capsule contains from about 25 to about 500 mg of the active ingredient.

The following are examples of representative pharmaceutical dosage forms for the compounds of Formula I:

| Injectable Suspension | mg/ml |
|---|---|
| Leukotriene inhibitor | 2 |
| Methylcellulose | 5.0 |
| Tween 80 | 0.5 |
| Benzyl alcohol | 9.0 |
| Methyl paraben | 1.8 |
| Propyl paraben | 0.2 |
| Water for injection to a total volume of 10 ml | |

| Tablet | mg/tablet |
|---|---|
| Leukotriene inhibitor | 25 |
| Microcrystalline Cellulose | 415 |
| Povidone | 14.0 |
| Pregelatinized Starch | 43.5 |
| Magnesium Stearate | 2.5 |
| | 500 |

| Capsule | mg/capsule |
|---|---|
| Leukotriene inhibitor | 25 |
| Lactose Powder | 573.5 |
| Magnesium Stearate | 1.5 |
| | 600 |

In addition to the compounds of Formula I, the pharmaceutical compositions can also contain other active ingredients, such as cyclooxygenase inhibitors, non-steroidal anti-inflammatory drugs (NSAIDs), peripheral analgesic agents such as zomepirac, diflunisal and the like. The weight ratio of the compound of the Formula I to the second active ingredient may be varied and will depend upon the effective dose of each ingredient. Generally, an effective dose of each will be used. Thus, for example, when a compound of the Formula I is combined with an NSAID, the weight ratio of the compound of the Formula I to the NSAID will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

Combinations of a compound of the Formula I and other active ingredients will generally be in the aforementioned ratios.

NSAIDs can be characterized into five groups:
(1) the propionic acid derivatives;
(2) the acetic acid derivatives;
(3) the fenamic acid derivatives;
(4) the biphenylcarboxylic acid derivatives; and
(5) the oxicams
or a pharmaceutically acceptable salt thereof.

The propionic acid derivatives which may be used comprise: ibuprofen, ibuprufen aluminum, indoprofen, ketoprofen, naproxen, benoxaprofen, flurbiprofen, fenoprofen, fenbufen, ketoprofen, indoprofen, pirprofen, carprofen, oxaprozin, pranoprofen, miroprofen, tioxaprofen, suprofen, alminoprofen, tiaprofenic acid, fluprofen and bucloxic acid. Structurally related propionic acid derivatives having similar analgesic and anti-inflammatory properties are also intended to be included in this group.

Thus, "propionic acid derivatives" as defined herein are non-narcotic analgesics/non-steroidal anti-inflammatory drugs having a free —CH(CH$_3$)COOH or —CH$_2$CH$_2$COOH group (which optionally can be in the form of a pharmaceutically acceptable salt group, e.g., —CH(CH$_3$)COO$^-$Na$^+$ or —CH$_2$CH$_2$COO$^-$Na$^+$), typically attached directly or via a carbonyl function to a ring system, preferably to an aromatic ring system.

The acetic acid derivatives which may be used comprise: indomethacin, which is a preferred NSAID, sulindac, tolmetin, zomepirac, diclofenac, fenclofenac, alclofenac, ibufenac, isoxepac, furofenac, tiopinac, zidometacin, acemetacin, fentiazac, clidanac, oxpinac, and fenclozic acid. Structurally related acetic acid derivatives having similar analgesic and antiinflammatory properties are also intended to be encompassed by this group.

Thus, "acetic acid derivatives" as defined herein are non-narcotic analgesics/non-steroidal anti-inflammatory drugs having a free —CH$_2$COOH group (which optionally can be in the form of a pharmaceutically acceptable salt group, e.g. —CH$_2$COO$^-$Na$^+$), typically attached directly to a ring system, preferably to an aromatic or heteroaromatic ring system.

The fenamic acid derivatives which may be used comprise: mefenamic acid, meclofenamic acid, flufenamic acid; niflumic acid and tolfenamic acid. Structurally related fenamic acid derivatives having similar analgesic and anti-inflammatory properties are also intended to be encompassed by this group.

Thus, "fenamic acid derivatives" as defined herein are non-narcotic analgesics/non-steroidal anti-inflammatory drugs which contain the basic structure:

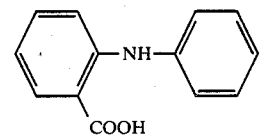

which can bear a variety of substituents and in which the free —COOH group can be in the form of a pharmaceutically acceptable salt group, e.g., —COO⁻Na⁺.

The biphenylcarboxylic acid derivatives which can be used comprise: diflunisal and flufenisal. Structurally related biphenylcarboxylic acid derivatives having similar analgesic and anti-inflammatory properties are also intended to be encompassed by this group.

Thus, "biphenylcarboxylic acid derivatives" as defined herein are non-narcotic analgesics/non-steroidal anti-inflammatory drugs which contain the basic structure:

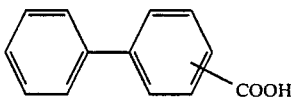

which can bear a variety of substituents and in which the free —COOH group can be in the form of a pharmaceutically acceptable salt group, e.g., —COO⁻Na⁺.

The oxicams which can be used in the present invention comprise: piroxicam, sudoxicam, isoxicam and 4-hydroxyl-1,2-benzothiazine 1,1-dioxide 4-(N-phenyl)-carboxamide. Structurally related oxicams having similar analgesic and anti-inflammatory properties are also intended to be encompassed by this group.

Thus, "oxicams" as defined herein are non-narcotic analgesics/non-steroidal anti-inflammatory drugs which have the general formula:

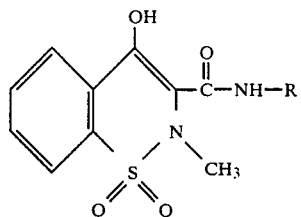

wherein R is an aryl or heteroaryl ring system.

The following NSAIDs may also be used: acemetacin, alminoprofen, amfenac sodium, aminoprofen, anitrazafen, antrafenine, auranofin, bendazac lysinate, benzydamine, beprozin, broperamole, bufezolac, carprofen, cinmetacin, ciproquazone, clidanac, cloximate, dazidamine, deboxamet, delmetacin, detomidine, dexindoprofen, diacerein, di-fisalamine, difenpyramide, emorfazone, enfenamic acid, enolicam, epirizole, etersalate, etodolac, etofenamate, fanetizole mesylate, fenclofenac, fenclorac, fendosal, fenflumizole, fentiazac, feprazone, floctafenine, flunixin, flunoxaprofen, fluproquazine, fopirtoline, fosfosal, furcloprofen, furofenac, glucametacin, guaimesal, ibuproxam, isofezolac, isonixim, isoprofen, isoxepac, isoxicam, lefetamine HCl, leflunomide, lofemizole, lonazolac calcium, lotifazole, loxoprofen, lysin clonixinate, meclofenamate sodium, meseclazone, miroprofen, nabumetone, nictindole, nimesulide, orpanoxin, oxametacin, oxapadol, oxaprozin, perisoxal citrate, pimeprofen, pimetacin, piproxen, pirazolac, pirfenidone, pirprofen, proanoprofen, proglumetacin maleate, proquazone, pyridoxiprofen, sodoxicam, suprofen, talmetacin, talniflumate, tenoxicam, thiazolinobutazone, thielavin B, tiaprofenic acid, tiaramide HCl, tiflamizole, timegadine, tioxaprofen, tolfenamic acid, tolpadol, tryptamid, ufenamate, and zidometacin.

The following NSAIDs, designated by company code number, may also be used: 480156S, AA861, AD1491, AD1590, AFP802, AFP860, AHR6293, AI77B, AP504, AU8001, BAYo8276, BPPC, BW540C, BW755C, CHINOIN 127, CN100, CO893XX, CPP, D10242, DKA9, DV17, EB382, EGYT2829, EL508, F1044, FZ, GP53633, GP650, GV3658, HG/3, ITCl, ITF, ITF182, KB1043, KC8973, KCNTEI6090, KME4, LA2851, LT696, LU20884, M7074, MED15, MG18311, MR714, MR897, MY309, NO164, ONO3144, PR823, PV102, PV108, QZ16, R830, RS2131, RU16029, RU26559, RUB265, SCR152, SH440, SIR133, SIR136, SIR92, SPAS510, SQ27239, ST281, SX1032, SY6001, SaH46798, TA60, TAI901, TEI615, TVX2706, TVX960, TZI615, U60257, UR2310, WY23205, WY41770, YM09561, YM13162, YS1033, and ZK31945.

Finally, NSAIDs which may also be used include the salicylates, specifically aspirin, and the phenylbutazones, and pharmaceutically acceptable salts thereof.

Pharmaceutical compositions comprising the Formula I compounds may also contain inhibitors of the biosynthesis of the leukotrienes such as are disclosed in pending U.S. patent applications Ser. No. 654,991, filed Sept. 26, 1984, Ser. No. 591,134, filed Mar. 19, 1984, Ser. No. 716,878, filed Mar. 8, 1985, and Ser. No. 660,595, filed Dec. 11, 1984, which are hereby incorporated herein by reference.

The compounds of the Formula I may also be used in combination with leukotriene antagonists such as those disclosed in copending applications U.S. Ser. Nos. 591,345 and 591,346, filed Mar. 19, 1984 which are hereby incorporated herein by reference and others known in the art such as those disclosed in European Patent Application Nos. 56,172 and 61,800; and in U.K. Patent Specification No. 2,058,785, which are hereby incorporated herein by reference.

Pharmaceutical compositions comprising the Formula I compounds may also contain as the second active ingredient, antihistaminic agents such as benadryl, dramamine, histadyl, phenergan and the like. Alternatively, they may include prostaglandin antagonists such as those disclosed in European Patent Application No. 11,067 or thromboxane antagonists such as those disclosed in U.S. Pat. No. 4,237,160. They may also contain histidine decarboxyase inhibitors such as α-fluoromethylhistadine, described in U.S. Pat. No. 4,325,961. The compounds of the Formula I may also be advantageously combined with an $H_1$ or $H_2$-receptor antagonist, such as for instance cimetidine, ranitidine, terfenadine, famotidine, aminothiadiazoles disclosed in EP No. 81102976.8 and like compounds, such as those disclosed in U.S. Pat. Nos. 4,283,408; 4,362,736; 4,394,508; European Patent Application No. 40,696 and a pending application, U.S. Ser. No. 301,616, filed Sept. 14, 1981. The pharmaceutical compositions may also contain a $K^+/H^+$ ATPase inhibitor such as omeprazole, disclosed in U.S. Pat. No. 4,255,431, and the like. Each of the references referred to in this paragraph is hereby incorporated herein by reference.

Representative compounds of Formula I have been tested using the following assay to determine their mammalian leukotriene biosynthesis inhibiting activity.

Mouse Macrophage Assay

Mouse peritoneal macrophages were treated sequentially with arachidonic acid (labelled with tritium); the compound being evaluated as an inhibitor, and a stimulator (zymosan). Metabolites derived from arachidonic acid ($PGE_2$, 6-keto $PG\text{-}F_{1\alpha}$ and Leukotriene $C_4$) were separated from the incubation medium by extraction and chromatography, and then quantitated by determining the amount of radioactivity (cpm) associated with each of them. Inhibitors caused a reduction in the amount of radioactivity (cpm) associated with a given metabolite. (This protocol is identical to that described in the reference except that the radioactivity herein associated with the $LTC_4$ was determined by counting an aliquot of the final aqueous solution directly rather than chromatographying it first).

Reference: Humes, J. L. et al., *J. Biol. Chem.* 257, 1591–4 (1982).

The following table (Table II) reflects the leukotriene biosynthesis inhibiting ability of selected compounds of Formula I.

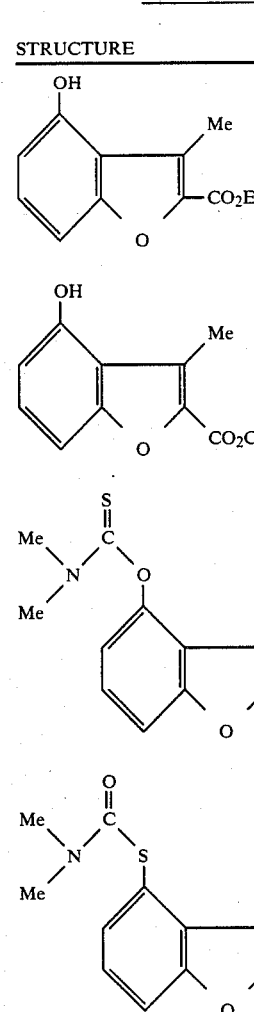

TABLE II
LEUKOTRIENE INHIBITION

| STRUCTURE | MACROPHAGE $ED_{50}$ (μg/ml) |
|---|---|
| (OH, Me, $CO_2Et$) | 0.2 |
| (OH, Me, $CO_2C(Me)_3$) | 1 |
| (Me$_2$N-C(=S)-O-, Me, $CO_2Et$) | 2.5–5 |
| (Me$_2$N-C(=O)-S-, Me, $CO_2Et$) | 5 |
| (MeC(=O)O-, Me, $CO_2Et$) | 5 |
| (MeC(=O)O-, Me, CONHPh) | 0.2 |
| (MeC(=O)O-, Me, CONH-p-ClPh) | 0.2 |
| (OH, Me, $CO_2H$) | 5 |
| (OH, Me, CONHPh) | 1–5 |
| (OH, Me, CNHNHPh(=O)) | 1 |

TABLE II-continued

LEUKOTRIENE INHIBITION

| STRUCTURE | MACROPHAGE ED$_{50}$ (μg/ml) |
|---|---|
| 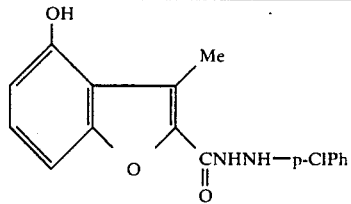 | 1 |

In addition to have leukotriene biosynthesis inhibition properties, the compounds of Formula I are useful as anti-asthma and analgesia agents. The following assays were employed in ascetaining these properties.

Asthmatic Rat Assay

Rats were obtained from an inbred line of asthmatic rats. Both female and male rats from 200 to 300 g were used.

Egg albumin (EA), grade V, crystallized and lyophilized, was obtained from Sigma Chemical Co., St. Louis, *Bordetella pertussis* vaccine, containing 30×10$^9$ killed bacteria per ml was obtained from the Institut Armand-Frappier, Laval des Rapides, Quebec. Aluminum hydroxide was obtained from the Regis Chemical Company, Chicago.

The challenge and subsequent respiratory recordings were carried out in a clear plastic box with internal dimensions 10×6×4 inches. The top of the box was removable; in use, it was held firmly in place by four clamps and an airtight seal was maintained by a soft rubber gasket. Through the center of each end of the chamber a Devilbiss nebulizer (No. 40) was inserted via an airtight seal and each end of the box also had an outlet. A Fleisch No. 0000 pneumotachograph was inserted into one end of the box and coupled to a Grass volumetric pressure transducer (PT5-A) which was then connected to a Beckman Type R Dynograph through appropriate couplers. While aerosolizing the antigen, the outlets were open and the pneumatachograph was isolated from the chamber. The outlets were closed and the pneumotachograph and the chamber were connected during the recording of the respiratory patterns. For challenge, 2 ml of a 3% solution of antigen in saline was placed into each neubulizer and the aerosol was generated with air from a small Potter diaphragm pump operating at 10 psi and a flow of 8 liters/minute.

Rats were sensitized by injecting (s.c.) 1 ml of a suspension containing 1 mg EA and 200 mg aluminum hydroxide in saline. Simultaneously, they received an injection (i.p.) of 0.5 ml of *B. pertussis* vaccine. They were used between days 14 and 18 postsensitization. In order to eliminate the serotonin component of the response, rats were pretreated intravenously 5 minutes prior to aerosol challenge with 30 gm kg$^{-1}$ methysergide. Rats were then exposed to an aerosol of 3% EA in saline for exactly 1 minute, then their respiratory profiles were recorded for a further 25–30 minutes. The duration of continuous dyspnea was measured from the respiratory recordings.

Compounds were generally administered either intraperitoneally 1 hour prior to challenge or orally 1½ hours prior to challenge. They were either dissolved in dimethylsulfoxide or suspended in 0.1% methocel and 0.5% Tween 80. The volume injected has 2 ml kg$^{-1}$ (intraperitoneally) or 10 ml kg$^{-1}$ (orally). Prior to oral treatment rats were starved overnight. Their activity was determined in terms of their ability to decrease the duration of symptoms of dyspnea in comparison with a group of vehicle-treated controls. Usually, a compound was evaluated at a series of doses and an ED$_{50}$ was determined. This was defined as the dose (in mg/kg) which would inhibit the duration of symptoms by 50%.

PAF-Induced Hyperalgesia Assay

Female Sprague-Dawley rats, 35–40 g were fasted overnight. Platelet activating factor, PAF, (L-lecithin B-acetyl O-alkyl) 1 μg/0.1 ml was given by subplantar injection in the rat paw. The compounds to be evaluated were homogenized in Aqueous Vehicle (0.9% benzyl alcohol, 0.5% Tween 80 and 0.4% methylcellulose) and administered orally in a volume of 0.1 ml, 30 minutes prior to PAF.

Animals were tested 1, 2, 3 and 4 hours after PAF administration. The vocalization threshold, defined as the pressure (mmHg) needed to evoke a squeak response, was recorded for both the injected and contralateral paw. No animal was subjected to pressure greater than 60 mmHg. Hyperalgesia is defined as a decrease in vocalization threshold as compared to a normal paw. Percent inhibition of hyperalgesia was calculated as the proportion of animals with vocalization thresholds greater than 200% of controls.

Table III reflects the anti-asthma and analgesia properties of selected Formula I compounds.

TABLE III

| ASSAY RESULTS | | |
|---|---|---|
| STRUCTURE | ASTHMATIC RAT | PAF HYPERALGESIA |
| 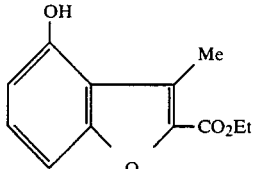 | 38% 5 mg/kg, i.v. | 10% 10 mg/kg, p.o. |
| 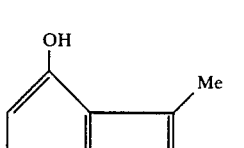 | 41% 15 mg/kg, p.o. | 60% 10 mg/kg, p.o. |
| 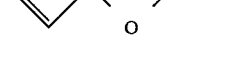 | 63% 5 mg/kg, i.v. | 50% 10 mg/kg, p.o. |
| 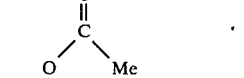 | | |

TABLE III-continued

ASSAY RESULTS

| STRUCTURE | ASTHMATIC RAT | PAF HYPERALGESIA |
|---|---|---|
| OH, Me, C(=O)—NHPh (benzofuran) | — | 60% 1.03 mg/kg, p.o. |
| OH, Me, C(=O)—NHNHPh (benzofuran) | — | 50% 20 mg/kg, p.o. |
| OH, Me, C(=O)—NHNHp-ClPH (benzofuran) | — | 60% 1 mg/kg, p.o. |

Another embodiment of the present invention are the novel compounds encompassed by Formula I. These novel compounds and certain additional compounds (marked with the superscript 4) are shown as compounds 116–365 above in Table I.

The discussion of methods of using the compounds of Formula I and compositions comprising such compounds as set forth in this application also applies to those compounds of Table I marked with a superscript 4.

Formula I includes both novel and known compounds. These compounds may be prepared by any process available to the skilled artisan.

One such process for compounds of Formula I (wherein X=O) is illustrated in Scheme I when $R_1$, $R_3$, $R_4$, T and V are compatible with the reaction conditions.

Reaction of alkoxide II with ethyl-2-bromoacetate yields the compound III which may be cyclized via an internal Claisen reaction to the benzofuran carboxylate IV.

Hydrolysis of the benzofuran carboxylate affords the carboxylic acid derivative V which may be derivatized to a number of useful compounds of Formula I, as illustrated for a compound of Formula VI.

SCHEME I

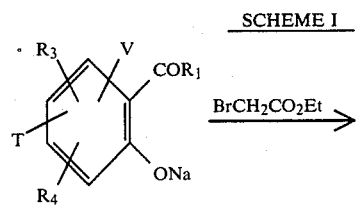

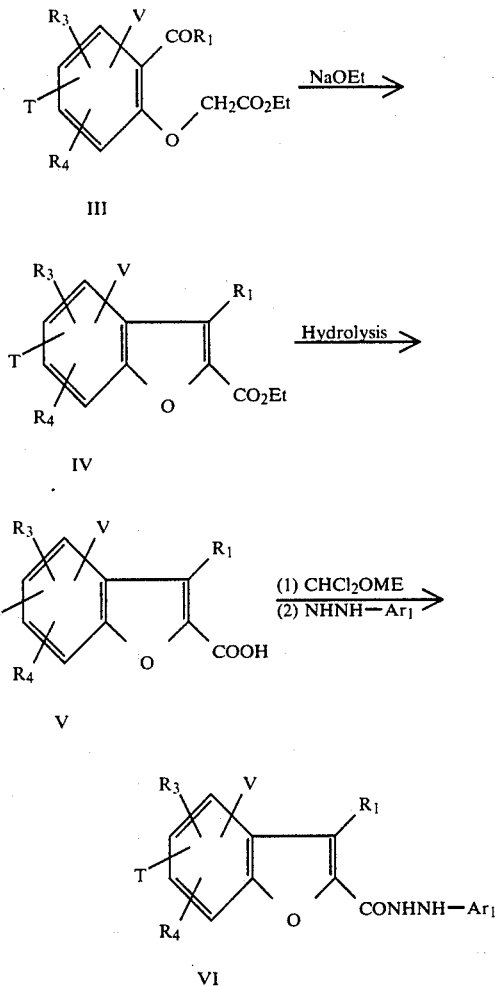

Thianaphthene (or benzothiophene) derivatives of Formula I (X=S) may be prepared as illustrated in Scheme II when $R_3$, $R_4$, T and V are compatible with the reaction conditions.

The substituted phenyl lithium compound (VII) is reacted with an appropriate disulfide to afford the thioether compound (VIII).

The thioether compound (VIII) is then reacted with polyphosphoric acid to cyclize the species and yield the thianaphthene compound (IX).

The thianaphthene compound (IX) may then be reacted with sodium or N-butyl lithium followed by carbonation to yield the 2-carboxylic acid compound (X).

Compound (X) may be oxidized by reaction hydrogen peroxide and acetic acid to afford the sulfoxide (XI) or the sulfone (XII).

The acids of Formula X, XI or XII may be further derivatized by standard methods to additional Formula I compounds.

SCHEME II

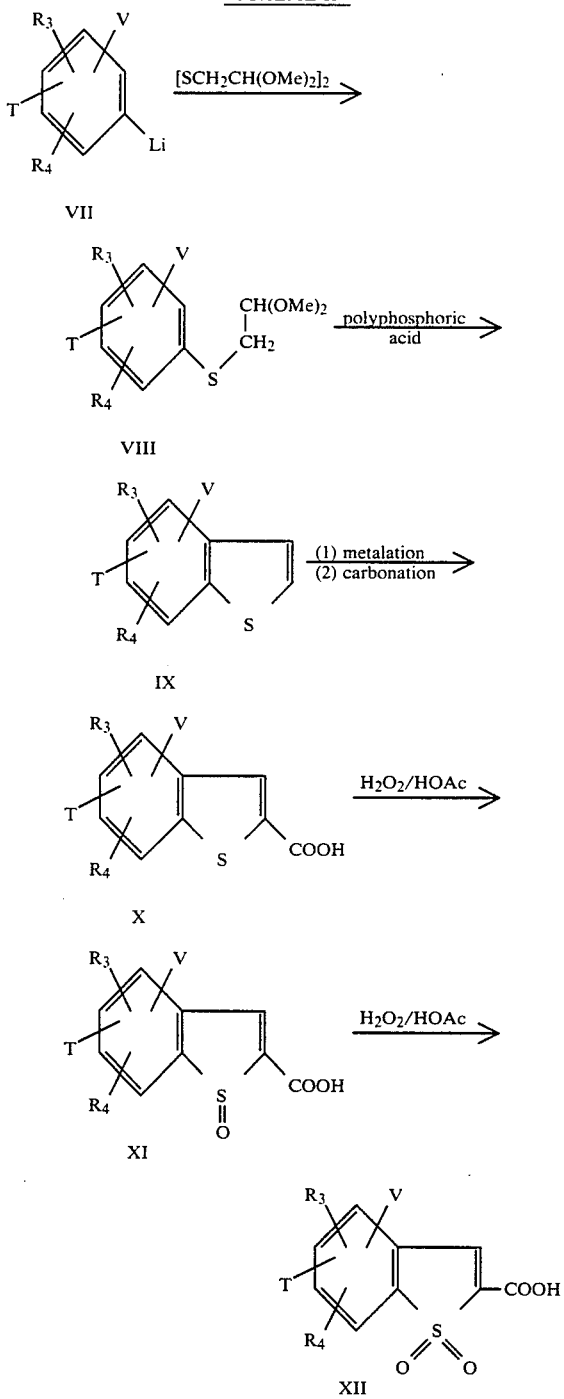

The following examples illustrate the present invention without, however, limiting the same thereto. Temperatures are expressed in °C. and are uncorrected.

EXAMPLE 1

3-Methyl-4-hydroxybenzofuran-2-carboxylic acid

A. Preparation of Ethyl(2-acetyl-3-hydroxyphenoxy)acetate

A mixture of 2,6-dihydroxyacetophenone (40 g), ethyl bromoacetate (48 g) and potassium carbonate (58 g) in acetone (500 ml) was refluxed for 3 hours. The mixture was cooled and filtered. The solution was evaporated to dryness and the crude solid extracted with boiling hexane. Upon cooling, the title compound was obtained.

Analysis, calculated: C, 60.50; H, 5.92. Found: C, 60.48; H, 5.93.

B. Preparation of Ethyl 4-hydroxy-3-methylbenzofuan-2-carboxylate

Method A:

To a stirred solution of sodium ethoxide in ethanol (100 mmole Na in 500 ml EtOH) was added the compound of Step A above (23.8 g). The mixture was heated to 75° and stirred for two hours. The mixture was cooled to 0° and 1N HCl was added. The mixture was concentrated in vacuo to about 200 ml and diluted with water and ether. The mixture wax extracted with ethyl acetate. The organic extracts were washed with 1N $NaHCO_3$ (3×), brine, dried ($Na_2SO_4$) and concentrated to a yellow solid. Recrystallization from toluene-hexane afforded the title compound as a pink solid, m.p. 158°.

Method B:

A sodium ethoxide solution was prepared by dissolving sodium metal (145 g; 6.3 moles) in ethanol (10.6 L) under nitrogen atmosphere. The solution was cooled to between −5° C. and −10° C. Over 5 minutes, 2-hydroxy-6-ethoxycarbonylmethoxy acetophenone (1.0 kg; 4.2 moles), was added with stirring. The mixture was then stirred for 18 hours with the internal temperature being maintained between 0° C. and 7° C. The reaction was then poured into a cold stirring mixture of water (10 L), concentrted hydrochloric acid (2.5 L) and ice (13 L). After stirring for 10 minutes a saturated sodium chloride solution (4 L) was added. The title compound was filtered and dried to obtain 940 grams.

C. Preparation of 3-Methyl-4-hydroxybenzofuran-2-carboxylic acid

A mixture of the ester from Step B above (220 mg), 2N NaOH (3 ml) and ethanol (3 ml) was stirred at room temperature for 3½ hours. The mixture was evaporated and the residue acidified with 2N $H_2SO_4$ buffered with saturated $NH_4Cl$. The mixture was extracted with ethyl acetate, dried and concentrated to a solid. Recrystallization from water-methanol afforded the title compound as colorless crystals, m.p. 260° (dec.).

EXAMPLE 2

Ethyl 3-Methyl-4-methoxybenzofuran-2-carboxylate

To a suspension of sodium hydride (36.8 mg) in THF (tetrahydrofuran) (3 ml) at 0° was added the compound of Example 1, Step B (286 mg). The mixture was stirred at room temperature for 30 minutes. Methyl iodide (600 μl) was added to the mixture. After 20 minutes, DMF (dimethylformamide) (0.5 ml) was added. The mixture was stirred at room temperature for 30 minutes and water was added. The mixture was extracted with ether and ethyl acetate. The combined organic extracts were washed with dilute HCl, dilute $K_2CO_3$, dried ($Na_2SO_4$) and concentrated in vacuo. Recrystallization of the residue from hexane afforded the title compound as off-white needles, m.p. 65°–66°.

Analysis, calculated: C, 66.66; H, 6.02. Found: C, 66.57; H, 6.18.

EXAMPLE 3

(5-Methyl-2-oxo-1,3-dioxolen-4-ylmethyl) 4-hydroxy-3-methylbenzofuran-2-carboxylate The compound of Example 1, Step C (192.2 mg) was dissolved in DMF (4 ml). To this solution at room temperature was added 4-bromomethyl-5-methyl-1,3-dioxolen-2-one (386 mg). The mixture was cooled to 0° and potassium carbonate (97 mg) was added. The reaction mixture stirred at room temperature for 16 hours. Ammonium chloride was added to the solution, followed by 2N HCl. The mixture was extracted with ethyl acetate. The combined extracts were dried ($Na_2SO_4$) and concentrated in vacuo to a yellow oil. Chromatography on silica gel afforded the title compound as a solid. Recrystallization from chloroform afforded light pink needles, m.p. 168°–170°.

Analysis, calculated: C, 59.22; H, 3.98. Found: C, 59.13; H, 4.17.

EXAMPLE 4

Ethyl 4-(N,N-dimethylthiocarbamyloxy)-3-methylbenzofuran-2-carboxylate

The compound of Example 1, Step B (384 mg) was added at 0° to a suspension of sodium hydride (57.9 mg) in DMF (2 ml). The mixture was stirred at room temperature for 30 minutes and N,N-dimethylthiocarbamoyl chloride (158 mg) is added. The mixture is stirred at 70° for 1 hour. The mixture is cooled to room temperature, ice water is added and the mixture extracted with ether. The ether extracts were dried ($Na_2SO_4$) and evaporated to a yellow solid. Recrystallization from ethanol-hexane afforded the title compound, m.p., 141°–145°.

EXAMPLE 5 tert-Butyl 4-hydroxy-3-methylbenzofuran-2-carboxylate

To a solution of potassium tert-butoxide (448 mg) in tert-butanol (10 ml) was added the compound of Example 1, Step B (440 mg). The mixture was heated at 90° for 20 hours. The reaction mixture was concentrated in vacuo and the residue dissolved in cold (0°) 2N $H_2SO_4$ buffered with $NH_4Cl$. The mixture was extracted with ethyl acetate. The extracts were washed with brine, dried ($Na_2SO_4$) and concentrated. Preparative thin layer chromatography afforded the title compound, m.p. 158°–159°.

Analysis calculated: C, 67.73; H, 6.50. Found: C, 67.64; H, 6.39.

EXAMPLE 6

Ethyl 4-(N,N-dimethylcarbamylthio)-3-methyl benzofuran-2-carboxylate

The compound of Example 4 (109 mg) was heated from 140° to 200°. The color of the solid changed from yellow to red at 200°. After 15 minutes at 200° heating was stopped. The solid cooled to room temperature and was recrystallized from ethyl acetate-hexane to afford the title compound as light red needles.

Analysis, calculated: C, 58.63; H, 5.58; N, 4.56; S, 10.41. Found: C, 58.57; H, 5.27; N, 4.60; S, 10.03.

EXAMPLE 7

2-Formyl-4-hydroxy-3-methylbenzofuran

A. Preparation of 2-Hydroxymethyl-3-methyl-4-hydroxybenzofuran

To a stirred suspension of aluminum hydride (216 mg) at 0° in THF (10 ml was added the compound of Example 1, Step B (220 mg). The white mixture was stirred at 0° for 1 hour. The reaction was quenched with cold dilute HCl and extracted with ethyl acetate. The organic extracts were washed with brine, dried ($Na_2SO_4$) and concentrated to a light pink solid. Recrystallization from chloroform-methanol afforded the title compound, m.p., 141°–145°.

Analysis, calculated: C, 67.41; H, 5.66. Found: C, 67.45; H, 5.86.

B. Preparation of 2-Formyl-4-hydroxy-3-methylbenzofuran

To a solution of the compound of step A (356 mg) in methylene chloride (50 ml) is added pyridinium chlorochromate (648 mg). Stir the reaction mixture at room temperature for 1.5 hours and then filter through a bed of Florisil. Evaporate the filtrate and purify the residue by chromatography over 30 g of silica gel, using methylene chloride-ethyl acetate as eluent to obtain the title compound.

EXAMPLE 8

4-Acetoxy-3-methylbenzofuran-2-carboxylic acid

Method A:

The compound of Example 1, Step C (1.43 g) was suspended in acetic anhydride (16.20 g, 15 ml) and cooled to 0°. To the suspension was added pyridine (3 ml). The reaction mixture was stirred at room temperature for 27.5 hours. Water (3 ml) was added, the reaction was stirred for 3 hours, and was concentrated in vacuo. The residue was recrystallized from methanol-water to afford the title compound.

Method B:

4-Acetoxy-3-methyl benzofuran-2-carboxylic acid

The compound of Example 1, Step C, (6 g, 31.25 mmoles) was mixed with to acetic anhydride (60 ml) and boronoxide (2.17 g, 1 eq.). The mixture was warmed to 70° C. for 1 hour. The mixture was cooled and poured into 800 ml ice and water and stirred for 15 minutes. Filtration and air drying gave 7 g or 95% of 4-Acetoxy-3-methyl benzofuran-2-carboxylic acid.

EXAMPLE 9

N-Phenyl-4-hydroxy-3-methylbenzofuran-2-carboxamide

Method A:

The compound of Example 8 (300 mg) was refluxed in dichloromethylmethyl ether (20 ml) for 30 minutes. The solution was evaporated to dryness and the resulting solid (acid chloride) was dissolved in ether (10 ml). A solution of aniline (1 g) in ether (10 ml) was added. After stirring for 15 minutes, water (50 ml) and ethyl acetate (50 ml) were added. The organic layer was removed, washed with dilute HCl and evaporated to dryness. The residue was dissolved in methanol and treated with 1N NaOH. After stirring at room temperature for 10 minutes, the mixture was concentrated, dilute HCl was added and the resulting precipitate collected affording the title compound as a white solid, m.p. 237°–238°.

Analysis, calculated: C, 68.07; H, 5.00; N, 9.92. Found: C, 67.99; H, 5.20; N, 9.99.

Method B:

Step 1:

N-Phenyl-4-methoxycarbonyloxy-3-methylbenzofuran-2-carboxamide

To a mixture of 4-hydroxy-3-methylbenzofuran-2-carboxylic acid (1.12 g, 6 mmole), ethyl chloroformate (1.01 ml, 13.2 mmole), and methylene chloride (20 ml) stirred at 0°–5° C. under argon was added triethylamine (1.82 ml, 13.2 mmole) in methylene chloride (6 ml) dropwise over 5 minutes. The mixture was stirred for 15 minutes and then aniline (1.11 mg, 12 mmole) was added followed by the dropwise addition of triethylamine (1.82 ml, 13.2 mmole) in methylene chloride (3 ml). After 30 minutes, the reaction mixture was washed with water, dried with MgSO$_4$ and evaporated to dryness. The crude product was purified by column chromatography (70 g of Merck silica gel eluted with 1:1:3 ethyl acetate/methylene chloride/hexane to yield 1.38 g (68.1%) of product.

Step 2:

N-Phenyl-4-hydroxy-3-methylbenzofuran-2-carboxamide

A mixture of N-phenyl-4-methoxycarbonyloxy-3-methylbenzofuran-2-carboxamide (328 mg, 1 mmole), methanol (1.5 m) and 10% potassium carbonate solution (1.5 ml) was stirred under argon overnight. After partial neutralization with acetic acid (0.06 ml) and evaporation to about 5 ml, water and ethyl acetate were added. The aqueous layer was extracted a second time with ethyl acetate and then acidified with hydrochloric acid and extracted again. The combined ethyl acetate extract was washed with saturated sodium chloride solution, dried with MgSO$_4$, and evaporated to a gum. Column chromatography of the latter (Merck silica gel eluted with 1:1:2 ethyl acetate/methylene chloride/hexane) gave 200 mg of product (80%).

EXAMPLE 10

$N^2$-Phenyl-4-hydroxy-3-methylbenzofuran-2-carboxyhydrazide

Following the procedure of Example 9 (Method A or B), but substituting an equivalent amount of phenylhydrazine for aniline, there was obtained the title compound, m.p. 234°–235°.

Analysis, calculated: C, 71.90; H, 4.90; N, 5.24. Found: C, 71.91; H, 4.93; N, 5.27.

EXAMPLE 11

$N^2$-(4-Chlorophenyl)-4-hydroxy-3-methylbenzofuran-2-carboxyhydrazide

Following the procedure of Example 9, but substituting an equivalent amount of p-chlorophenylhydrazine for aniline, there was obtained the title compound, m.p. 241°–242°.

Analysis, calculated: C, 60.67; H, 4.14; N, 8.85; Cl, 11.20. Found: C, 60.80, H, 4.34; N, 8.83; Cl, 11.11.

EXAMPLE 12

N-Phenyl-4-acetoxy-3-methylbenzofuran-2-carboxamide

Method A:

Methyl chloroformate (206 mg) was added dropwise to a stirred solution of the compound of Example 8 (427 mg) and triethylamine (221 mg) in THF (10 ml). The solution was cooled to 0°. After 15 minutes, aniline (169 mg) dissolved in THF (1 ml) was added dropwise to the cold solution. The reaction was stirred at 0° for 2 hours, warmed to room temperature and stirred an additional 2 hours. After dilution with EtOAc (50 ml), the reaction mixture was extracted with dilute base (3×), dilute acid (3X), washed with water, dried (Na$_2$SO$_4$) and evaporated in vacuo to afford the title compound.

Analysis, calculated: C, 69.89; H, 4.88. Found: C, 69.71; H, 4.81.

Method B

A mixture of 4-acetoxy-3-methylbenzofuran-2-carboxylic acid (2 mmole) and α,α-dichloromethyl methyl ether (5 ml) was stirred under reflux for 2 hours. Excess reagent was evaporated off under vacuum and the residue was treated twice with small quantities of dry toluene followed by evaporation to dryness.

The oily acid chloride was dissolved in methylene chloride and the solution was added dropwise with stirring to an ice-cold solution of aniline (2 mmole) and triethylamine (0.42 ml) in methylene chloride. After stirring the mixture at room temperature for 30 minutes, it was washed with dilute hydrochloric acid, then with saturated sodium bicarbonate solution and finally with water. The solution was dried with MgSO$_4$ and evaporated to a solid. The solid was recrystallized from ethyl acetate/diisopropyl ether to give the title compound (78.1%).

EXAMPLE 13

N-(4Chlorophenyl)-4-acetoxy-3-methylbenzofuran-2-carboxamide

Following the procedure of Example 12, but substituting an equivalent amount of p-chloroaniline for aniline and allowing 96 hours for the reaction at room temperature afforded the title compound.

Analysis, calculated: C, 62.88; H, 4.10; N, 4.07. Found: C, 63.00; H, 4.03; N, 4.03.

EXAMPLE 14

N-Benzyl-4-acetoxy-3-methylbenzofuran-2-carboxamide

The compound of Example 8 (132 mg) was suspended in methylene chloride (5 ml). To the suspension was added triethylamine (0.12 ml). The solution was cooled to 0° and methylchloroformate (533 mg) was added dropwise. The solution was stirred at 0° for 1 hour and then evaporated to dryness at 0°. The residue was dissolved into THF and benzylamine (0.1 ml) was added at 0°. The solution stirred at 0° for 1 hour and was diluted with methylene chloride. Water and 1N HCl was added to lower the pH to about 1. The solution was extracted into methylene chloride, dried with MgSO$_4$ and evaporated in vacuo. Preparative thin layer chromatography afforded the title compound.

Analysis calculated: C, 70.57; H, 5.30. Found: C, 70.12; H, 5.22.

EXAMPLES 15-21

Following the procedure of Example 1A and 1B, Method B, compounds of Formula I wherein Z is a bond, X is oxygen, and T and V are hydrogen were prepared and are set forth in Table IV. Physical data is presented in Table V. The compounds are listed as:

TABLE IV

| Examples | $R_1$ | $R_2$ | $R_3$ | $R_4$ |
|---|---|---|---|---|
| 15 | Me | OEt | 4-OH | 6-OMe |
| 16 | Me | OEt | 4-OH | 5-Pr |
| 17 | Ph | OEt | 4-OH | H |
| 18 | Pr | OEt | 6-OH | H |
| 19 | Me | OMe | 6-OH | H |
| 20 | Me | OEt | 6-OH | H |
| 21 | Ph | OEt | 4-OH | 5-C(O)Ph |

TABLE V

| EXAMPLE | M.P. | ANALYSIS | |
|---|---|---|---|
| 15 | | Calc'd: | C, 62.39, H, 5.64 |
| | | Found: | C, 62.89; H, 5.72 |
| 16 | 132–133° C. | Calc'd: | C, 68.68, H, 6.91 |
| | | Found: | C, 68.40; H, 6.74 |
| 17 | 159° | Calc'd: | C, 72.33, H, 5.00 |
| | | Found: | F, 72.19, H, 5.14 |
| 18 | | Calc'd: | C, 67.73, H, 6.50 |
| | | Found: | C, 67.70, H, 6.48 |
| 19 | | Published | |
| 20 | — | | |
| 21 | 151–152° C. | | |

EXAMPLES 22-37

Following the procedure of Example 9, but substituting an equivalent amount of various substituted amines for aniline, compounds of the Formula I wherein Z is a bond, X is oxygen and T and V are hydrogen, were prepared. The compounds are listed as Examples 22 to 37 in Table VI. Physical data is presented in Table VIa.

TABLE VI

| Examples | Method | $R_1$ | $R_2$ | $R_3$ | $R_4$ |
|---|---|---|---|---|---|
| 22 | B | $CH_3$ | piperidin-1-yl | 4-OH | H |
| 23 | A | $CH_3$ | NHPh—p-$NO_2$ | 6-OH | H |
| 24 | B | $CH_3$ | NHPh—p-OMe | 6-OH | H |
| 25 | B | $CH_3$ | NHPh—p-OMe | 4-OH | H |
| 26 | A | $CH_3$ | NHPh—p-$NO_2$ | 4-OH | H |
| 27 | B | $CH_3$ | NH-(pyridin-4-yl) | 4-OH | H |
| 28 | B | $CH_3$ | NH-(3,4-methylenedioxyphenyl) | 4-OH | H |
| 29 | B | $CH_3$ | NHPh | 4-OH | 5-$CH_2SCH_3$ |
| 30 | B | Pr | NHPh—p-Cl | 6-OH | H |
| 31 | A | $CH_3$ | NH-(1H-tetrazol-5-yl)methylamino | 5-OH | H |
| 32 | B | Ph | NHPh—p-Cl | 6-OH | H |
| 33 | A | $CH_3$ | NH-(1H-tetrazol-5-yl)methylamino | 4-OH | H |
| 34 | B | $CH_3$ | NMePh | 4-OH | H |
| 35 | A | $CH_3$ | NHPh—p-OMe | 4-OH | 5-Pr |
| 36 | B | $CH_3$ | NHPh—p-Cl | 4-OH | H |
| 37 | B | $CH_3$ | NHPh—p-Cl | 5-OH | H |

TABLE VIa

| Example | m.p. | Analysis | |
|---|---|---|---|
| 22 | 189° C. | Calc'd: | C, 69.48, H, 6.61, N, 5.40 |
| | | Found: | C, 69.40, H, 6.60, N, 5.47 |
| 23 | | Calc'd: | C, 61.54, H, 3.87, N, 8.97 |
| | | Found: | C, 60.81, H, 3.82, N, 8.77 |
| 24 | 212–213° C. | Calc'd: | C, 68.68, H, 5.09, N, 4.71 |
| | | Found: | C, 68.64, H, 5.18, N, 4.64 |
| 25 | | Calc'd: | C, 68.68, H, 45.09, N, 4.71 |
| | | Found: | C, 68.52, H, 5.27, N, 4.60 |
| 26 | 300° C. (Dec.) | Calc'd: | C, 61.54, H, 3.87, N, 8.97 |
| | | Found: | C, 61.49, H, 4.01, N, 8.72 |
| 27 | 300° C. (Dec.) | Calc'd: | C, 67.16, H, 4.51, N, 10.44 |
| | | Found: | C, 67.02, H, 4.35, N, 10.34 |
| 28 | 225–227° C. | Calc'd: | C, 65.59, H, 4.21, N, 4.50 |
| | | Found: | C, 65.17, H, 4.13, N, 4.46 |
| 29 | 195–196° C. | Calc'd: | C, 66.05, H, 5.24, N, 4.28, S, 9.77 |
| | | Found: | C, 66.25, H, 5.03, N, 4.24, S, 9.43 |
| 30 | | Calc'd: | C, 65.56, H, 4.89, Cl, 10.75, N, 4.25 |
| | | Found: | C, 65.34, H, 4.99, Cl, 11.01, N, 4.20 |
| 31 | | Calc'd: | C, 46.15, H, 4.19, N, 27.02 |
| | | Found: | C, 46.08, H, 4.58, N, 27.39 |
| 32 | | Calc'd: | C, 66.06, H, 4.22, Cl, 9.28, N, 3.66 |
| | | Found: | C, 65.84, H, 4.27, Cl, 9.21, N, 3.59 |
| 33 | | Calc'd: | C, 48.90, H, 3.44, N, 21.94 |
| | | Found: | 48.87, H, 3.41, N, 22.04 |
| 34 | 220–222° C. | Calc'd: | C, 72.56, H, 5.37, N, 4.98 |
| | | Found: | C, 72.76, H, 5.50, N, 4.65 |
| 35 | 155–157° C. | Calc'd: | C, 70.77, H, 6.23, N, 4.12 |
| | | Found: | C, 70.87, H, 6.13, N, 4.02 |
| 36 | | Calc'd: | C, 63.69, H, 3.98, N, 4.64, Cl, 11.76 |
| | | Found: | C, 63.54, H, 4.13, N, 4.94, Cl, 12.10 |
| 37 | | Calc'd: | C, 63.69, H, 3.98, Cl, 11.76, N, 4.64 |
| | | Found: | C, 63.77, H, 3.97, Cl, 12.15, N, 4.43 |

EXAMPLES 38-44

Following the procedure of Example 12, but substituting an equivalent amount of various substituted anilines for aniline compounds of the formula I wherein Z is a bond, X is oxygen and T and V are hydrogen were prepared. The compounds are listed as Examples 38 to 44 in Table VII. Physical data is presented in Table VIIa.

TABLE VII

| Examples | Method | R₁ | R₂ | R₃ | R₄ |
|---|---|---|---|---|---|
| 38 | A | $CH_3$ | p-acetoxy-anilino (HN-C₆H₄-OAc structure) | 4-OAc | H |
| 39 | A | $CH_3$ | NHPh—p-$NO_2$ | 4-OAc | H |
| 40 | B | $CH_3$ | NHPh—p-OMe | 4-OAc | H |
| 41 | B | Ph | NHPh—p-Cl | 6-OAc | H |
| 42 | B | $CH_3$ | —NMePh | 4-OAc | H |
| 43 | A | $CH_3$ | 4-aminopyridinyl (HN-pyridine structure) | 4-OAc | H |
| 44 | B | Pr | NHPh—p-Cl | 6-OAc | H |

TABLE VIIa

| Example | m.p. | Analysis | |
|---|---|---|---|
| 38 | 187–190° C. | Calc'd: | C, 64.59, H, 4.28, N, 3.96 |
| | | Found: | C, 64.50, H, 4.32, N, 3.88 |
| 39 | 239° C. | Calc'd: | C, 61.02, H, 3.98, N, 7.91 |
| | | Found: | C, 60.83, H, 4.05, N, 7.86 |
| 40 | 134° C. | Calc'd: | C, 67.25, H, 5.05, N, 4.13 |
| | | Found: | C, 67.39, H, 5.06, N, 4.22 |
| 41 | | Calc'd: | C, 68.07, H, 3.97, Cl, 8.74, N, 3.45 |
| | | Found: | C, 67.89, H, 4.04, Cl, 8.83, N, 3.47 |
| 42 | 117–118° C. | Calc'd: | C, 70.56, H, 5.30 N, 4.33 |
| | | Found: | C, 70.71, H, 4.97, N, 4.16 |
| 43 | 200–201° C. | Calc'd: | C, 65.80, H, 4.55, N, 9.03 |
| | | Found: | C, 65.94, H, 4.49, N, 9.16 |
| 44 | 151–152° C. | Calc'd: | C, 64.61, H, 4.88, Cl, 9.53, N, 3.77 |
| | | Found: | C, 64.76, H, 4.90, Cl, 9.41, N, 3.76 |
| 45 | 130–131° | Calc'd | C, 66.48, H, 5.83, N, 3.52 |
| | | Found: | C, 66.49, H, 5.39, N, 3.45 |
| 46 | 174–175° C. | Calc'd: | C, 63.06, H, 4.54, Cl, 8.87, N, 3.50 |
| | | Found: | C, 62.73, H, 4.14, Cl, 8.50, N, 3.69 |
| 47 | 162–163° C. | Calc'd: | C, 62.33, H, 4.97, N, 3.63, S, 8.30 |
| | | Found: | C, 62.64, H, 4.76, N, 3.71, S, 8.32 |

EXAMPLES 45–48

Following the procedure of Example 9, Method B, Step 1, but substituting an equivalent amount of various substituted aniline for aniline itself, compounds of the Formula I, wherein Z is a bond, X is oxygen and T and V are hydrogen, were prepared. The compounds are listed as Examples 45 to 48 in Table VIII. Physical data is presented in Table VIIIa.

TABLE VIII

| Examples | R₁ | R₂ | R₃ | R₄ |
|---|---|---|---|---|
| 45 | Pr | NHPh—p-Cl | 6-O-C(=O)-O-$OCH_3$ (carbonate) | H |
| 46 | $CH_3$ | NHPh—p-OMe | 4-O-C(=O)-O-$OCH_3$ | 5-Pr |
| 47 | $CH_3$ | NHPh—p-Cl | 4-O-C(=O)-O-$OCH_3$ | 5-$CH_2CH=CH_2$ |
| 48 | $CH_3$ | NHPh | 4-O-C(=O)-O-$OCH_3$ | 5-$CH_2SCH_3$ |

TABLE VIIIa

| Examples | m.p. | Analysis | |
|---|---|---|---|
| 45 | | Calc'd: | C, 61.94; H, 4.68; N, 3.61 |
| | | Found: | C, 61.94; H, 4.75; N, 3.56 |
| 46 | 130–131° C. | Calc'd: | C, 66.48; H, 5.83; N, 3.52 |
| | | Found: | C, 66.49; H, 5.39; N, 3.45 |
| 47 | 174–175° C. | Calc'd: | C, 63.06; H, 4.54; Cl, 8.87; N, 3.50 |
| | | Found: | C, 62.73; H, 4.14; Cl, 8.50; N, 3.69 |
| 48 | 162–163° C. | Calc'd: | C, 62.33; H, 4.97; N, 3.63; S, 8.30 |
| | | Found: | C, 62.64; H, 4.76; N, 3.71; S, 8.32 |

EXAMPLES 49–76

Following the procedure of Example 9, but substituting an equivalent amount of various substituted phenylhydrazines for aniline, compounds of the Formula I, wherein Z is a bond, X is oxygen and T and V are hydrogen, were prepared. The compounds are listed as Examples 49 to 76 in Table IX. Physical data is presented in Table IXa.

TABLE IX

| Examples | Method | R₁ | R₂ | R₃ | R₄ |
|---|---|---|---|---|---|
| 49 | B1 | $CH_3$ | NHNHPh—3,4-$Cl_2$ | 4-O-C(=O)-O-$OCH_3$ | H |
| 50 | B1 | $CH_3$ | NHNHPh—p-Cl | 4-O-C(=O)-O—$CH_2CH(CH_3)_2$ | H |
| 51 | B1 | $CH_3$ | NHNHPh—p-OMe | 4-O-C(=O)-O-OMe | H |

TABLE IX-continued

| Examples | Method | R₁ | R₂ | R₃ | R₄ |
|---|---|---|---|---|---|
| 52 | B2 | Ph | NHNHPh—p-OMe | 6-OH | H |
| 53 | B2 | CH₃ | NHNHPh—3,4-Cl₂ | 4-OH | H |
| 54 | A | CH₃ | —NMeNmePh | 4-OH | H |
| 55 | B1 | CH₃ | NHNHPh | 4-O-C(=O)-OMe | H |
| 56 | A | CH₃ | NHNHPh—p-OMe | 4-OH | 5-Pr |
| 57 | B2 | CH₃ | NHNHPh—p-Cl | 5-OH | H |
| 58 | B1 | Pr | NHNHPh—p-OMe | 4-O-C(=O)-OMe | H |
| 59 | A | Pr | NHNHPh—p-OMe | 6-OH | H |
| 60 | B2 | CH₃ | —NEtNHPh | 4-OH | H |
| 61 | B2 | CH₃ | NHNHPh—p-Cl | 6-OH | H |
| 62 | A | CH₃ | —NHNHPh—p-OMe | 5-OH | H |
| 63 | B2 | CH₃ | —NHNHPh—p-OMe | 4-OH | H |
| 64 | A | CH₃ | NHNHPh—p-NO₂ | 4-OH | H |
| 65 | B1 | CH₃ | NHNHPh—p-Cl | 4-O-C(=O)-OMe | H |
| 66 | B2 | CH₃ | NHNHPh—m-OMe | 4-OH | H |
| 67 | A | CH₃ | NHNHPh—p-Cl | 5,6-OCH₂O | H |
| 68 | A | CH₃ | NHNHPh—p-Cl | 5-OH | 6-OH |
| 69 | A | CH₃ | NHNHPh—p-OMe | 4-O-CH₂-CH(OH)-CH₃ | H |
| 70 | B1 | CH₃ | NHNHPh—p-OMe | 4-O-C(=O)-OMe | 5-CH₂SCH₃ |
| 71 | B1 | CH₃ | —NHNHPh—p-OMe | 5-O-C(=O)-OMe | H |
| 72 | B1 | CH₃ | —NHNHPh—p-Cl | 5-O-C(=O)-OMe | H |
| 73 | B1 | CH₃ | —NHNHPh—p-OMe | 4-O-C(=O)-OMe | 5-CH₂CH=CH₂ |
| 74 | B1 | CH₃ | NMeNMePh | 4-O-C(=O)-OMe | H |
| 75 | B1 | CH₃ | NHNHPh—p-Cl | 4-O-C(=O)-OEt | H |
| 76 | B1 | CH₃ | NHNHPh—p-OMe | 4-O-C(=O)-OMe | 5-Pr |

TABLE IXa

| Example | M.P | Analysis |
|---|---|---|
| 49 | 223–225° C. | Calc'd: C, 52.81, H, 3.45, N, 6.84, Found: F, 57.77, 3.58, 6.67, 17.52 Cl, 17.53 |
| 50 |  | Calc'd: C, 60.51, H, 5.08, Cl, 8.50, N, 6.72 Found: 60.81, 5.29, 9.01, 6.73 |
| 51 | 131–133° C. | Calc'd: C, 61.59, H, 4.90, N, 7.56, Found: 61.81, 4.89, 7.64 |

TABLE IXa-continued

| Example | M.P | Analysis | | |
|---|---|---|---|---|
| 52 | | Calc'd: | C, 70.58, H, 4.85, N, 7.48 | |
| | | Found: | 70.41, 5.00, 7.36 | |
| 53 | 275° C. (dec) | Calc'd: | C, 54.70, H, 3.44, N, 7.98, Cl, 20.20 | |
| | | Found: | 54.82, 3.48, 7.69, 19.97 | |
| 54 | 177–180° C. | Calc'd: | C, 69.64, H, 5.84, N, 9.03 | |
| | | Found: | 69.73, 5.80, 9.00 | |
| 55 | 166–168° C. | Calc'd: | C, 63.53, H, 9.74, N, 8.23 | |
| | | Found: | 63.65, 4.84, 8.29 | |
| 56 | 155–157° C. | | | |
| 57 | | Calc'd: | C, 60.67, H, 4.10, N, 8.84, Cl, 11.20 | |
| | | Found: | 60.65, 4.37, 8.41, 11.10 | |
| 58 | 120–121° C. | Calc'd: | C, 63.28, H, 5.56, N, 7.03 | |
| | | Found: | 62.97, 5.50, 6.95 | |
| 59 | | | | |
| 60 | | Calc'd: | C, 67.70, H, 6.00, N, 8.77 | |
| | | Found: | 67.34, 6.26, 8.62 | |
| 61 | | Calc'd: | C, 60.67, H, 4.14, Cl, 10.19, N, 8.84 | |
| | | Found: | 60.61, 4.26, 10.84, 8.98 | |
| 62 | | | | |
| 63 | >300° C. | | | |
| 64 | 277° C. (dec) | Calc'd: | C, 58.72, H, 4.00, N, 12.84 | |
| | | Found: | 58.62, 4.22, 12.76 | |
| 65 | 197–199° C. | Calc'd: | C, 57.66, H, 4.03, Cl, 9.46, N, 7.48 | |
| | | Found: | 67.96, 3.73, 9.24, 7.80 | |
| 66 | | Calc'd: | C, 65.38, H, 5.16, N, 8.97 | |
| | | Found: | 65.55, 5.36, 8.31 | |
| 67 | 264–265° C. | Calc'd: | C, 59.22, H, 3.77, N, 8.12, Cl, 10.29 | |
| | | Found: | 59.02, 3.90, 7.95, 10.38 | |
| 68 | | Calc'd: | C, 57.75, H, 3.91, N, 8.42, Cl, 10.66 | |
| | | Found: | 57.11, 4.30, 8.34, 10.74 | |
| 69 | 84–88° C. | | | |
| 70 | 145–147° C. | Calc'd: | C, 58.60, H, 5.15, N, 6.51, S, 7.44 | |
| | | Found: | 59.36, 5.35, 6.87, 8.00 | |
| 71 | | Calc'd: | C, 61.60, H, 4.80, N, 7.50 | |
| | | Found: | 61.39, 5.04, 7.22 | |
| 72 | | Calc'd: | C, 57.68, H, 4.00, N, 7.47, Cl, 9.46 | |
| | | Found: | 57.73, 3.98, 7.30, 9.13 | |
| 73 | 130–132° C. | Calc'd: | C, 64.36, H, 5.40, N, 6.83 | |
| | | Found: | 64.58, 5.24, 6.75 | |
| 74 | 109–111° C. | Calc'd: | C, 65.18, H, 5.47, N, 7.60 | |
| | | Found: | 65.02, 5.44, 7.15 | |
| 75 | | Calc'd: | C, 58.69, H, 4.41 | |
| | | Found: | 58.84, 4.54 | |
| 76 | 154–156° C. | Calc'd: | C, 64.06, H, 5.87, N, 6.79 | |
| | | Found: | 61.84, 5.69, 6.57 | |

EXAMPLES 77–90

Following the procedure of Example 12, but substituting an equivalent amount of various substituted phenylhydrazines for aniline, compounds wherein Z is a bond, X is oxygen and T and V are hydrogen, were prepared. The compounds are listed as Examples 77 to 90 in Table X. Physical data are presented in Table Xa.

TABLE X

| Examples | Method | $R_1$ | $R_2$ | $R_3$ | $R_4$ |
|---|---|---|---|---|---|
| 77 | B | $CH_3$ | NHNHPh—p-Cl | 5-OAc | 6-OAc |
| 78 | A | $CH_3$ | NHNHPh—p-OMe | 4-OAc | H |
| 79 | B | $CH_3$ | NHNHPh—p-$NO_2$ | 4-OAc | H |
| 80 | A | $CH_3$ | 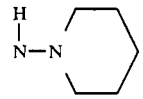 | 4-OAc | H |
| 81 | A | $CH_3$ | NHNHPh—p-Cl | 4-OAc | H |
| 82 | B | Ph | NHNHPh—p-OMe | 6-OAc | H |
| 83 | B | $CH_3$ | NMeNMePh | 4-OAc | H |
| 84 | B | $CH_3$ | NHNHPh—3,4-$Cl_2$ | 4-OAc | H |
| 85 | B | $CH_3$ | 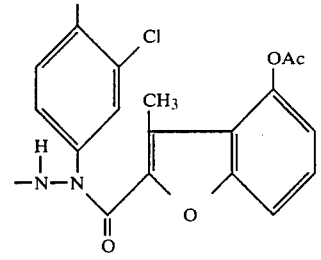 | 4-OAc | H |
| 86 | B | $CH_3$ | NHNHPh—p-Cl | 5-OAc | H |
| 87 | A | $CH_3$ | NHNHPh—m-OMe | 4-OAc | H |
| 88 | B | $CH_3$ | NHNHPh—p-OMe | 5-OAc | 4-$CH_2CH=CH_2$ |
| 89 | B | Pr | NHNHPh—p-OMe | 6-OAc | H |
| 90 | B | $CH_3$ | —NEtNHPh | 4-OAc | H |

TABLE Xa

| Example | M.P. | Analysis | |
|---|---|---|---|
| 77 | | Calc'd: | C, 57.62, H, 4.08, N, 6.72, Cl, 8.52 |
| | | Found: | 57.91, 3.93, 6.74, 8.24 |
| 78 | | Calc'd: | C, 64.90, H 5.12, N, 7.91 |
| | | | 64.19, 5.50, 7.85 |
| 79 | 226° C. | Calc'd: | C, 58.54, H, 4.09, N, 11.38 |
| | | Found: | 58.72, 4.05, 11.44 |
| 80 | 170–172° C. | Calc'd: | C, 64.54, H, 6.37, N, 8.85 |
| | | | 64.32, 6.03, 8.73 |
| 81 | | Calc'd: | C, 60.25, H, 4.18, N, 7.81, |

TABLE Xa-continued

| Example | M.P. | Analysis | |
|---------|------|----------|--|
| 82 | | Calc'd: | Cl, 9.88 |
| | | Found: | 60.37, 4.30, 7.76, 9.61 |
| | | Calc'd: | 69.22, H, 4.84, N, 6.73 |
| | | Found: | 69.03, 4.80, 6.66 |
| 83 | | Calc'd: | C, 68.15, H, 5.72, N, 7.95 |
| | | Found: | 67.81, 5.43, 7.75 |
| 84 | 236° C. | Calc'd: | C, 54.96, H, 3.59, N, 7.10. Cl, 18.04 |
| | | Found: | 54.90, 3.38, 5.95, 17.76 |
| 85 | 236° C. | Calc'd: | C, 59.12, H, 3.63, N, 4.69, Cl, 11.63 |
| | | Found: | 59.16, 3.42, 4.56, 11.81 |
| 86 | | Calc'd: | C, 60.25, H, 9.18, N, 7.81, Cl, 9.89 |
| | | Found: | 60.43, 4.26, 7.71, 9.81 |
| 87 | 172–175° C. | Calc'd: | C, 64.40, H, 5.12, N, 7.91 |
| | | Found: | 64.29, 5.03, 7.90 |
| 88 | | Calc'd: | C, 67.00, H, 5.58, N, 7.10 |
| | | Found: | 66.93, 5.93, 7.38 |
| 89 | | Calc'd: | C, 65.96, H, 5.80, N, 7.33 |
| | | Found: | 66.23, 5.91, 7.30 |
| 90 | | Calc'd: | C, 68.17, H, 5.72, N, 7.95 |
| | | Found: | 68.17, 5.89, 7.85 |

EXAMPLE 91

$N^2$-Phenyl-4-trimethylacetoxy-3-methylbenzofuran-2-carboxyhydrazide

To a cold (0° C.) solution of 4-hydroxy-3-methylbenzofuran-2-carboxylic acid (0.96 g, 5 mmol) in 25 ml THF was added trimethylacetyl chloride (2.5 ml, 20 mmol) dropwise followed by the addition of triethylamine (1.5 ml, 10.8 mmol). The mixture was stirred at 0° C. for 3 hours. Ether (150 ml) was added. The mixture was washed twice with pH 7 phosphate buffer (50 ml) and then with brine. Concentration of the dried ether extracts gave 2.2 g of crude product which was then redissolved in dry THF (20 ml) and cooled to 0° C. Phenylhydrazine (1.58 g, 15 mmol) was added. The mixture was stirred at 0° C. for 1 hour. The mixture was poured into cold (0° C.) 0.5N HCl (100 ml) and extracted with ethyl acetate. The combined organic extracts were washed with dilute HCl and brine and dried over MgSO$_4$. Concentration of the extracts gave a solid which after chromatography (silica gel, 20% EtOAc/Hexane) gave 780 mg (35.5% yield) of the title compound, m.p. 170°–171° C.

Analysis Calc'd: C, 69.77; H, 6.05; N, 7.65. Found: C, 69.66; H, 5.61; N, 7.26.

EXAMPLE 92

Ethyl 5,6-methylenedioxo-3-methylbenzofuran-2-carboxylate

Step 1

In 1 L DMF, sodiul hydride (8.7 g, 0.36 mole, 1 eq.) was added under N$_2$ at room temperature. Then sesamol (50 g, 0.36 mole) was added portionwise to the reaction mixture and stirred 20 minutes at room temperature. Ethyl 2-chloroacetoacetate (59.6 g, 1 eq.) was added slowly and the mixture was heated to 100° C. using an oil bath for 3 hours. The reaction mixture was poured into water and extracted with ethyl acetate, dried over magnesium sulfate and evaporated. The residue was flash chromatographed using hexane ethyl acetate 10%, to give: 50 g (52% yield) of ethyl 2-(3,4-methylenedioxyphenoxy)acetoacetate.

Step 2

The compound obtained from Step 1 (neat 22 g, 82.7 mmoles) was mixed and stirred (mechanically) with 44 g of PPA for 10 minutes. Dilution with water (400 ml), filtration and air dried, gave 18 g of the title compound (or 90% yield) m.p. 129°–130° C.

Analysis Calc'd: C, 62.90; H, 4.84. Found: C, 62.95; H, 4.98.

EXAMPLES 93–100

Following the procedure of Example 92, but substituting different substituted phenol for sesamol and/or ethyl-2-chloro-3-oxo-3-phenyl propanoate for ethyl-2-chloroacetoacetate, compounds of the Formula I, wherein Z is a bond, X is oxygen and T and V are hydrogen, were prepared. The compounds are listed as Examples 93 to 100 in Table XI. Physical data are presented in Table XIa.

TABLE XI

| Examples | $R_1$ | $R_2$ | $R_3$ | $R_4$ |
|----------|-------|-------|-------|-------|
| 93 | Me | OEt | 7-OMe | H |
| 94 | Me | OEt | 6-OMe | 7-OMe |
| 95 | Me | OEt | 5-NHAc | H |
| 96 | Me | OEt | 4-O-C(CO$_2$Et)(CH$_3$)-C(=O)- | H |
| 97 | Me | OEt | 5-OH | H |
| 98 | Me | OEt | 5-OH | 6-OMe |
| 99 | Ph | OEt | 6-OH | H |
| 100 | Pr | OEt | 4-OH | H |

TABLE XIa

| Example | M.P | Analysis | |
|---------|-----|----------|--|
| 93 | | Calc'd: | C, 66.60, H, 5.98 |
| | | Found: | 66.43, 6.07 |
| 94 | | Calc'd: | C, 63.63, H, 6.06 |
| | | Found: | 46.54, 4.87, 3.81 |
| 95 | | Calc'd: | C, 46.67, H, 4.17, N, 3.89 |
| | | Found: | 46.54, 4.87, 3.81 |
| 96 | 94–95° C. | Calc'd: | C, 62.06, H, 5.78 |
| | | Found: | 61.91, 5.70 |
| 97 | | Calc'd: | C, 65.65, H, 5.45 |
| | | Found: | 65.38, 5.60 |
| 98 | | Calc'd: | C, 62.40, H, 5.60 |
| | | Found: | 62.47, 5.51 |
| 99 | | Calc'd: | C, 72.33, H, 5.00 |
| | | Found: | 72.24, 5.08 |

EXAMPLE 101

Ethyl 5,6-dihydroxy-3-methylbenzofuran-2-carboxylate

To the compound of Example 92 (6 g, 24 mmoles) at −78° C., in CH$_2$Cl$_2$ (100 ml) was added BBr$_3$ (24 ml, 1M, 1 equivalent) dropwise, the mixture was stirred for 15 minutes, and then let to come to room temperature, and was stirred at room temperature for 1 hour, then 20 ml of MeOH was poured into the reaction mixture, the resulting solution was evaporated to dryness. The mixture was flash column chromatographed using hexane/ethyl acetate 20%+5% acetic acid to give: 5 g of the title compound (87% yield), m.p. 212°–214° C.

Analysis Calc'd: C, 61.01; H, 5.08. Found: C, 60.89; H, 5.29.

EXAMPLES 102 AND 103

Following the procedure of Example 101, compounds of the Formula I wherein Z is a bond, X is oxygen and T and V are hydrogen, were prepared. The compounds are listed as Examples 102 and 103 in Table XI. Physical data are presented in Table XIIa.

TABLE XII

| Examples | $R_1$ | $R_2$ | $R_3$ | $R_4$ |
|---|---|---|---|---|
| 102 | Me | OEt | 7-OH | H |
| 103 | Me | OEt | 6-OH | 7-OH |

TABLE XIIa

| Example | Analysis |
|---|---|
| 102 | Calc'd: C, 65.45, H, 5.43 |
|     | Found: 65.65, 5.20 |
| 103 | Calc'd: C, 61.00, H, 5.10 |
|     | Found: 60.84, 5.12 |

EXAMPLE 104

Ethyl 4-acetoxy-3-methylbenzofuran-2-carboxylate

To a cold (0° C.) solution of ethyl-4-hydroxy-3-methylbenzofuran-2-carboxylate (2.2 g, 10 mmol) in dry THF (30 ml) was added triethylamine (2.07 ml, 15 mmol) followed by acetyl chloride (0.85 ml, 12 mmol). The mixture was stirred at 0° C. for 1 hour, and at room temperature for 2 hours, and was then poured into ice water (200 ml). The white precipitate was collected by filtration.

EXAMPLES 105–115

Following the procedure of Example 104 but substituting methylchloroformate for acetyl chloride where appropriate, and other benzofuran derivatives for ethyl-4-hydroxy-3-methylbenzofuran-2-carboxylate, compounds of the Formula I, wherein Z is a bond, X is oxygen and T and V are hydrogen, were prepared. The compounds are listed as Examples 105–115 in Table XIII. Physical data are presented in Table XIIIa.

TABLE XIII

| Examples | $R_1$ | $R_2$ | $R_3$ | $R_4$ |
|---|---|---|---|---|
| 105 | Me | OEt | 4-O-C(=O)-OCH$_3$ | H |
| 106 | Me | OCH$_2$Ph—p-OMe | 4-O-C(=O)-OCH$_3$ | H |
| 107 | Me | OCH$_2$Ph—p-Cl | 4-O-C(=O)-OCH$_3$ | H |
| 108 | Me | OEt | 5-OAc | H |
| 109 | Me | OEt | 4-O-C(=O)-OMe | 5-CH$_2$SCH$_3$ |
| 110 | Me | OMe | 4-O-C(=O)-OMe | 5-CH$_2$CH=CH$_2$ |
| 111 | Me | OEt | 4-O-C(=O)-OMe | 5-Pr |
| 112 | Me | OEt | 5-O-C(=O)-OMe | 6-O-C(=O)-OMe |
| 113 | Me | OCH$_2$Ph | 4-O-C(=O)-OMe | 5-CH$_2$CH=CH$_2$ |
| 114 | Me | OCH$_2$Ph | 4-O-C(=O)-OPh | H |
| 115 | Me | OCH$_2$Ph—3,4-Cl$_2$ | 4-O-C(=O)-OMe | H |

TABLE XIIIa

| Example | m.p. | Analysis |
|---|---|---|
| 105 |  | Calc'd: C, 60.40, H, 5.03 |
|     |  | Found: C, 60.30, H, 4.75 |
| 106 |  | Calc'd: C, 64.80, H, 4.80 |
|     |  | Found: C, 65.20, H, 5.09 |
| 107 |  | Calc'd: C, 60.80, H, 4.00, Cl, 9.47 |
|     |  | Found: C, 60.43, H, 4.09, Cl, 9.36 |
| 108 |  | Calc'd: C, 64.12, H, 5.34 |
|     |  | Found: C, 64.24, H, 5.15 |
| 109 | 95–97° C. | Calc'd: C, 55.52, H, 4.97, S, 9.88 |
|     |  | Found: C, 55.29, H, 4.98, S, 10.06 |
| 110 | 97–99° C. | Calc'd: C, 63.13, H, 5.30 |
|     |  | Found: C, 62.92, H, 5.23 |
| 111 | 70–72° C. | Calc'd: C, 63.73, H, 6.29 |
|     |  | Found: C, 63.49, H, 6.17 |
| 112 |  | Calc'd: C, 54.45, H, 4.54 |
|     |  | Found: C, 54.19, H, 4.79 |
| 113 | 68–71° C. | Calc'd: C, 68.44, H, 5.30 |
|     |  | Found: C, 69.62, H, 5.35 |
| 114 |  | Calc'd: C, 72.11, H, 4.84 |
|     |  | Found: C, 72.15, H, 4.91 |
| 115 |  | Calc'd: C, 55.60, H, 3.40, Cl, 17.38 |
|     |  | Found: C, 55.58, H, 3.41, Cl, 17.35 |

EXAMPLE 116

Ethyl 4-allyloxy-3-methylbenzofuran-2-carboxylate

A mixture of ethyl-4-hydroxy-3-methylbenzofuran-2-carboxylate (11.0 g, 50 mmol), allyl bromide (4.8 ml, 55 mmol) and potassium carbonate (55 mmol) was refluxed in acetone (300 ml) for 4 hours. The resulting mixture was cooled, filtered and concentrated. The residue was chromatographed (silica gel, eluted with 5% ethyl acetate in hexane) to give 12 g of the title compound, m.p. 64°–65° C.

Analysis calc'd: C, 69.19; H, 6.20. Found: C, 69.40; H, 6.05.

EXAMPLES 117–122

Following the procedure of Example 116, but substituting the appropriate alkyl halide for allyl bromide or other benzofuran derivatives for ethyl-4-hydroxy-3-methylbenzofuran-2-carboxylate, compounds of the Formula I wherein Z is a bond, X is oxygen and T and V are hydrogen, were prepared. The compounds are listed as Examples 117 to 122 in Table XIV. Physical data were presented in Table XIVa.

TABLE XIV

| Examples | R$_1$ | R$_2$ | R$_3$ | R$_4$ |
|---|---|---|---|---|
| 117 | Me | OEt | 4-O-C(CH$_3$)=O (acetate group) | H |
| 118 | Me | H | 6-OCH$_2$CO$_2$Et | H |
| 119 | Me | OEt | 6-OCH$_2$CO$_2$Et | H |
| 120 | Me | OEt | 5-OCH$_2$CH=CH$_2$ | H |
| 121 | Me | OEt | 4-OCH$_2$CO$_2$Et | H |
| 122 | Pr | OEt | 4-OCH$_2$CH=CH$_2$ | H |

TABLE XIVa

| Example | m.p. | Analysis |
|---|---|---|
| 117 | 136–138° C. | Calc'd: C, 65.20, H, 5.83 |
|  |  | Found: C, 64.80, H, 5.75 |
| 118 | 167–168° C. | Calc'd: C, 60.43, H, 5.07 |
|  |  | Found: C, 60.08, H, 5.13 |
| 119 | 85–86° C. | Calc'd: C, 62.74, H, 5.92 |
|  |  | Found: C, 63.06, H, 6.50 |
| 120 |  | Calc'd: C, 69.23, H, 6.15 |
|  |  | Found: C, 69.16, H, 6.16 |
| 121 |  | Known compound, published |
| 122 |  | Calc'd: C, 70.79, H, 6.99 |
|  |  | Found: C, 70.95, H, 7.01 |

EXAMPLE 123

Ethyl 4-methoxy-3-methyl-7-propylbenzofuran-2-carboxylate

Following the procedure of Example 2, but substituting ethyl-4-hydroxy-7-propyl-3-methylbenzofuran-2-carboxylate for ethyl-4-hydroxy-3-methylbenzofuran-2-carboxylate, there was obtained the title compound, m.p. 43°–46° C.

Analysis calc'd: C, 69.54; H, 7.29. Found: C, 69.56; H, 7.10.

EXAMPLE 124

4-Chlorobenzyl 4-acetoxy-3-methylbenzofuran-2-carboxylate

4-Acetoxy-3-methylbenzofuran-2-carboxylic acid (1 g, 4.27 mmoles) was suspended in dichloro methyl methyl ether (20 ml) as a solvent and was refluxed for 1 hour. Evaporation to dryness gave 1.07 g (quantitative) of the corresponding acid chloride. The acid chloride (0.5 g, 2 mmoles) was dissolved in THF (30 ml) and parachlorobenzyl alcohol (0.3 g, 1 eq.) was added followed by Et$_3$N (0.2 g, 1 eq.) and the mixture was stirred for 1 hour at 25°, evaporated to dryness, and flash column chromatographed using toluene as eluant to give 0.5 g (71% yield) of the title compound, m.p. 95°–100° C.

Analysis calc'd: C, 63.6; H, 4.18; Cl, 9.89. Found: C, 63.9; H, 4.06; Cl, 9.66.

EXAMPLES 125–128

Following the procedure of example 124, but substituting other alcohols for 4-chlorobenzylalcohol, there was obtained the corresponding esters of the Formula I, wherein Z is a bond, X is oxygen and T and V are hydrogen. The compounds are listed as Examples 125 to 128 in Table XV. Physical data are presented in Table XVa.

TABLE XV

| Examples | R$_1$ | R$_2$ | R$_3$ | R$_4$ |
|---|---|---|---|---|
| 125 | Me | OCH$_2$Ph—P—OMe | 4-OAc | H |
| 126 | Me | OCH$_2$Ph | 4-OAc | H |
| 127 | Me | OCH$_2$Ph—3,4-Cl$_2$ | 4-OAc | H |
| 128 | Me | O—phenyl | 4-OAc | H |

TABLE XVa

| Example | m.p. | Analysis |
|---|---|---|
| 125 |  | Calc'd: C, 67.79, H, 5.08 |
|  |  | Found: C, 67.58, H, 4.76 |
| 126 | 116° C. | Calc'd: C, 70.36, H, 4.97 |
|  |  | Found: C, 70.55, H, .13 |
| 127 |  | Calc'd: C, 58.03, H, 3.58, Cl, 18.04 |
|  |  | Found: C, 57.97, H, 3.54, Cl, 18.11 |
| 128 | 102° C. | Calc'd: C, 68.34, H, 6.37 |
|  |  | Found: C, 68.21, H, 6.62 |

EXAMPLE 129

4-Chlorobenzyl 4-hydroxy-3-methylbenzofuran-2-carboxylate

To the compound of Example 124 (0.2 g, 0.55 mmoles) dissolved in MeOH (10 ml) was added 2–3 drops K$_2$CO$_3$ 10% w/v in H$_2$O and the reaction mixture was stirred at 25° overnight. HCl (0.1N, 20 ml) was added and the mixture was filtered. The solid was air dried to give 0.170 g or 96% of the title compound, m.p. 202°–204° C.

Analysis calc'd: C, 64.50; H, 4.10; Cl, 11.20. Found: C, 64.10; H, 4.36; Cl, 11.06.

EXAMPLES 130–133

Following the procedure of Example 129, compounds of the Formula I, wherein Z is a bond, X is oxygen and T and V are hydrogen, were similarly prepared. The compounds are listed as Examples 130 to 133 in Table XVI. Physical data are presented in Table XVIa.

TABLE XVI

| Examples | R$_1$ | R$_2$ | R$_3$ | R$_4$ |
|---|---|---|---|---|
| 130 | Me | O—CH$_2$Ph | 4-OH | H |
| 131 | Me | OCH$_2$Ph—3,4-Cl$_2$ | 4-OH | H |
| 132 | Me | OCH$_2$Ph—P—OMe | 4-OH | H |
| 133 | Me | O—phenyl | 4-OH | H |

TABLE XVIa

| Example | m.p. | Analysis |
|---|---|---|
| 130 | 183° C. | Calc'd: C, 72.33; H, 5.00 |
|  |  | Found: C, 72.26; H, 4.89 |
| 131 |  | Calc'd: C, 58.00; H, 3.40; S, 20.20 |
|  |  | Found: C, 57.89; H, 3.59; S, 20.40 |
| 132 |  | Calc'd: C, 69.23; H, 5.12 |
|  |  | Found: C, 69.12; H, 5.14 |
| 133 | 215° C. | Calc'd: C, 70.06; H, 6.61 |
|  |  | Found: C, 69.92; H, 6.41 |

EXAMPLE 134

Ethyl 5-allyl-4-hydroxy-3-methylbenzofuran-2-carboxylate

A solution of ethyl 4-allyloxy-3-methylbenzofuran-2-carboxylate (1.04 g, 4 mmol, Example 116) in dichlorobenzene was refluxed for 3 hours. The resulting solution was chromatographed (silica gel, 5% ethyl acetate in hexane) to give 8.7 g of the title compound (85% yield), m.p. 123° C.

Analysis calc'd: C, 68.19; H, 6.20. Found: C, 69.31; H, 6.40.

EXAMPLE 135

Ethyl 4-ally-5-hydroxy-3-methylbenzofuran-2-carboxylate

Following the procedure of Example 134 but substituting the compound of Example 120 for the compound of Example 116, there was obtained the title compound.

Analysis Calc'd: C, 69.23; H, 6.15. Found: C, 69.18; H, 6.56.

EXAMPLE 136

Ethyl 6-(N,N-dimethylthiocarbamyloxy-3-methylbenzofuran-2-carboxylate

Following the procedure of Example 4, but substituting an equivalent amount of ethyl 6-hydroxy-3-methylbenzofuran-2-carboxylate for ethyl 4-hydroxy-3-methylbenzofuran-2-carboxylate, there was obtained the title compound.

EXAMPLE 137

Ethyl 6-(N,N-dimethylcarbamylthio)-3-methylbenzofuran-2-carboxylate

Following the procedure of Example 6, but substituting an equivalent amount of the compound of Example 136 for the compound of Example 4, there was obtained the title compound, m.p. 112°–114° C.

Analysis calc'd: C, 58.61; H, 5.58; N, 4.56; S, 10.43. Found: C, 58.80; H, 5.63; N, 4.53; S, 10.13.

EXAMPLE 138

Ethyl 7-bromo-6-hydroxy-3-methylbenzofuran-2-carboxylate

A suspension of ethyl 6-hydroxy-3-methylbenzofuran-2-carboxylate (220 mg, 1 mmole) in methylene chloride (6 ml) was treated very slowly with a solution of bromine (160 mg, 1 mmole) in methylene chloride (4 ml) and with efficient stirring.

Evaporation of the solvent gave a gum which was crystallized from ethanol, 204 mg, m.p. 167°–168° C.

Analysis calc'd: C, 48.18; H, 3.71; Br, 26.71. Found: C, 48.01; H, 3.79; Br. 26.89.

The corresponding methyl ester is disclosed in *Chemical Abstracts*, 67, 82016e.

EXAMPLES 139-141

Following the procedure of Example 138 but substituting ethyl 4-hydroxy-3-methylbenzofuran-2-carboxylate for ethyl 6-hydroxy-3-methylbenzofuran-2-carboxylate, compounds of the Formula I, wherein Z is a bond, X is oxygen and V is hydrogen, were obtained. The compounds are listed as Examples 139 to 141 in Table XVII. By substituting chlorine for bromine, the compound listed as Example 141 in Table XVII was obtained. Physical data are presented in Table XVIIa.

TABLE XVII

| Examples | $R_1$ | $R_2$ | $R_3$ | $R_4$ | T |
|---|---|---|---|---|---|
| 139 | Me | OEt | 4-OH | 5-Br | H |
| 140 | Me | OEt | 4-OH | 5-Br | 7-Br |
| 141 | Me | OEt | 4-OH | 5-Cl | H |

TABLE XVIIa

| Example | m.p. | Analysis | |
|---|---|---|---|
| 139 | 136° C. | Calc'd: | C, 48.19, H, 3.71, Br, 26.71 |
|  |  | Found: | C, 47.98, H, 4.00, Br, 26.61 |
| 140 | 174° C. | Calc'd: | C, 38.13, H, 2.67, Br, 42.28 |
|  |  | Found: | C, 38.25, H, 2.50, Br, 42.15 |
| 141 |  | Calc'd: | C, 56.60, H, 4.35, Cl, 13.92 |
|  |  | Found: | C, 56.47, H, 4.36, Cl, 14.04 |

EXAMPLE 142

Ethyl 6-hydroxy-7-nitro-3-methylbenzofuran-2-carboxylate

A suspension of ethyl 6-hydroxy-3-methyl-benzofuran-2-carboxylate (220 mg, 1 mmole) in acetic acid (10 ml) was treated dropwise and with stirring with 0.2N nitric acid in acetic acid (5 ml). Solution occurred and then a yellow precipitate was formed. The solid was collected and washed with 50% aqueous acetic acid to give 98 mg of ethyl-6-hydroxy-7-nitro-3-methylbenzofuran-2-carboxylate, m.p. 186°–187.5° C.

Analysis calc'd: C, 54.34; H, 4.18; N, 5.28. Found: C, 54.42; H, 4.23; N, 5.07.

EXAMPLE 143

Ethyl 6-hydroxy-5-nitro-3-methylbenzofuran-2-carboxylate

An alternative work up procedure of Example 142 is to add water to the reaction mixture and extract the crude product with methylene chloride. Then by chromatography of the isolated material (Merck silica gel eluted with 1:1:4 ethyl acetate/methylene chloride/hexane) the less polar ethyl 6-hydroxy-5-nitro-3-methylbenzofuran-2-carboxylate, m.p. 155°–157° C., is isolated in minor amount as well as the forementioned 7-nitro-derivative.

EXAMPLES 144 AND 145

Following the same procedure of Examples 142 and 143 but substituting ethyl 4-hydroxy-3-methylbenzofuran-2-carboxylate for ethyl hydroxy-3-methylbenzofuran-2-carboxylate, there were obtained:

Example 144: ethyl 4-hydroxy-5-nitro-3-methylbenzofuran-2-carboxylate, m.p. 162° C.

Analysis calc'd: C, 54.34; H, 4.18; N, 5.28. Found: C, 54.18; H, 4.06; N, 5.31.

and

Example 145: ethyl 4-hydroxy-7-nitro-3-methylbenzofuran-2-carboxylate, m.p. 241° C.

Analysis calc'd: C, 54.34; H, 4.18; N, 5.28. Found: C, 54.02; H, 4.14; N, 5.15.

EXAMPLE 146

Ethyl 2-phenyl-9-methyl-1,3,2-dioxaborino[3,4-e]benzofuran-8-carboxylate

A mixture of ethyl 4-hydroxy-3-methylbenzofuran-2-carboxylate (11.0 g, 5 mmole), phenylboronic acid (12.2 g, 10 mmole) and toluene (350 ml) was distilled slowly until no more water came over. The condenser was placed vertically and 3 Angstrom molecular sieves (20 g) and S-trioxane (10 g) were added. The mixture was stirred mechanically (but gently to avoid reducing the sieves to a powder which retards the reaction) at 110°–120° C. (external) under slight pressure of nitrogen. Molecular sieves (10 g) and S-trioxane (5 g) were added three times at hourly intervals. Reaction (monitored by tlc (thin layer chromatography)) was incomplete after 5 hours but complete after 20 hours. The filtered solution was evaporated and the residue was recrystallized from acetonitrile (250 ml) to give 10.53 g of pure product, m.p. 171°–172° C.

Analysis calc'd: C, 67.89; H, 5.16; B, 3.22. Found: C. 67.24; H, 5.09; B, 3.11.

More product can be obtained by evaporation of the mother liquors to about 100 ml.

EXAMPLE 147

Ethyl 4-hydroxy-5-methylthiomethyl-3-methylbenzofuran-2-carboxylate

A mixture of methanethiol (3.85 g, 89.5 mmole) ethyl 2-phenyl-9-methyl-1,3,2-dioxaborino[3,4-e]benzofuran-8-carboxylate (5.04 g, 15 mmole) and methylene chloride (100 ml) was stirred in an ice-bath during the addition of anhydrous aluminium chloride (7.98 g, 60 mmole) in portions. After 30 minutes in the ice-bath, the reaction mixture was allowed to warm to room temperature and stirred for another 30 minutes. The reaction mixture was treated with ice cold N-hydrochloric acid and the organic layer was washed with water, dried with $MgSO_4$ and evaporated. The crude residue was purified by column chromatography (160 g Merck silica gel eluted with 1:4 ethyl acetate/hexane) affording 2.37 g (56.3% of pure product, m.p. 101° C.

Analysis calc'd: C, 60.00; H, 5.75; S, 11.40. Found: C, 60.08; H, 5.70; S, 11.31.

For other 5-alkylthiomethyl derivatives a four fold excess of alkanethiol was used.

In the case of the $HOOCCH_2S$— derivative it was necessary to use more $AlCl_3$ (5.2 moles base on the dioxaborinobenzofuran derivative).

EXAMPLES 148–151

Following the procedure of Example 147 but substituting different alkylthiols for methanethiol, compounds of the Formula I, wherein Z is a bond, X is oxygen and T and V are hydrogen, were prepared. The compounds are listed as Examples 148 to 151 in Table XVIII. Physical data are presented in Table XVIIIa.

TABLE XVIII

| Examples | $R_1$ | $R_2$ | $R_3$ | $R_4$ |
|---|---|---|---|---|
| 148 | Me | OEt | 4-OH | 5-$CH_2$SEt |
| 149 | Me | OEt | 4-OH | 5-$CH_2$SBu |
| 150 | Me | OEt | 4-OH | 5-$CH_2$S$CH_2$Ph |
| 151 | Me | OEt | 4-OH | 5-$CH_2$S$CH_2CO_2$H |

TABLE XVIIIa

| Example | m.p. | Analysis | |
|---|---|---|---|
| 148 | 82–84° C. | Calc'd: | C, 61.20, H, 6.16, S, 10.89 |
| | | Found: | C, 61.58, H, 6.22, S, 10.86 |
| 149 | 59–60° C. | Calc'd: | C, 63.33, H, 6.88, S, 9.94 |
| | | Found: | C, 63.40, H, 6.97, S, 9.93 |
| 150 | 103–4° C. | Calc'd: | C, 67.39, H, 5.66, S, 9.00 |
| | | Found: | C, 67.42, H, 5.82, S, 9.21 |
| 151 | 165–166° C. | Calc'd: | C, 55.55, H, 4.95, S, 9.89 |
| | | Found: | C, 55.76, H, 5.09, S, 10.15 |

EXAMPLE 152

Ethyl 5-ethoxymethyl-4-hydroxy-3-methylbenzofuran-2-carboxylate

A mixture of ethyl 2-phenyl-9-methyl-1,3,2-dioxaborino[3,4-e]benzofuran-2-carboxylate (840 mg, 2.5 mmole), ethanol (17 ml) and concentrated sulfuric acid (0.1 ml) was heated under reflux for 1 hour. The reaction mixture was evaporated partially and then partitioned between water and ether. The ethereal extract was washed with saturated sodium chloride solution, dried with $MgSO_4$ and evaporated. The crude product was purified by column chromatography (40 g Merck silica gel eluted with 1:3 ethyl acetate/hexane) thus providing 331 mg (47.6%) of product, m.p. 97°–98° C.

Analysis calc'd: C, 64.74; H, 6.52. Found: C, 64.74; H, 6.39.

EXAMPLES 153 AND 154

A solution of ethyl 2-phenyl-9-methyl-1,3,2-dioxaborino[3,4-e]benzofuran-2-carboxylate (1.68 g, 5 mmole) in tetrahydrofuran (20 ml) was cooled in an ice-bath and treated with 30% hydrogen peroxide (5 ml) in 1 ml portions. Tlc after 20 minutes detected no starting material. Ice (about 50 g) was added, followed by solid sodium bisulphite (5.0 g) in small portions with stirring. The mixture was extracted with ether (2×25 ml) and the extract was washed with saturated sodium chloride solution, dried with $MgSO_4$ and evaporated.

Chromatography of the crude product on Merck silica gel by elution with 1:1:2 ethyl acetate/methylene chloride/hexane containing 0.5% formic acid gave two products, listed below as Examples 153 and 154.

Example 153: Ethyl 4-hydroxy-5-(4-hydroxybenzyl)-3-methyl-benzofuran-2-carboxylate, the less polar compound, was obtained in a yield of 246 mg, m.p. 182°–184° C.

Analysis calc'd: C, 69.93; H, 5.56. Found: C. 69.68; H, 5.88.

Example 154: Ethyl 4-hydroxy-5-hydroxymethyl-3-methyl-benzofuran-2-carboxylate (304 mg), m.p. 148°–149° C.

Analysis calc'd: C, 62.39; H, 5.64. Found: C, 62,57; H, 5.61.

EXAMPLE 155

Ethyl 5-acetyl-4-hydroxy-3-methylbenzofuran-2-carboxylate

To a solution of ethyl 4-hydroxy-3-methylbenzofuran-2-carboxylate (220 mg, 1 mmol) in dichloroethane (10 ml) was added aluminum chloride (665 mg, 5 mmol). To the resulting brown solution was added acetyl chloride (0.178 ml, 2.5 mmol). The mixture was stirred for 5 hours at room temperature. Ice and water (20 ml) was added. The mixture was extracted with ethyl acetate. The extracts were dried and concentrated to a white solid which was then treated with 1 ml of 10% $K_2CO_3$ aqueous solution in 10 ml methanol for 2 hours. The resulting mixture was poured into 0.1N HCl (25 ml) and filtered. The solid obtained was recrystallized from ethyl acetate/toluene to give the title compound (130 mg, 50%).

Analysis calc'd: C, 64.12; H, 5,38. Found: C, 63,91; H, 5.33.

EXAMPLE 156

Ethyl 4,5-dihydroxy-3-methylbenzofuran-2-carboxylate

To the compound of Example 155 (260 mg, 1 mmol) in 10 ml acetic acid was added peracetic acid (0.8 ml of 40% solution). The mixture was stirred at room temperature for 2 days and was the poured into water. The solid was collected by filtration. Chromatography of the solid (silica gel, 20% ethyl acetate in toluene) gave the corresponding 5-acetoxy compound which was then treated with 10 ml ethanol with catalytic amount of para-toluenesulfonic acid at 50°-60° C. overnight. The ethanol was evaporated, the residue was dissolved in ethyl acetate which was then washed with $NaHCO_3$ and brine and the dried and concentrated. The residue was chromatographed (silica gel, 50% ethyl acetate/toluene) to give the title compound.

Analysis calc'd: C, 61.01; H, 5.08. Found: C, 60.87; H, 4.88.

EXAMPLE 157

5-Chloro-6-hydroxy-3-methylbenzofuran-2-carboxylic acid

3-Chloro-4-methyl-6-chloro-7-hydroxycoumarin was refluxed with NaOH (30 ml, 1N) for 1 hour. The mixture was washed with three 50 ml portions of ethyl acetate. Then acidification (HCl, 3N) of the aqueous phase followed by filtration of the solid that precipitated gave 0.5 g (54% yield) of the desired acid, m.p. 279°-280° C. In the ethyl acetate extract 0.2 g of decarboxylate product was recovered as a by product,

EXAMPLE 158

Ethyl-3-methyl-4-(2-hydroxypropoxy)-benzofuran-2-carboxylate

To a mixture of ethyl-3-methyl-4-(2-oxopropoxy)benzofuran-2-carboxylate (1.9 g, 6.8 mmoles, Example 117) in ethanol (100 ml) at 5° C. was added in portions, sodium borohydride (254 mg, 6.8 mmoles). The mixture was stirred for 10 minutes at 5° C. and 30 minutes at room temperature. The reaction was quenched with saturated ammonium chloride solution (1.5 ml) and concentrated. The residue was taken up in ether (100 ml), washed with water (25 ml), dried with $Na_2SO_4$, filtered and concentrated to obtain the title compound as an oil which crystallized on standing. The crystals were stirred with 25% ether in hexane (50 ml) for 30 minutes, filtered and then air dried, m.p. 94°-96° C.

Analysis calc'd: C, 64.73; H, 6.51. Found: C, 64.58; H, 6.51.

EXAMPLE 159

Ethyl (E)-3-(4-hydroxy-3-methylbenzofuran-2-yl)propenoate

A mixture of 4-hydroxy-3-methylbenzofuran (2.9 g, 20 mmoles) palladium III acetate (4.5 g, 20 mmoles), ethyl acrylate (2 g, 20 mmoles), acetic acid (50 ml) and dioxane (200 ml) was refluxed for 3 hours. The mixture was filtered and the filtrate concentrated and chromatographed to obtain 1 g of the title compound after recrystallization from toluene, m.p. 180°-182° C.

Mass spec.: $M^+$ at 246 m/e observed.

Analysis calc'd: C, 68.28; H, 5.73. Found: C, 68.08; H, 5.40.

EXAMPLES 160-163

Following the procedure of Example 158, but substituting other benzofuran derivatives for 4-hydroxy-3-methylbenzofuran of other $\alpha,\beta$-unsaturated esters for ethyl acrylate, compounds of the Formula I, wherein Z is $CR_{14}=CR_{15}$, X is oxygen and T and V are hydrogen, were prepared as Examples 160 to 163 in Table XIX. Physical data are presented in Table XIXa.

TABLE XIX

| Examples | $R_1$ | $R_2$ | $R_3$ | $R_4$ | $R_{14}$ | $R_{15}$ |
|---|---|---|---|---|---|---|
| 160 | $CH_3$ | OEt | 4-OH | H | Me | H |
| 161 | $CH_3$ | OEt | 4-OH | 5-Pr | H | H |
| 162 | $CH_3$ | OEt | 4-O-C(=O)-OMe | 5-Pr | H | H |
| 163 | $CH_3$ | OEt | 4-O-C(=O)-OMe | H | H | H |

TABLE XIXa

| Example | m.p. | Analysis |
|---|---|---|
| 160 | 188-190° C. | Calc'd: C, 68.28, H, 5.73 |
|  |  | Found: C, 68.23, H, 5.53 |
| 161 | 131-133° C. | Calc'd: C, 70.81, H, 6.89 |
|  |  | Found: C, 70.54, H, 6.54 |
| 162 | 101-103° C. | Calc'd: C, 65.88, H, 6.40 |
|  |  | Found: C, 65.43, H, 6.06 |
| 163 | 133-135° C. | Calc'd: C, 63.15, H, 5.29 |
|  |  | Found: C, 63.38, H, 5.13 |

EXAMPLE 164

(E)-3-(4-Hydroxy-3-methylbenzofuran-2-yl)propenoic acid

A mixture of ethyl-E-3-(4-hydroxy-3-methylbenzofuran-2-yl)propenoate (225 mg, 0.9 mmoles) (From Example 159), 2N sodium hydroxide (4 ml) and methanol (15 ml) was stirred at room temperature for 36 hours. The mixture was concentrated, acidified with 20% citric acid solution and extracted with ether. The ether solution was dried with $Na_2SO_4$, filtered and concentrated to obtain 190 mg of the title compound, m.p. 246°-248° C. (dec.).

Analysis Calc'd: C, 66.05; H, 4.60. Found: C, 66.13; H, 4.45.

EXAMPLE 165

3-(4-Hydroxy-3-methylbenzofuran-2-yl)propionic acid

A mixture of E-3-(4-hydroxy-3-methylbenzofuran-2-yl)propenoic acid (4.5 g, 20 mmoles), methanol (250 ml), 99% hydrazine hydrate (5 ml) and copper sulfate monohydrate (3 crystals) was stirred at room temperature for several days. The mixture was filtered and concentrated to remove methanol. The aqueous residue was acidified with 20% citric acid solution and extracted with diethyl ether. The ether solution was dried with $Na_2SO_4$, filtered, concentrated and chromatographed to obtain 950 mg of the title compound, m.p. 114°–117° C.

Analysis Calc'd: C, 65.44; H, 5.49. Found: C, 65.31; H, 5.37.

EXAMPLE 166

Ethyl 3-(4-hydroxy-3-methylbenzofuran-2-yl)propionate

A mixture of 3-(4-hydroxy-3-methylbenzofuran-2-yl)propionic acid (400 mg, 1.8 mmole) in 1% sulfuric acid in ethanol was kept at room temperature for 18 hours. The mixture was concentrated. The residue was taken up in diethyl ether, washed with water twice, dried with $Na_2SO_4$, filtered, concentrated and chromatographed to obtain 280 mg of the title compound, m.p. 61°–63° C.

Analysis Calc'd: C, 67.72; H, 6.49. Found: C, 67.71; H, 6.30.

EXAMPLE 167

Ethyl E-3-(4-allyloxy-3-methylbenzofuran-2-yl)propenoate

Following the procedure of Example 116 but substituting an equivalent amount of ethyl E-3-(4-hydroxy-3-methylbenzofuran-2-yl)propenoate for the compound of Example 1, there was obtained the title compound, m.p. 79°–80° C.

Analysis calc'd: C, 71.31; H, 6.33. Found: C, 71.49; H, 6.01.

EXAMPLE 168

Ethyl E-3-(5-allyl-4-hydroxy-3-methylbenzofuran-2-yl)propenoate

Following the procedure of Example 134 but substituting an equivalent amount of the title compound of Example 167 for ethyl-4-allyloxy-3-methylbenzofuran-2-carboxylate, there was obtained the title compound, m.p. 125°–127° C.

Analysis calc'd: C, 71.31; H, 6.33. Found: C, 71.33; H, 6.39.

EXAMPLE 169

$N^2$-(4-Methoxyphenyl)-E-3-(4-methoxycarbonyloxy-3-methylbenzofuran-2-yl)propenoic hydrazine Following the procedure of Example 9B, Step 1, but substituting 4-methoxyhydrazine for aniline and E-3-(4-hydroxy-3-methylbenzofuran-2-yl)propenoic acid for 4-hydroxy-3-methylbenzofuran-2-carboxylic acid, there was obtained the title compound, m.p. 166°–168° C.

Analysis calc'd: C, 63.62; H, 5.08; N, 7.06. Found: C, 63.82; H, 4.91; N, 6.83.

EXAMPLE 170

$N^2$-(4-Methoxyphenyl)-E-3-(4-hydroxy-3-methylbenzofuran-2-yl)propenoic hydrazide Following the procedure of Example 9B, Step 2, the title compound of Example 169 was hydrolyzed to the title compound, m.p. 218°–221° C.

Analysis calc'd: C, 67.44; H, 5.36. Found: C, 67.33; H, 5.35.

EXAMPLE 171

2-(4-Chlorobenzoyl)-4-hydroxy-3-methyl-benzofuran

A mixture of 2,6-dihydroxyacetophenone (4.5 g, 30 mmoles), p-chloro-ω-bromoacetophenone (6.9 g, 30 mmoles), potassium carbonate (4.1 g, 30 mmoles) and acetone (100 ml) was refluxed for 7 hours. The mixture was filtered and concentrated. The residue was partitioned between methylene chloride (250 ml) and in sodium hydroxide solution (100 ml). The aqueous phase was separated and acidified with 20% citric acid solution. The precipitated product was filtered and chromatographed to obtain 1.5 g of the title compound, m.p. 238°–241° C.

Analysis Calc'd: C, 67.02; H, 3.86; Cl, 12.36. Found: C, 66.95; H, 3.77; Cl, 11.96.

EXAMPLES 172–179

Following the procedure of Example 171, but substituting the appropriate substituted α-hydroxyacetophenone for 2,6-dihydroxyacetophenone or the appropriate ω-bromoacetophenone or ω-bromoacetone for p-chloro-ω-bromo-acetophenone, compounds of the Formula I, wherein Z is a bond, X is oxygen and T and V are hydrogen, were prepared. The compounds are listes as Examples 172 to 179 thus prepared. Physical data are presented in Table XXa.

TABLE XX

| Examples | $R_1$ | $R_2$ | $R_3$ | $R_4$ |
|---|---|---|---|---|
| 172 | $CH_3$ | Ph | 4-OCH$_2$–C(=O)–Ph | H |
| 173 | $CH_3$ | $CH_3$ | 4-OCH$_2$–C(=O)–$CH_3$ | H |
| 174 | $CH_3$ | $CH_3$ | 4-OH | H |
| 175 | $CH_3$ | Ph | 6-OAc | H |
| 176 | $CH_3$ | Ph | 6-OH | H |
| 177 | $CH_3$ | Ph | 4-OCH$_3$ | 6-OCH$_3$ |
| 178 | $CH_3$ | Ph | 4-OH | 5-Pr |
| 179 | $CH_3$ | Ph | 4-OH | H |

TABLE XXa

| Example | m.p. | Analysis | |
|---|---|---|---|
| 172 | 123–128° C. | Calc'd: | C, 77.82, H, 4.89 |
|  |  | Found: | C, 77.74, H, 5.07 |
| 173 | 105–109° C. | Calc'd: | C, 68.00, H, 6.11 |
|  |  | Found: | C, 68.19, H, 6.01 |
| 174 | 184–190° C. | Calc'd: | C, 69.46, H, 5.29 |
|  |  | Found: | C, 69.45, H, 5.18 |
| 175 | 124–126° | Calc'd: | C, 73.45, H, 4.79 |
|  |  | Found: | C, 73.37, H, 4.77 |
| 176 | 165–168° C. | Calc'd: | C, 76.37, H, 4.79 |
|  |  | Found: | C, 76.07, H, 4.56 |
| 177 |  | Calc'd: | C, 77.12, H, 5.75 |
|  |  | Found: | C, 77.01, H, 5.74 |
| 178 | 160–163° C. | Calc'd: | C, 77.52, H, 6.16 |

TABLE XXa-continued

| Example | m.p. | Analysis | | |
|---|---|---|---|---|
| 179 | 183–185° C. | Found: | C, 77.29; | H, 6.31 |
| | | Calc'd: | C, 76.17; | H, 4.79 |
| | | Found: | C, 76.12; | H, 4.59 |
| 185 | | Calc'd: | C, 68.92; | H, 4.08 |
| | | Found: | C, 68.99; | H, 4.27 |
| 186 | | Calc'd: | C, 64.12; | H, 5.38 |
| | | Found: | C, 64.10; | H, 5.39 |

EXAMPLES 180–184

Following the procedure of Example 164 but substituting the appropriate benzofuran-2-carboxylate for the title compound of Example 159, compounds of the Formula I, wherein Z is a bond, X is oxygen and T and V are hydrogen, were prepared. The compounds are listed as Examples 180–184 in Table XXI. Physical data are presented in Table XXIa.

TABLE XXI

| Examples | $R_1$ | $R_2$ | $R_3$ | $R_4$ |
|---|---|---|---|---|
| 180 | $CH_3$ | OH | 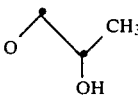 | H |
| 181 | $CH_3$ | OH | 4-OH | 5-Pr |
| 182 | Ph | OH | 6-OH | H |
| 183 | Pr | OH | 6-OH | H |
| 184 | $CH_3$ | OH | 5,6-OCH$_2$O— | |

TABLE XXIa

| EX. | m.p. | Analysis | | |
|---|---|---|---|---|
| 180 | 172–175° C. | Calc'd: | C, 62.39; | H, 5.63 |
| | | Found: | C, 62.17; | H, 5.57 |
| 181 | 195–198° C. (dec) | Calc'd: | C, 66.65; | H, 6.02 |
| | | Found: | C, 66.37; | H, 5.96 |
| 182 | | Calc'd: | C, 70.86; | H, 3.96 |
| | | Found: | C, 71.05; | H, 4.00 |
| 183 | 212–214° C. (dec) | Calc'd: | C, 65.45; | H, 5.49 |
| | | Found: | C, 64.85; | H, 5.48 |
| 184 | 290–293° C. | Calc'd: | C, 60.00; | H, 3.66 |
| | | Found: | C, 59.85; | H, 3.73 |

EXAMPLE 185

5-Acetyl-3-methylbenzofuran-2-carboxylic acid

Following the procedure of Example 155 but substituting 3-methylbenzofuran-2-carboxylic acid for ethyl 4-hydroxy-3-methylbenzofuran-2-carboxylate, the title compound was obtained.

Analysis calc'd: C, 64.71; H, 3.95. Found: C, 65.06; H, 4.14.

EXAMPLE 186–187

Following the procedure of Example 8, Method B, but substituting other substituted benzofuran-2-carboxylic acids for 4-hydroxy-3-methylbenzofuran-2-carboxylic acid, compounds of the Formula I, wherein Z is a bond, X is oxygen and T and V are hydrogen, were prepared. The compounds are listed as Examples 185 to 186 were prepared. Results are summarized as follows.

| Examples | $R_1$ | $R_2$ | $R_3$ | $R_4$ |
|---|---|---|---|---|
| 186 | Ph | OH | 6-OAc | H |
| 187 | Pr | OH | 6-OAc | H | physical data are presented below:

EXAMPLE 188

Ethyl-4-hydroxy-3-methylbenzothiophene-2-carboxylate

Step 1: Preparation of 2-Dimethylthiocarbamyloxy-6-hydroxyacetophenone

A mixture of 2,6-dihydroxyacetophenone (22.8 g, 150 mmol), $K_2CO_3$ (22.7 g, 165 mmol), dimethylthiocarbamoylchloride (27.8 g, 22.5 mmol) was stirred at room temperature in 300 ml acetone for 30 hours. The mixture was filtered. The solution was evaporated and the residue was chromatographed to give 9 g of 2-dimethylthiocarbamyloxy-6-hydroxyacetophenone.

Step 2: Preparation of 2-Dimethylthiocarbamyloxy-6-acetoxyacetophenone

The product from Step 1 (572 mg, 2.52 mmol) in THF (10 ml) at 0° C. was treated with acetyl chloride (196 μl, 2.77 mmol) followed by triethylamine (418 μl, 3 mmol). The mixture was stirred for one hour at 0° C. Dilute HCl (20 ml, 0.2N) was added and the mixture was extracted with ethyl acetate. Concentration of the dried organic extracts gave the title compound.

Step 3: Preparation of 2-Dimethylcarbamylthio-6-hydroxyacetophenone

A mixture of the product from Step 2 (1.60 g) and 4-hydroxy-2,2,6,6-tetramethylpiperidinoxy free radical (100 mg) was refluxed in o-dichlorobenzene (20 ml) for 20 hours. The resulting mixture was chromatographed to give 2-dimethylcarbamylthio-6-hydroxyacetophenone (800 mg, 50%).

Step 4: Preparation of 2-Thio-6-hydroxyacetophenone

A mixture of the product of Step 3 (550 mg) and 5 ml 2N NaOH and 10 ml methanol was refluxed for 5½ hours. Methanol was evaporated under vacuum, the residue was acidified with cold dilute HCl (0.5N, 10 ml) and extracted with ethyl acetate. The organic extracts were concentrated and chromatographed (silica gel 30% ethyl acetate/toluene) to give 2-thiol-6-hydroxyacetophenone (250 mg).

Step 5: Preparation of Ethyl(2-aceto-3-thiophenoxy)acetate

Following the procedure of Step 1 but substituting ethyl bromo acetate for dimethylthiocarbamoyl chloride and substituting 2-thio-6-hydroxyacetophenone for 2,6-dihydroxy acetophenone there was obtained ethyl-(2-aceto-3-thiophenoxy)acetate.

Step 6: Preparation of Ethyl-4-hydroxy-3-methylbenzothiophene-2-carboxylate

The product of Step 5 was treated with sodium ethoxide and ethanol at 0° C. for 2 hours, dilute (1N, HCl) acid was then added and the mixture was extracted with ethyl acetate. The organic extrcts were dried and concentrated to give the title compound, m.p. 183°–184° C.

Analysis calc'd: C, 60.97; H, 5.12; S, 13.57. Found: C, 60.87; H, 4.96; S, 13.87.

EXAMPLE 189

N²-[N¹-methyl-N¹-phenyl]-4-hydroxy-3-methylbenzofuran-2-carboxy-hydride

Following the procedure of Example 9B step 1 and 2 but substituting and equivalent amount of N¹-methyl-N¹-phenyl hydrazine for aniline, there was obtained the title compound. m.p. 207°–210° C.

Analysis, Calc'd: C, 68.91; H, 5.44; N, 5.24. Found: C, 68.74; H, 5.33; N, 9.32.

EXAMPLE 190

Benzyl 4,7-dihydroxy-3-methylbenzofuran-2-carboxylate

A. Preparation of Ethyl 4-hydroxy-7-acetyl-3-methylbenzofuran-2-carboxylate

In the preparation of the compound of Example 155, the title compound was also formed in small quantity which can be separated by extensive chromatography.

B. Preparation of 4,7-dihydroxy-3-methylbenzofuran-2-carboxylic acid

Following the procedure of Example 156 but substituting Ethyl 4-hydroxy-7-acetyl-3-methylbenzofuran-2-carboxylate for the compound of Example 155. There is obtained the intermediate Ethyl-7-acetoxy-4-hydroxy-3-methylbenzofuran-2-carboxylate which is hydrolyzed in an aqueous acetic acid solution of hydrochloric acid (6 hours, 100° C.) to give the title compound.

C. Preparation of 4,7-Diacetoxy-3-methylbenzofuran-2-carboxylic acid

Following the procedure of Example 8 method B but substituting the compound of Example 1, step C with the compound of Example 190, step B, there is obtained the title compound.

D. Preparation of Benzyl 4-7-Diacetoxy-3-methylbenzofuran-2-carboxylate

Following the procedure of Example 124 but substituting an equivalent amound of the title compound of Example 190 step C for 4-acetoxy-3-methylbenzofuran-2-carboxylic acid and benzyl alcohol for 4-chlorobenzyl alcohol, there is obtained the title compound.

E. Preparation of Benzyl 4,7-dihydroxy-3-methylbenzofuran-2-carboxylate

Treatment of the title compound of Example 190, step D with 10 ml ethanol with catalytic amount of p-toluenesulfonic acid at 50°–60° C. overnight gives the title compound.

EXAMPLE 191

N²-phenyl-4,7-dihydroxy-3-methylbenzofuran-2-carboxyhydrazide

A. Preparation of N²-phenyl-4,7-diacetoxy-3-methylbenzofuran-2-carboxyhydrazide Following the procedure of Example 9 but substituting an equivalent amount of the compound of Example 190, step C for the compound of Example 8 and substituting an equivalent amount of phenylhydrazine for aniline, there is obtained the title compound.

B. Preparation of N²-phenyl-4,7-dihydroxy-3-methylbenzofuran-2-carboxyhydrazide Following the procedure of Example 190, Step E but substituting an equivalent amount of the compound of Example 191, step A for the compound of Example 190, step D there is obtained the title compound.

EXAMPLE 192

Benzyl 4,7-dihydroxy-5-propyl-3-methylbenzofuran-2-carboxylate

Following the procedure of Example 190, step A to E but substituting an equivalent amount of ethyl 4-hydroxy-5-propyl-3-methylbenzofuran-2-carboxylate for the 4-hydroxy-3-methylbenzofuran-2-carboxylate, there is obtained the title compound.

EXAMPLE 193

N²-phenyl-4,7-dihydroxy-5-propyl-3-methylbenzofuran-2-carboxyhydrazide

Following the procedure of Example 191, step A to B but substituting an equivalent amount of 4,7-diacetoxy-5-propyl-3-methylbenzofuran-2-carboxylic acid (obtainable as an intermediate as in the preparation of Example 190, step C there is obtained the title compound.

EXAMPLE 194

2-carboethoxy-3-methyl-4-hydroxy-5-propyl-7-chlorobenzofuran

Step A: Preparation of 2,6-dihydroxy-3-propyl-5-chloro-acetophenone

A mixture of 2,6-dihydroxy-3-propylacetophenone (40 gm, 0.206 mole), N-chlorosuccinimide (40 gm; 0.300 mole) in methylene chloride (3 liters) was stirred at room temperature for a period of two days. The reaction mixture was poured on a 3 liter fritted-disk funnel filled with silica gel and elution was carried out with methylene chloride. Evaporation of the filtrate yielded 2,6-dihydroxy-3-propyl-5-chloro-acetophenone, m.p. 69°–70° C.

¹H NMR 0.93 (t, J=7 Hz, 3H, CH₃), 1.63 (sextet, J=7 Hz, 2H, CH₂), 2.53 (t, J=7 Hz, 2H, CH₂), 2.73 (s, 3H, CH₃), CH₂), 6.33 (s, 1H, proton ortho to chloro), 13.13 (s, 1H, OH).

Step B: Preparation of 2-carboethoxymethoxy-6-hydroxy-5-propyl-3-chloro-acetophenone A mixture of 2,6-dihydroxy-5-chloro-3-propylacetophenone (38.5 gm, 0.169 mole), ethyl bromoacetate (18.6 ml; 0.169 mole) and potassium carbonate (23.24 gm; 0.169 mole) in acetone (3 liters) was refluxed for a period of 2.5 hours. The reaction mixture was filtered through Celite (diatomaceous earth) and the filtrate was concentrated in vacuo to yield a residue that was purified by chromatography on silica gel and eluted with 5% ethyl acetate in hexane to yield 2-carboethoxymethoxy-6-hydroxy-5-propyl-3-chloroacetophenone, m.p. 46°–47° C.

¹H NMR 0.93 (t, J=7 Hz, 3H, CH₃), 1.30 (t, J=7 Hz, 3H, CH₃, 1.63 (sextet, J=7 Hz, 2H, CH₂), 2.57 (t, J=7 Hz, 2H, CH₂), 2.77 (s, 3H, CH₃), 4.27 (q, J=7 Hz, 2H, CH₂O), 4.73 (s, 2H, CH₂), 7.23 (s, 1H, proton ortho to chloro), 12.50 (s, 1H, OH).

Step C: Preparation of 2-carboethoxy-3-methyl-4-hydroxy-5-propyl-7-chloro-benzofuran A solution of 2-carboethoxymethoxy-6-hydroxy-5-propyl-3-chloro-acetophenone (43 gm; 0.136 mole) in freshly-distilled absolute ethanol (1.2 liter) was brought to reflux and a 1M solution of sodium ethoxide (273 ml; 0.273 mole) was added rapidly. The reaction mixture was refluxed for a period of 1 hour. It was cooled to room temperature and poured into 0.5N hydrochloric acid and extracted with ethyl acetate. The organic phase was dried ($Na_2SO_4$) and concentrated in vacuo. The residue was chromatographed on silica gel and eluted with 15% ethyl acetate in hexane to yield 22.0 gm of 2-carboethoxy-3-methyl-4-hydroxy-5-propyl-7-chlorobenzofuran, m.p. 165°-166° C.

$^1$H NMR 1.00 (t, J=7 Hz, 3H, $CH_3$), 1.25 (t, J=7 Hz, 3H, $CH_3$), 1.63 (sextet, J=7 Hz, 2H, $CH_2$), 2.57 (t, J=7 Hz, 2H, $CH_2$), 2.76 (s, 3H, $CH_2$), 4.43 (q, J=7 Hz, 2H, $CH_2O$), 5.19 (s, 1H, OH), 7.15 (s, 1H, proton ortho to chloro).

EXAMPLE 195

2-carboethoxy-3-methyl-4-hydroxy-5-propyl-7-fluorobenzofuran

Step A: Preparation of 2-hydroxy-6-allyloxyacetophennone

A mixture of 2,6-dihydroxyacetophenone (300 gm; 1.97 moles), potassium carbonate (271 gm; 1.97 moles) and allyl bromide (271 ml; 2.25 moles) in acetone (10 liters) was refluxed for a period of three hours. The reaction mixture was cooled, filtered through Celite and concentrated in vacuo. The residue was chromatographed on silica gel using toluene as eluent to yield 305 gms (80%) of 2-hydroxy-6-allyloxy acetophenone, m.p. 54°-55° C.

$^1$H NMR 2.40 (s, 3H, $CH_3$), 4.57 (d, J=6 Hz, 2H, $OCH_2$), 5.57 (m, 1H, CH), 6.33 (m, 2H, $CH_2$), 6.62 (d, J=9 Hz, 1H, proton ortho to hydroxyl), 6.83 (d, J=9 Hz, 1H, proton ortho to allyloxy), 7.72 (t, J=9 Hz, 1H, proton para to acetyl).

Anal. Calcd for $C_{11}H_{12}O_3$: C, 68.75; H, 6.25. Found: C, 68.66; H, 6.54.

Step B: Preparation of 2,6-dihydroxy-3-allylacetophenone

2-Hydroxy-6-allyloxy-acetophenone (30 gm; 0.156 mole) was heated under nitrogen at 190° C. for a period of 10 minutes. The mixture was cooled and slurried with carbon tetrachloride to yield 2,6-dihydroxy-3-allyl-acetophenone, m.p. 67°-68° C. in quantitative yield.

$^1$H NMR 2.77 (s, 3H, $CH_3$), 3.37 (d, J=6 Hz, 2H, $CH_2$), 5.37 (m, 1H, CH), 6.00 (m, 2H, $CH_2$), 6.33 (d, J=9 Hz, 1H, proton ortho to hydroxyl), 7.17 (d, J=9 Hz, 1H, proton meta to hydroxy).

Anal. Calcd. for $C_{11}H_{12}O_3$: C, 68.75; H, 6.25. Found: C, 68.90; H, 6.21.

Step C: Preparation of 2,6-dihydroxy-3-propylacetophenone 2,6-dihydroxy-3-allyl-acetophenone (30 gm; 0.156 mole) dissolved in ethanol (150 ml) was hydrogenated in a Parr apparatus in presence of 5% palladium on carbon. The catalyst was removed by filtration and the filtrate was concentrated to dryness to yield 30 gm of 2,6-dihydroxy-3-propylacetophennone, m.p. 76°-78° C.

$^1$H NMR 0.97 (t, J=7 Hz, 3H, $CH_3$), 1.60 (sextet, J=7 Hz, 2H, $CH_2$), 2.53 (t, J=7 Hz, 2H, $CH_2$), 2.73 (s, 3H, $CH_3$), 6.30 (d, J=9 Hz, 1H, proton ortho to hydroxy), 7.13 (d, J=9 Hz, 1H, proton meta to hydroxy).

Anal. Calcd for $C_{11}H_{14}O_3$: C, 68.04; H, 7.21. Found: C, 68.05; H, 7.34.

Step D: Preparation of 2,6-dihydroxy-3-propyl-5-fluoro-acetophenone

1. A solution of 2,6-dihydroxy-3-propylacetophenone (194 mg; 1 mmole) in Freon (fluorotrichloromethane) (30 ml) was cooled at −78° C. and trifluoromethylhypofluorite was bubbled through the solution slowly, monitoring the reaction by TLC until about half of the material had reacted. The mixture was poured onto a silica gel column and elution with 15% ethylacetate in hexane gave 40 mg of 2,6-dihydroxy-3-propyl-5-fluoro-acetophenone.

$^1$H NMR 0.93 (t, J=7 Hz, 3H, $CH_3$), 1.67 (sextet, J=7 Hz, 2H, $CH_2$), 2.57 (t, J=7 Hz, 2H, $CH_2$), 2.80 (s, 3H, $CH_3$), 6.18 (d, J=6 Hz, 1H, OH), 7.13 (d, J-11 Hz, 1H, proton ortho to fluoro).

2a. Preparation of 2,6-dimethoxy-3-propyl-5-fluoro-acetophenone.

A solution of 2,6-dimethoxy-3-propylacetophenone (21.0 gm; 94.6 mmoles) in Freon (30 ml) was cooled at −78° C. and trifluoromethylpofluoride was bubbled through the solution slowly. The reaction was monitored by TLC until about 75% of the material reacted. The mixture was poured onto a silica gel column and elution with 15% ethyl acetate in hexane gave 11.1 g of 2,6-dimethoxy-3-propyl-5-fluoroacetophenone and 9.0 gm of unreacted 2,6-dimethoxy-3-propyl-acetophenone.

$^1$H NMR 0.97 (t, J=7 Hz, 3H, $CH_3$), 1.67 (sextet, J=7 Hz, 2H, $CH_2$), 2.50 (t, J=7 Hz, 2H, $CH_2$), 2.50 (s, 3H, $CH_3$), 3.70 (s, 3H, $CH_3$), 3.82 (d, J=3 Hz, 3H, $CH_3$), 6.90 (d, J=11 Hz, 1H, proton ortho to fluoro).

2b. Preparation of 2,6-dihydroxy-3-propyl-5-fluoro-acetophenone

To a solution of 2,6-dimethoxy-3-propyl-5-fluoro-acetophenone (3.0 gm; 12.5 mmoles) in methylene chloride (32 ml) cooled to −78° C., was added dropwise over a period of 1 hour a 1M solution of boron tribromide (56 ml; 56 mmoles). The temperature was allowed to rise to room temperature and the reaction mixture was stirred for 3 hours. It was then cooled to −78° C. and methanol (20 ml) was added rapidly. The resulting solution was poured in water, the phases were separated and the aqueous phase was extracted with methylene chloride. The organic phases were combined, washed with brine, dried ($Na_2SO_4$), and concentrated in vacuo. The residue was chromatographed on silica gel and eluted with 7% ethyl acetate in hexane to yield 1.5 gm (58%) of 2,6-dihydroxy-3-propyl 5-fluoro acetophenone.

$^1$H NMR 0.93 (t, J=7 Hz, 3H, $CH_3$), 1.63 (sextet, J=7 Hz, 2H, $CH_2$), 2.50 (t, J=7 Hz, 2H, $CH_2$), 2.73 (s, 3H, $CH_3$), 5.93 (d, J=6 Hz, 1H, OH), 7.10 (d, J=11 Hz, 1H, proton ortho to fluoro).

Step E: Preparation of 2-carboethoxymethoxy-6-hydroxy-5-propyl-3-fluoro-acetophenone A mixture of 2,6-dihydroxy-5-fluoro-3-propyl-acetophenone (3.5 gm, 16.5 mmoles), ethyl bromoacetate (2.0 ml; 18.1 mmoles) and potassium carbonate (2.27 gm; 16.5 mmoles) in acetone (1 liter) was refluxed for a period of 0.5 hour. The reaction mixture was filtered through Celite and the filtrate was concentrated in vacuo to yield a residue that was purified by chromatography on silica gel and eluted with 10% ethyl acetate in hexane to yield 4.2 gm (86%) of 2-carboethoxymethoxy 6-hydroxy-5-propyl-3-fluoro-acetophenone.

$^1$H NMR 0.93 (t, J=7 Hz, 3H, $CH_3$), 1.27 (t, J=7 Hz, 3H, $CH_3$), 1.63 (sextet, J=7 Hz, 2H, $CH_2$), 2.53 (t, J=7 Hz, 2H, $CH_2$), 2.77 (s, 3H, $CH_3$), 4.20 (q, J=7 Hz, 2H, CH₂O), 4.80 (s, 2H, CH₂), 7.03 (d, J=11 Hz, 1H, proton ortho to fluoro).

Step F: Preparation of 2-carboethoxy-3-methyl-4-hydroxy-5-propyl-7-fluoro-benzofuran To a solution of 2-carboethoxymethoxy 6-hydroxy-5-propyl-3-fluoro-acetophenone (15 gm; 50.0 mmoles) in freshly-distilled absolute ethanol (0.5 liter) was brought to reflux and a 1M solution of sodium ethoxide (100 ml; 100 mmoles was added rapidly. The reaction mixture was refluxed for a period of 1 hour. It was cooled to room temperature and poured into 0.5N hydrochloric acid and extracted with ethyl acetate. The organic phase was dried (Na₂SO₄) and concentrated in vacuo. The residue was chromatographed on silica gel and eluted with 10% ethyl acetate in hexane to yield 9.0 gm of 2-carboethoxy 3-methyl-4-hydroxy-5-propyl-7-fluorobenzofuran.

¹H NMR 1.00 (t, J=7 Hz, 3H, CH₃), 1.43 (t, J=7 Hz, 3H, CH₃), 1.63 (sextet, J=7 Hz, 2H, CH₂), 2.57 (t, J=7 Hz, 2H, CH₂), 2.80 (s, 3H, CH₃), 4.47 (q, J=7 Hz, 2H, CH₂O), 4.97 (s, 1H, OH), 6.90 (s, 1H, proton ortho to fluoro).

EXAMPLE 196

Benzyl 3-methyl-4-hydroxy-5-propyl-7-chlorobenzofuran-2-carboxylate

A mixture of 3-methyl-4-hydroxy-5-propyl-7-chloro-benzofuran-2-carboxylic acid (0.5 gm; 1.9 mmole), potassium carbonate (0.26 gm; 1.9 mmole) and benzyl bromide (0.22 ml; 1.9 mmole) in acetone (100 ml) was refluxed for a period of 2 hours. The solids were filtered off and the filtrate was concentrated in vacuo. The residue was chromatographed on silica gel and eluted with 15% ethyl acetate in hexane to yield 200 mg (30%) of benzyl 3-methyl-4-hydroxy-5-propyl-7-chlorobenzofuran-2-carboxylate, m.p. 119°-120° C.

¹H NMR: 0.97 (t, J=7 Hz, 3H, CH₃), 1.60 (sextet J=7 Hz, 2H, CH₂), 2.53 (t, J=7 Hz, 2H, CH₂), 2.73 (s, 3H, CH₃), 5.10 (s, 1H, OH), 5.43 (s, 2H, CH₂), 7.10 (s, 1H, H₆), 7.40 (m, 5H, aromatic protons).

EXAMPLE 197

Benzyl 3-methyl-4-hydroxy-5-propyl-7-fluorobenzofuran-2-carboxylate

By using 3-methyl-4-hydroxy-5-propyl-7-fluorobenzofuran-2-carboxylic acid in place of 3-methyl-4-hydroxy-5-propyl-7-chlorobenzofuran-2-carboxylic acid and following the procedure of Example 196, the title compound is obtained.

Claims to the invention follow.
What is claimed is:

1. A compound of Formula I:

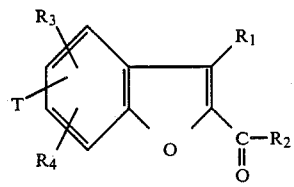

wherein the compound is selected from the following group:

| Compound | R₁ | R₂ | R₃ | R₄ | R |
|---|---|---|---|---|---|
| 172 | CH₃ | OC(CH₃)₃ | 4-OH | H | H |
| 216 | Me | OEt | 4-OH | 5-CH₂OH | H |
| 217 | Me | OEt | 5-OAc | H | H |
| 218 | Me | OEt | 4-OH | 5-CH₂OEt | H |
| 226 | Me | OEt | 4-O-C(CH₃)₂-C(=O)- (acetonide/ketal) | H | H |
| 227 | Me | O-phenyl | 4-OAc | H | H |
| 230 | Me | OMe | 4-O-CH(OMe)- | 5-CH₂CH=CH₂ | H |
| 231 | Me | OEt | 4-O-CH(OMe)- | 5-Pr | H |
| 241 | Me | OEt | 5-OH | 4-CH₂CH=CH₂ | H |
| 242 | Me | OEt | 4-OH | 5-CH₂CH=CH₂ | H |
| 245 | Ph | OEt | 6-OH | H | H |
| 246 | Me | OEt | 5-NHAc | H | H |
| 250 | Pr | OEt | 4-OH | H | H |
| 252 | Me | OEt | 4-OH | 5-Pr | H |
| 253 | Ph | OEt | 4-OH | H | H |
| 254 | Ph | OEt | 4-OH | 5-C(=O)Ph | H |
| 259 | Me | O-phenyl | 4-OH | H | H |
| 261 | CH₃ | OH | 4-OH | 5-Pr | H |
| 263 | Me | O-CH=C(Me)-O (cyclic, with C=O) | 4-OH | H | H |
| 288 | CH₃ | —OEt | 4-O-CH(OMe)- | H | H |
| 366 | CH₃ | OEt | 4-OH | 5-CH₂CH₂CH₃ | 7-F |
| 367 | CH₃ | OEt | 4-OH | 5-CH₂CH₂CH₃ | 7-Cl |

2. A compound of claim 1 which is: 172, 231, 288, 366, or 367.

3. A compound of claim 1 which is: 231, 288, 366, or 367.

4. A method of inhibiting mammalian leukotriene biosynthesis or action which comprises administering to a mammal a pharmaceutically effective amount of a compound of claim 1.

5. A method of inhibiting human leukotriene biosynthesis or action which comprises administering to a human a pharmaceutically effective amount of a compound of claim 1.

6. A method of treating pulmonary conditions, inflammation, cardiovascular conditions, or skin conditions which comprises administering to a human in need of such treatment a pharmaceutically effective amount of a compound of claim 1.

* * * * *